US009822413B2

(12) United States Patent
Gromminger et al.

(10) Patent No.: US 9,822,413 B2
(45) Date of Patent: *Nov. 21, 2017

(54) MULTIPLEX DETECTION OF DNA THAT ORIGINATES FROM A SPECIFIC CELL-TYPE

(71) Applicant: LifeCodexx AG, Constance (DE)

(72) Inventors: Sebastian Gromminger, Constance (DE); Wera Hofmann, Constance (DE); Hamed Said, Constance (DE)

(73) Assignee: LifeCodexx AG, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,391

(22) Filed: May 8, 2015

(65) Prior Publication Data

US 2015/0322513 A1 Nov. 12, 2015

(30) Foreign Application Priority Data

May 9, 2014 (EP) .................................... 14167769

(51) Int. Cl.
*C12Q 1/68* (2006.01)

(52) U.S. Cl.
CPC ......... *C12Q 1/6881* (2013.01); *C12Q 1/6883* (2013.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,804,375 A | 9/1998 | Gelfand et al. | |
| 5,994,056 A | 11/1999 | Higuchi | |
| 6,200,756 B1 | 3/2001 | Herman et al. | |
| 6,258,569 B1 | 7/2001 | Livak et al. | |
| 6,331,393 B1 | 12/2001 | Laird et al. | |
| 6,727,356 B1 | 4/2004 | Reed et al. | |
| 6,929,907 B2 | 8/2005 | Agris | |
| 2012/0252015 A1* | 10/2012 | Hindson | C12Q 1/6883 435/6.11 |

FOREIGN PATENT DOCUMENTS

| | | |
|---|---|---|
| EP | 0 512 334 B1 | 9/1999 |
| EP | 0 706 649 B1 | 1/2001 |
| EP | 0 792 374 B1 | 1/2001 |
| EP | 0 954 608 B1 | 5/2006 |
| EP | 1 185 695 B1 | 7/2006 |
| EP | 0 543 942 B2 | 11/2006 |
| EP | 1 235 938 B1 | 2/2012 |
| WO | 2005/118852 A2 | 12/2005 |
| WO | 2007/132166 A3 | 11/2007 |
| WO | 2007/132167 A3 | 11/2007 |
| WO | 2010/033639 A9 | 3/2010 |
| WO | 2011/018600 A1 | 2/2011 |
| WO | 2011/034631 A1 | 3/2011 |
| WO | 2012/092592 A1 | 7/2012 |

OTHER PUBLICATIONS

He et al., "Development of a multiplex MethyLight assay for the detection of multigene methylation in human colorectal cancer", Cancer Genetics and Cytogenetics, Oct. 1, 2010, vol. 202:1, pp. 1-10.
Olkhov-Mitsel et al., "Novel Multiplex MethyLight Protocol for Detection of DNA Methylation in Patient Tissues and Bodily Fluids", Scientific Reports, Mar. 21, 2014, vol. 4: 4432, pp. 1-8.
Snellenberg et al., "Development of a multiplex methylation-specific PCR as candidate triage test for women with an HPV-positive cervical scrape", BMC Cancer, Nov. 23, 2012, vol. 12:551, pp. 1-10.
Nygren et al., "Quantification of Fetal DNA by Use of Methylation-Based DNA Discrimination", Clinical Chemistry, Aug. 20, 2010, vol. 56:10, pp. 1627-1635.
Campan et al., "MethyLight", DNA Methylation: methods and Protocols, Second Edition , 2009, vol. 57, pp. 325-337.
Swift-Scanalan et al., "Two-color quantitative multiplex methylation-specific PCR", BioTechniques, Feb. 1, 2006, vol. 40:2, pp. 210-219.
Weisenberger et al., "Analysis of repetitive element DNA methylation by MethyLight", Nucleic Acids Research, Dec. 2, 2005, vol. 33:21, pp. 6823-6836.
Weisenberger et al., "DNA methylation analysis by digital bisulfite genomic sequencing and digital MethyLight", Nucleic Acids Research, Aug. 1, 2008, vol. 36:14, pp. 4689-4698.

(Continued)

*Primary Examiner* — James Martinell
(74) *Attorney, Agent, or Firm* — MH2 Technology Law Group, LLP

(57) ABSTRACT

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumor. Accordingly, such methods have diagnostic, prognostic and/or predictive utility for detecting an increased risk of an individual suffering from or developing a medical condition such as preeclampsia or cancer, and/or to aid subsequent diagnostic, prognostic and/or predictive methods such as the detection of chromosomal trisomy in a foetus, including for twin-pregnancies. The present invention also relates to compositions, kits, computer program products and other aspects that are used in, useful for or related to the practice of such methods.

24 Claims, 3 Drawing Sheets

(56) References Cited

OTHER PUBLICATIONS

Sperling et al., "Twin pregnancy: the role of ultrasound in management", Acta Obstet Gynecol Scand, 2001, vol. 80, pp. 287-299.
Sorenson et al., "Soluble Normal and Mutated DNA Sequences from Single-Copy Genes in Human Blood", Cancer Epidemiology, Biomarkers & Prevention, Jan./Feb. 1994, vol. 3, pp. 67-71.
Vasioukhin et al., "Point mutations of the N-ras gene in the blood plasma DNA of patients with myelodysplastic syndrome or acute myelogenous leukaemia", British Journal of Haematology, 1994, vol. 86, pp. 774-779.
Lo et al., "Presence of fetal DNA in maternal plasma and serum", The Lancet, Aug. 16, 1997, vol. 350, pp. 485-487.
Muller et al., "Methylated DNA as a possible screening marker for neoplastic disease in several body fluids", Expert Rev. Mol. Diagn., 2003, vol. 3(4), pp. 443-458.
Lo et al., "Quantitative Analysis of the Bidirectional Fetomaternal Transfer of Nucleated Cells and Plasma DNA", Clinical Chemistry, 2000, vol. 46:9, pp. 1301-1309.
Smid et al., "Correlation of fetal DNA levels in maternal plasma with Doppler status in pathological pregnancies", Prenat. Diag, 2006, pp. 785-790.
Lo et al., "Rapid Clearance of Fetal DNA from Maternal Plasma", Am. J. Hum. Genet, 1999, vol. 64, pp. 218-224.
Kawai et al., "Methylation profiles of genomic DNA of mouse developmental brain detected by restriction landmark genomic scanning (RLGS) method", Nucleic Acids Research, 1993, vol. 21:24, pp. 5604-5608.
Masuzaki et al., "Detection of cell free placental DNA in maternal plasma: direct evidence from three cases of confined placental mosaicism", J. Med. Genet, 2004, vol. 41, pp. 289-292.
Flori et al., "Circulating cell-free fetal DNA in maternal serum appears to originate from cyto- and syncytio-trophoblastic cells. Case Report", Human Reproduction, Jan. 29, 2004, vol. 19:3, pp. 723-724.
Chim et al., "Detection of the placental epigenetic signature of the maspin gene in maternal plasma", Proc. Natl. Acad. Sci. USA, Oct. 11, 2005, vol. 102:41, pp. 14753-14758.
Chiu et al., "Hypermethylation of RASSF1A in Human and Rhesus Placentas", The American Journal of Pathology, Mar. 2007, vol. 170:3, pp. 941-950.
Old et al., "Candidate epigenetic biomarkders for non-invasive prenatal diagnosis of Down syndrome", Reproductive BioMedicine Online, Jun. 21, 2007, vol. 15:2, pp. 227-235.
Chim et al., "Systematic Search for Placental DNA-Methylation Markers on Chromosome 21: Toward a Maternal Plasma-Based Epigenetic Test for Fetal Trisomy 21", Clinical Chemistry, 2008, vol. 54:3, pp. 500-511.
Lo et al., "Prenatal Diagnosis of Fetal RhD Status by Molecular Analysis of Maternal Plasma", The New England Journal of Medicine, Dec. 10, 1998, vol. 339, pp. 1734-1738.
Go et al., "Non-invasive aneuploidy detection using free fetal DNA and RNA in maternal plasma: recent progress and future possibilities", Human Reproduction update, 2011, vol. 17:3, pp. 372-382.
Lo et al., "Quantitative Analysis of Fetal DNA in Maternal Plasma and Serum: Implications for Noninvasive Prenatal Diagnosis", Am. J. Hum. Genet., 1998, vol. 62, pp. 768-775.
Lo et al., "Quantitative Abnormalities of Fetal DNA in Maternal Serum in Preeclampsia", Clinical Chemistry, 1999, vol. 45:2, pp. 184-188.
Yu et al., "Quantification of Maternal Serum Cell-Free Fetal DNA in Early-Onset Preeclampsia", Int. J. Mol. Sci, Apr. 8, 2013, vol. 4, pp. 7571-7582.
Hahn et al., "Cell-Free Nucleic Acids as Potential Markers for Preeclampsia", Placenta, 2011, vol. 32, pp. S17-S20.
Li et al., "Hypermethylation of multiple tumor-related genes associated with DMNT3b upregulation served as a biomarker for early diagnosis of esophageal squamous cell carcinoma", Epigenetics, Mar. 2011, vol. 6:3, pp. 307-316.
Ha et al., "Elevated Levels of Cell-Free Circulating DNA in Patients with Acute Dengue Virus Infection", PLoS One, Oct. 7, 2011, vol. 6:10, e25969, pp. 1-7.
Outinen et al., "Plasma Cell-Free DNA Levels Are Elevated in Acute Puumula Hantavirus Infection", PLoS One, Feb. 7, 2012, vol. 7:2, e31455, pp. 1-7.
Forsblom et al., "High Cell-Free DNA Predicts Fatal Outcome among *Staphylococcus aureus* Bacteraemia Patients with Intensive Care Unit Treatment", PloS One, Feb. 10, 2014, vol. 9:2, e87741, pp. 1-9.
Chan et al., "Size Distributions of Maternal and Fetal DNA in Maternal Plasma", Clinical Chemistry, 2004, vol. 50:1, pp. 88-92.
Kimura et al., "Fragment Size Analysis of Free Fetal DNA in Maternal Plasma Using Y-STR Loci and SRY Gene Amplification", Nagoya J. Med. Sci., 2011, vol. 73, pp. 129-135.
Lo et al., "Maternal Plasma DNA Sequencing Reveals the Genome-Wide Genetic and Mutational Profile of the Fetus", Science Translational Medicine, Dec. 8, 2010, vol. 2:61, 61ra91 pp. 1-14.
Elshimali et al., "The Clinical Utilization of Circulating Cell Free DNA (CCFDNA) in Blood of Cancer Patients", International Journal of Molecular Sciences, 2013, vol. 14, pp. 18925-18958.
Sacha Zeerleder, "The struggle to detect circulating DNA", Critical Care, 2006, vol. 10:142, pp. 1-3.
Kirsch et al., "An Improved Method for the Isolation of Free-Circulating Plasma DNA and Cell-Free DNA from Other Body Fluids", Ann. N.Y. Acad. Sci., 2008, vol. 1137, pp. 135-139.
Struble et al., "Fetal Fraction Estimate in Twin Pregnancies Using Directed Cell-Free DNA Analysis", Fetal Diagnosis and Therapy, Dec. 7, 2013, pp. 1-5.
Gauthier et al., "Blood Clearance Kinetics and Liver Uptake of Mononucleosomes in Mice", The Journal of Immunology, 1996, vol. 156, pp. 1151-1156.
Lo et al., "Quantitative Analysis of Aberrant p16 Methylation Using Real-Time Quantitative Methylation-specific Polymerase Chain Reaction", Cancer Research, Aug. 15, 1999, vol. 59, pp. 3899-3903.
Birch et al., "Accurate and Robust Quantification of Circulating Fetal and Total DNA in Maternal Plasma from 5-41 Weeks of Gestation", Clinical Chemistry, 2005, vol. 51:2, pp. 312-320.
Papageorgiou et al., "Fetal-specific DNA methylation ratio permits non-invasive prenatal diagnosis of trisomy 21", Nat. Med., Apr. 7, 2011, vol. 17:4, pp. 1-13.
Tong et al., "Technical concerns about immunoprecipitation of methylated fetal DNA for noninvasive trisomy 21 diagnosis", Nature Medicine, Sep. 2012, vol. 18:9, pp. 1327-1328.
Hindson et al., "High-Throughput Droplet Digital PCR System for Absolute Quantitation of DNA Copy Number", Anal. Chem., 2011, vol. 83, pp. 8604-8610.
White et al., "Evaluation of a Novel Assay for Detection of the Fetal Marker RASSF1A: Facilitating Improved Diagnostic Reliability of Noninvasive Prenatal Diagnosis", PLoS One, Sep. 14, 2012, vol. 7:9, e45073 pp. 1-5.
Qu et al., "Noninvasive Prenatal Determination of Twin Zygosity by Maternal Plasma DNA Analysis", Clinical Chemistry, 2013, vol. 59:2, pp. 427-435.
Lim et al., "Disease specific characteristics of fetal epigenetic markers for non-invasive prenatal testing of trisomy 21", BMC Medical Genomics, 2014, vol. 7:1, pp. 1-11.
Poon et al., "Differential DNA Methylation between Fetus and Mother as a Strategy for Detecting Fetal DNA in Maternal Plasma", Clinical Chemistry, 2002, vol. 48:1, pp. 35-41.
Yegnasubramanian et al., "Combination of methylated-DNA precipitation and methylation-sensitive restriction enzymes (COMPARE-MS) for the rapid, sensitive and quantitative detection of DNA methylation", Nucleic Acids Research, 2006, vol. 34:3, e19 pp. 1-14.
Papantoniou et al., "RASSF1A in maternal plasma as a molecular marker of preeclampsia", Prenatal Diagnosis, 2013, vol. 33, pp. 682-687.
Zeybek et al., "Clinical evaluations of cell-free fetal DNA quantities in pre-eclamptic pregnancies", J. Obstet Gynaecol Res., Mar. 2013, vol. 39:3, pp. 632-640.

(56) References Cited

OTHER PUBLICATIONS

Jakobsen et al., "Identifying mild and severe preeclampsia in asymptomatic pregnant women by levels of cell-free fetal DNA", Transfusion, Sep. 2013, vol. 53, pp. 1956-1964.
Chen et al., "Chimerism in Monochorionic Dizygotic Twins: Case Study and Review", Am. J. Med. Genet. Part A, May 22, 2013, vol. 161A, pp. 1817-1824.
Chan et al., "Hypermethylated RASSF1A in Maternal Plasma: A Universal Fetal DNA Marker that Improves the Reliability of Noninvasive Prenatal Diagnosis", Clinical Chemistry, 2006, vol. 52:12, pp. 2211-2218.
Stumm et al., "Diagnostice accuracy of random massively parallel sequencing for non-invasive prenatal detection of common autosomal aneuploidies: a collaborative study in Europe", Prenatal Diagnosis, 2014, vol. 34, pp. 185-191.
Leung et al., "Noninvasive twin zygosity assessment and aneuploidy detection by maternal plasma DNA sequencing", Prenatal Diagnosis, 2013, vol. 33, pp. 675-681.
Tong et al., "Noninvasive Prenatal Detection of Fetal Trisomy 18 by Epigenetic Allelic Ratio Analysis in Maternal Plasma: Theoretical and Empirical Considerations", Clinical Chemistry, 2006, vol. 52, No. 12, pp. 2194-2202.
Papageorgiou et al., "Sites of Differential DNA Methylation between Placenta and Peripheral Blood", The American Journal of Pathology, May 2009, vol. 174, No. 5, pp. 1609-1618.

\* cited by examiner

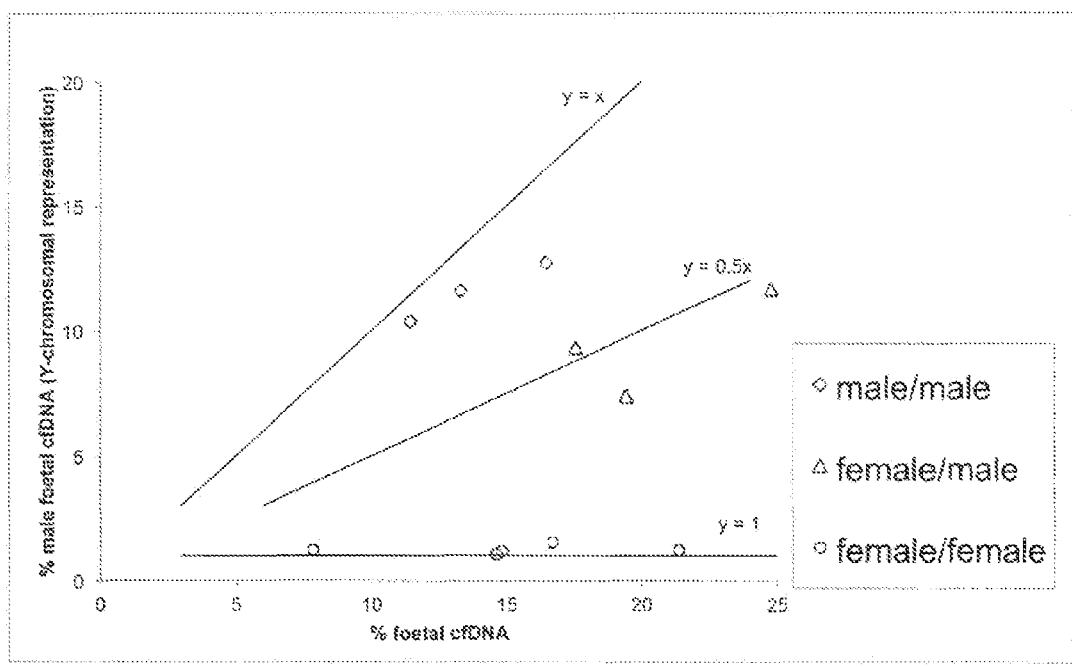
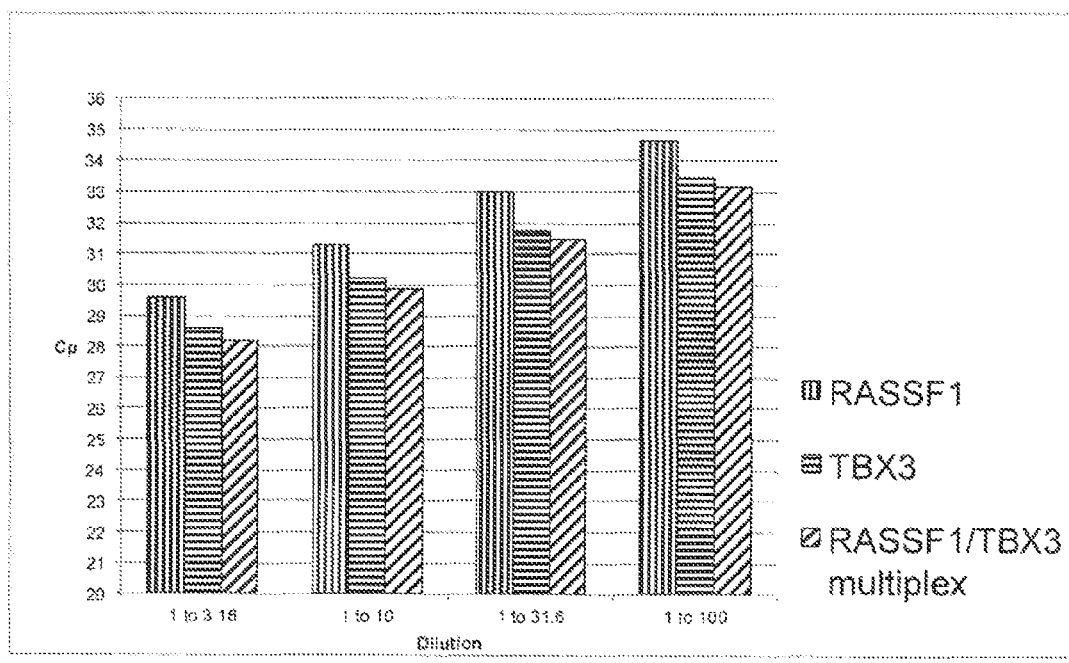

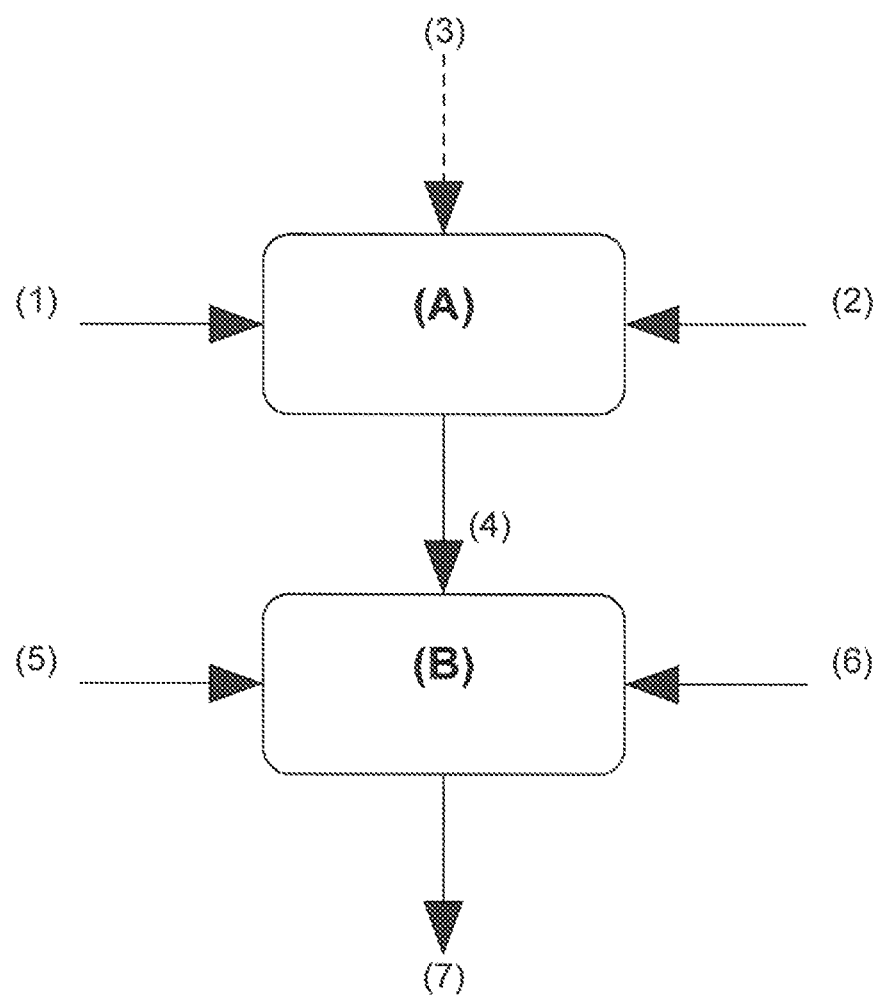

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
attgagctgc gggagctggc                                            20

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tgccgtgtgg ggttgcac                                                18

<210> SEQ ID NO 3
<211> LENGTH: 15
<212> TYPE: DNA
<213> ORGANISM: Artificial Sequence
<220> FEATURE:
<223> OTHER INFORMATION: probe

<400> SEQUENCE: 3
acccggctgg agcgt                                                   15

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtcatccac caccaagaac                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tgcccaagga tgctgtcaag                                              20

<210> SEQ ID NO 6
<211> LENGTH: 20
<212> TYPE: DNA
<213> ORGANISM: Artificial Sequence
<220> FEATURE:
<223> OTHER INFORMATION: probe

<400> SEQUENCE: 6
gggcctcaat gacttcacgt                                              20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggtgcgaact cctctttgtc                                              20

<210> SEQ ID NO 8
<211> LENGTH: 20
<212> TYPE: DNA
<213> ORGANISM: Artificial Sequence
<220> FEATURE:
<223> OTHER INFORMATION: primer

```
<400> SEQUENCE: 8
ttaatcaccc agcgcatggc                                              20

<210> SEQ ID NO 9
<211> LENGTH: 20
<212> TYPE: DNA
<213> ORGANISM: Artificial Sequence
<220> FEATURE:
<223> OTHER INFORMATION: probe

<400> SEQUENCE: 9
ccctcccggt gggtgataaa                                              20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgttcactgg aggactcatc                                              20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
cagtccatga gggtgtttg                                               19

<210> SEQ ID NO 12
<211> LENGTH: 18
<212> TYPE: DNA
<213> ORGANISM: Artificial Sequence
<220> FEATURE:
<223> OTHER INFORMATION: probe

<400> SEQUENCE: 12
gaggtcccat tctccttt                                                18

<210> SEQ ID NO 13
<211> LENGTH: 18151
<212> TYPE: DNA
<213> ORGANISM: Homo sapiens
<220> FEATURE:
<223> OTHER INFORMATION: RASSF1

<400> SEQUENCE: 13
gacttggcgt ctgaggacag agtccagacc acaaggatct ggagctcagg agagactcgt    60
gggccacagc ccgagaaagc gctgggaatc caaatactat ggcgattggc agtcgcgtag   120
gcgaggcggg ctagagaccc gcccggattt aggcgcgagc cacctccagg ggcggggccc   180
aggccgcact gcgcaggcgc ggctaaaccg tttccatggc tgcgagaact gacgctcccc   240
aaccgtcccg caactgtcct gtcccagact ttggcaccgt cggggtccgt cgtcccgaa    300 tgtgacagca tccccacccc ggctgctgcc caggatccgc cggaccccgg cctcgatatg   360
ggagacctgg aactgctgct gcccggggaa gctgaagtgc tggtgcgggg tctgcgcagc   420
ttcccgctac gcgagatggg ctccgaaggg tgaggcaccc gggtcaggcg gagtcccgga   480
gtcattgtcc ttgagtcggg gagctggggc ctgactcggg ggaggggctg cccagtgtgg   540
```

```
agggggctccc aaatggggga gcagagcgtt ccgagacagg agtattactg ctcctgagcc      600
ccctgtgtcc cctcaggatc aggttaggct tcagtaggat ccagccccca tccccactcc      660
taatgcacac acgtggacgc acatgcactt accctctgag gcaggtggaa ccagcagcat      720
gagaacctgg agaagctgaa catgcaagcc atcctcgatg ccacagtcag ccagggcgag      780
cccattcagg agctgctggt cacccatggg aaggtacccc gaggtcacag gcagggttcc      840
tgccttcccc catacctcac ctactctacc cctccggagt cccctgtgtg cccttcccct      900
ctggcctggt acacctgttc tccctgaagg acaaagagga atgtgttaca tgtttcattt      960
tgtatcccta ttggacagga ctctggcaca ccaggctggg tgcagggcat gagttgatta     1020
gggagaaagc tgtaggtcct agaacagctt aggcttcaag gggaaggccc aaatgctaaa     1080
ggcatctgtg aattgactgt aaggctggtg gtggggaagg ggtggggagg ggttggggag     1140
ggcgggaggg aggggagata acctaactgg aagtggaact tcggcatgga aggaagcagc     1200
cttcccaaca tgaaagggg aagttagaaa ccagggagat gcctggctgg aacatggacc     1260
agggagtgtc accagcagat gacctgagat atcaattgac caaaaaaaaa aaaaaaaag     1320
ccgggcatgg tagctcatgc ctgttatccc agcattttgg gaggccaaga cgggtggatc     1380
atctgaggtc aggagttcaa ggccagcctg gccaacatgg tgaaacccca cctctactaa     1440
aaatacaaaa atttgcagag catggtggtg cacacctgta atcccagcta ctcgggaggc     1500
tgaggcagga gaatcgcttg aacctgggag gcagaggtta cagagagcca agatcatgcc     1560
actgcactcc agcctgggtg acaagagtga aactccgtct caaaaaaaaa aaaaaaaaa     1620
agaaaggtcc tttgcaaaag aaagatggaa ctcatactag gggataggat aggaacaggg     1680
cactgtgaag ggtcctgagt aggagtgagg ccaaggcaca caagagcttt ggaggaccac     1740
agacagggac tagaggagg gcatgaggag aagggctggc ttgaaaggga tgcctgaatg     1800
ggcgggcaga ggataagggt gcaggtcag gcagggcaag gcagtctggg aactgggcag     1860
gagccagtca cataagcatg agggacatcc acagaggtgt gggagcagc tggtaatgaa     1920
ggtccaaggt gcaagagaga agtcaggaag gatactcatg ggtctggaat agtttagggg     1980
cccagcagtg tttggggata tcagggttga gctgagccgg ggatgggagg gttgccaggc     2040
aaaggtaggc ccatctcatc cctgtccttt accctaccct tcaaaggtcc caacactggt     2100
ggaggagctg atcgcagtgg agatgtgaa gcagaaggtg ttccctgtgt tctgcagggt     2160
ggaggacttc aagccccaga acaccttccc catctacatg gtggtgagct gggcccctgg     2220
ttcataccte ttctcactcc ttcagagggc tctggaccgg ggaggagagc tggtagcccc     2280
tatcccttcc tcaggccctg tccttctctt tatctgacag gtgcaccacg aggcctccat     2340
catcaacctc ttggagacag tgttcttcca caaggtgagg gactatctct gcccatgggc     2400
cacagttccg ggtcagggcc tggcaggaag ggagattgtg tctgtgtggg gaaggcatca     2460
gacacagaaa gtttccctcc tccttttccc aggaggtgtg tgagtcagca gaagacactg     2520
tcttggactt ggtagactat tgccaccgca aactgaccct gctggtggcc cagagtggct     2580
gtggtggccc ccctgagggg gagggatccc aggacagcaa ccccatgcag gtgggttgag     2640
gttacctagg gttgtgaaag cctaggtctg ggttccccaa ggcctgcgca ggtgagggtg     2700
gcccagcgtg aacactgtgt gacctcccag gagctgcaga agcaggcaga gctgatggaa     2760
tttgagattg cactgaaggc cctctcagta ctacgctaca tcacagactg tgtggacagg     2820
tgagcagtcc gactgggcct gggcctactg tggagggctg gaagaccggg cctgtagcct     2880
```

```
gcctctactc acctccttca caacgtccct gccccctagcc tctctctcag caccttgagc    2940
cgtatgctta gcacacacaa cctgccctgc ctcctggtgg aactgctgga gcatagtccc    3000
tggagccggc gggaaggagg tagggtcctc ccccaccagc ctaagcccca ggctactgct    3060
tcagggtatc tttttgatag agggggggcag cttgcacaca cgaagacaaa ccctgtcccc    3120
aagcccactg aggataccag gatgcctcag ccaaggttgg cctagacctg agctctgcag    3180
caggccaggc ccatgtgtcc actactgagg ctcaccctgc tctggggtca gcagccctat    3240
agcctgggca agtcctgcag cccaggttct cccattccca ggcagtggtc agtctcccag    3300
cccccacagc tggctcactt gaagagaatt caacgtctgc acccagtgtg ctggttcctc    3360
tccccaggca agctgcagca gttcgagggc agccgttggc atactgtggc cccctcagag    3420
cagcaaaagc tgagcaagtt ggacgggcaa gtgtggatcg ccctgtacaa cctgctgcta    3480
agccctgagg ctcaggcgcg ctactgcctc acaagttttg ccaagggacg gctactcaag    3540
gtcagactcc ctccgcacca gccccacag ccccagtacc gccctcccca tcctaccccg    3600
actgcgtccc tgctgtttat ctttgcccac ccacctcaac cccagtgctc ttttcagtcc    3660
ttgggcctca ggtgacacac cagctagtgg gacatgggcc cccacaggca ttctcagccc    3720
aacccagccc cttcctttc cttggccccc tggccagcac ctgcatcaca ctggcctcca    3780
ctggacaccc ttgcagcttc gggccttcct cacagacaca ctgctggacc agctgcccaa    3840
cctgccccac ttgcagagtt tcctggccca tctgacccta actgaaaccc agcctcctaa    3900
gaaggacctg gtgttggaac aggtaggcac tggaaagtta gctgctcagg accactgtcc    3960
cactttacca gcaccttcct gccactctcc acttctctct cctagatccc agaaatctgg    4020
gagcggctgg agcgagaaaa cagaggcaag tggcaggcaa ttgccaagca ccagctccag    4080
catgtgttca gcccctcaga gcaggacctg cggctgcagg cgcgaaggta aggcctgtgg    4140
aaatggcagg gagggtggag gggatgcagg aggcatggat gtgggtgggg tgccccacc    4200 ttccagggcc agtcagacct tcctgacttt cccccaggtg ggctgagacc tacaggctgg    4260
atgtgctaga ggcagtggct ccagagcggc cccgctgtgc ttactgcagt gcagaggctt    4320
ctaagcgctg ctcacgatgc cagaatgagt ggtattgctg caggtgaggg tatcctagaa    4380
ccttggacct ctaagcccta ctcccacatc ccccacatgc attgccatcc tcaatacccca    4440 cctgcctgca gggagtgcca agtcaagcac tgggaaaagc atggaaagac ttgtgtcctg    4500
gcagcccagg gtgacagagc caaatgaggg ctgcagttgc tgagggccga ccacccatgc    4560
caagggaatc cacccagaat gcaccccctga acctcaagat cacggtccag cctctgccgg    4620
agccccagtc tccgcagtgg agagcagagc gggcggtaaa gctgctgacc gatctccctc    4680
ctcctcaccc caagtgaagg ctcgagactt cctgccccac ccagtgggta ggccaagtgt    4740
gttgcttcag caaaccggac caggagggcc agggccggat gtgggaccc tcttcctcta    4800 gcacagtaaa gctggcctcc agaaaacacgg gtatctccgc gtggtgcttt gcggtcgccg    4860
tcgttgtggc cgtccggggt ggggtgtgag gaggggacga aggagggaag gaagggcaag    4920 gcggggggg ctctgcgaga gcgcgcccag ccccgccttc gggccccaca gtccctgcac    4980
ccaggtttcc attgcgcggc tctcctcagc tccttcccgc cgcccagtct ggatcctggg    5040
ggaggcgctg aagtcggggc ccgccctgtg gcccgcccg gccgcgcgtt gctagcgccc    5100
aaagccagcg aagcacgggc ccaaccgggc catgtcgggg gagcctgagc tcattgagct    5160
gcgggagctg gcaccgcctg ggcgcgctgg gaagggccgc acccgctgg agcgtgccaa    5220 cgcgctgcgc atcgcgcggg gcaccgcgtg caaccccaca cggcagctgg tccctggccg    5280
```

-continued

```
tggccaccgc ttccagcccg cggggcccgc cacgcacacg tggtgcgacc tctgtggcga    5340
cttcatctgg ggcgtcgtgc gcaaaggcct gcagtgcgcg cgtgagtagt ggccccgcgc    5400
gcctacgaga gcggaagggg cagccaaggg gcagcgcagt cgccgcgggt caagtcgcgg    5460
cagagggggt cggcggggac agctcccgag gactaggtcc gttactttcg ccccatcgct    5520
gaagagtgcg cgaaaatggt ttatcccttg tcgcactcca ctcgtatctg ggccacagat    5580
gagcagaggt ggctgcttat atgtaaaaat acgctgattt taagtttctt atctttaaaa    5640
tgccttggcc cttcttgaga aagggtttgt gcctactgtc ctcggagtcc atcttcccag    5700
gcttgcctct tctcaaacac tcatgacccc ctccagaacc tttagggtga agggaaatta    5760
ccacctatgg gagggagcct ggaaaaattt agaacctttg gtgggccccc tgcaagcagg    5820
agttttgttg agtctttatt tagcaaacac ccttttctga cccagtgaat cagatgctaa    5880
aatatgcacg cagccacaca cccagcagtc cttctgcacc cctgggaatc gccagcaagc    5940
aaaggttgct ctcccctggg tagacaccag ctggaatcac caggggtgct tttacagtcc    6000
tccccgctag cctggatccc accgcagacc tgttgaatca actgctggga gtggaccta    6060 ggcatcagta aattttaaaa actccccaaa ttattgtaac atggagtctg ggttgagcat    6120
cactgctctg gcctatttag gaacttgtgg atggatagtg tcccaggtct gtgtgtgcat    6180
ggagaccctc tcatccggta caagaggaca tcacaaattc agctgggggg agcacaaagt    6240
tgtgacagaa tgcaaagaat gaacaagggg ccgagcgcgg tggctcatgc ctgtaatccc    6300
agcacttcgg aaggcggagg cgggtggatc acctgaggtc aggagttcaa gaccagcctg    6360
gccaacatgg tgaaacctca tgtctactaa aaaataaaaa aaaatgagcc aggcgtagtg    6420
gcgggtgcct gtaatcccag ctactcggga ggctgaggtg ggagaattgc ttgaacacag    6480
gaggcggagg ttgcagtgag ccgagatcgt gccactgccc tccagccttg gcgacagagt    6540
gagactctgt ctcaaaaaaa aaaaaaaaa aaaaagaac aaggctggga cattgcagcg    6600
ttctcaaaga gaaataaagt agccatggag ataagaagca ggatgatttg gcatgtttta    6660
tcagaggtag agacaaggga gaaatcaaag ataagtttgg gcttttgtct ccagtaactg    6720
ggagcctagt ggccattttt gctgcaaaga ggaagctggg caagtgtagc agtgaggctg    6780
aagaaaaggg aattaaattt tggccatgtt cacttgaaac gtcttttaga catcctagtg    6840
aaggtactgg cacggaggat ctagtctgag ggtttaggtc agtgtttcag ccgtggatct    6900
ggggcagatg aatgtagaca gaccaggcca gtgatcagga ctgagcccag acttcatcgt    6960
gagatatgga agttgagtca gaatctgcaa aggagctgag caggagctgc aggggtagg    7020 aggaaaactg ggagagtgta gcccctggga gtcaaaggga gcaagcttca aatgatgctg    7080
agggggtgag aatggagaat ggaacactgg attccatttg gtagtacaca gatcgctgag    7140
gaccctgtcc cggcagtttt cctggaggaa gaggcaagcc tggctggagt gggtagaggg    7200
gagagtgaag gcgaaggatt agagtgtata gagaccagtg tcttggtctg aggggagtag    7260
agacaggtga caaccacagg gcagacgtag gttaaaggtg tttagttttt ccttcaagta    7320
aatgggcaga tgtattccat atacgttccc agtgaagggc cgggtgcggt ggctcaagcc    7380
tgtagtccca gcactttgga aggccgaggc gggtggatca cctgagatca ggagtttgag    7440
accagcctgg ctaacatggt gaaacccgt ctctactaaa aatacaaaaa ttagctgggc    7500
atggtggcgg gcgcctgtaa tcctaggtac tcaggaggct gaggcagaag aatcgcttga    7560
acccaggagg cggaggttgc ggtgagccga atcgcgcca ttgcactcca gcctgggtga    7620
```

```
caaaagcaag acgcagttttt ttgttgttgt tttttttaatt gccaatgagg aaaggggaag    7680
ttctgtgcta ggcgatagag atccaactgt tgagcaggcc tctctgcctg tggccttccg    7740
gccggtttcc agacgcccag gtggccaaca ttagagtccg cgtagcagtg tgaggtaacc    7800
cactgagata ggtcgggcct gcggagcctg gcgagcagcg gccctctccc tggggcttcc    7860
cttcaatctc cgggacattt ccccgacctg gagctcctcc gcctcaccgc caggcctctc    7920
tgcagattgc aagttcacct gccactaccg ctgccgcgcg ctcgtctgcc tggactgttg    7980
cgggccccgg gacctgggct gggaacccgc ggtggagcgg gacacgaacg tggtgagcgc    8040
ggggccgagg gcgtatggga agggcgagga tgggcaggcc acagtgcagg cattctcgag    8100
ggctgcctgg gtgccgcgcg caaggagcgt tctaattgcc gatttcccgg cggcacagag    8160
aggctaattc tgcgcggggg ctgggagggg agcctggatt gccggctccg caagtactcc    8220
acccgctgca agcggacccg ggcccaggct gacccaggct ccgcgcacgc gcacttcccg    8280
caccttcccg ccctcgcctc cggccagagg ccactcttgt gcgcttgccc ggacgctggc    8340
acccgccccc gttccctgtg gtaggtgggg tctgtgagtg gagctccgga gcgatgaggt    8400
cattcctggg ggcgaagcgt gcgtgtcccc gccccggcgt tcctgcccca atgagacaag    8460
agctagatcc cggcgatcta cgtttcagtc ttaacggttg cggcgcggct ctggcccggg    8520
cgcacgcgca cactgacacg cgtacacgca cgcacgcgac cggggcggtg gttggcggct    8580
acggacgcgc aggactgggg gacgggcggg tacggctatg ggcgaggcgg aggcgccttc    8640
tttcgaaatg acctggagca gcacgacgag cagtggctac tgcagccaag aggactcgga    8700
ctcggagctc gagcagtact tcaccgcgcg aacctcgcta gctcgcaggc cgcgccggga    8760
ccaggtggga gccaggggt gccggcgggc gggaggggaa gcggtcgctg gagctccgcc    8820
ctccccggtc cgttgccgcg tcctgggtcg gtgggcagcc ccaccctcct ggctacgtgg    8880
ctccccgcgg gtcctggccg gggacctgcc cgcggaaccg tgcgtaagac cccgattcca    8940
ccgcctagat gctgggtgcc ggggccccct tggtttctgt cacagacagg ttgaacacgg    9000
aaaaagcagc tgtatggctt gtggtagacc tgagccgggc attatccagc tatgactaaa    9060
gccgaccgag cagtttggac tagcacctcg atttccgcgt tcgaatgctc ctgctccctc    9120
cttggggaga ctaggggagg atgtggagag gaagagtcc tcgccaggaa ttgagaagta    9180
tgtttaggaa aacttgagag gcagagagag atcctgctcc tccatctgca ctcctgtatg    9240
gagccagctg agccctcacc tcttccctgt tctggcctgt caccagctgc tggaatgtgg    9300
aagattctgt tcccttcctc tagggtggat ctggagaaag atttgggaat agataggaaa    9360
gaagtcttgt tttggaccat aagcattcag gagcacttta cccacaggaa gggggaaagc    9420
tagattataa aatgcctaaa gaggtggaaa aagagatcca ggttactaac ccaggactgt    9480
aaggtgtctc ggaacctcct aggtatcccc attatcggag aactgtgtgc cagatgccat    9540
tggtgtgacc accaggctca gagaaccagg cctaggcacc aggaaaaaga aacagggact    9600
gtgaagctca gtatgcctgg cagaaatggg gcggaaatcc ttatttaagt aaagaaagtg    9660
gagttgtgag tgatgcttca gataaaattt tacaaaattc cttacaaaat gggtggtgct    9720
cagcacgcca aaatcttagc ccagagcttg gtgcaagggt tgagttgag tgtagacccc    9780 tgggcttgtc ttcatgtcag tcagtcctga gccatttcc actgtggaaa ggtgggaaaa    9840
ccacaagaca ctaaccaatt gaaaaggagg gctagccacg gaggtgcaca cctgtaatcc    9900
cagctacttg ggagggtgag gcagaaggat cacttgaacc tgggaggcag aggttgcagt    9960
gagccaagat cgtgccactg cactccagcc tgagtgacag agtgagactc tgtctcaaaa   10020
```

```
atagaaaagg aagccaagta cggtggctca cacctctaat gccaatgctt tgggaggcca    10080
aggcaggtgg atcatttgca atcaggaatt cgaggtcagc ctggccaaca tggtgaaacc    10140
ctatctctac taaacataca aaaattagcc gggcatggtg gtgtgtgact gtagtcccag    10200
ctacttggga gactgaatca cttcaaccgg gaggcaaagg ttgcagtgag ccaagatcgt    10260
gccactgcac tccaacctgg gtgacagggt gaggctctgt ctcaaaaaaa agaaagaagg    10320
ctgggcttgg tgactcatgc ctgtaatctc agcattttgg gaggccaagg caggcagatc    10380
acttgaggcc aagagttcga gacctgccag gccaacatag caaaaccccg tctgtactga    10440
aaatacaaaa aaattatctg gccatggtgg tgtgtgcctg taatcccagc tactgggag    10500
gctgaggcag gagtatcact tgaacccaga agacagaggt tgcagtgagt cgagactggg    10560
ccactgcatt ccagcctgga tgagagagca agactctgtc tcaaaaaaaa aaaaaaaaa    10620
aaagaaagaa taggaggctg agaagtccca agttatatgt taaaaaaaaa gaaaaaaaca    10680
tcagttttag gccaggtgca gtggctcaca ccttttaatcc cagcactttg gaaagccgag    10740
gtgggtggat catgaggtca ggagttcaag accagcctgg ccaaaatggt gaaacccgt    10800
ctcgactaaa aatacaaaaa attagccagt tgtggtggca ggcacctgta atcccagcta    10860
cttgggaggc tgaagcagag aattgcttga acccaggagg cagagattgc aatgagccaa    10920
gatcgcacca ctgcactcca gcctggaaaa cagagcgaga ctctgtctca aaaaaaaac    10980
catcagtttt tatggacagt ggtagagtgg agggtgggtc cctatggtgc agaagggaaa    11040
ttccatggtc ctgctgtgca tccgactggg atggctgttg aaatcctctt ccagcaggca    11100
gctttggaaa cagaaaaaga aactcttcct cctttagaat cctggaaggg ctgtgcagtg    11160
cctctaatcc aagtctgttt tctgagtgaa gatagggagg ttcatcacca gaagggaagg    11220
ggctggaaat gaggtcactg catcccagcc cagggctcct gggtcatcca ggaagggaag    11280
aaggagcaag ctttctcatt gttaggtagg agctcagagc catcacaaga acaagttagc    11340
accatccctg tgccctccct gttctgcaaa caaaatgatc ttccttcttg ccctggcact    11400
agagtctgtc tggcatttct cctgcccta gtactcctcc catctgggta cttcttcccg    11460
ttggtgtact gaacaaacac atccactgct ttattcacag cctccagccc tcattttcca    11520
gggcccacac catttgtttt tactaacccg acaaggttgc ccactgtccc cagtaaggtt    11580
tgtactgggg ttttttactcc agtgctcttc tccatccagg agaccttttgg atacttgggg    11640
aagaaaatga gcttaaattc ccaccccctcc cccttacct ttttcctgta aggccctggc    11700
cttagttctt agcccccacat ccttgctggc tgcagaatag cagcgggttc tgggtaagga    11760
gcattctgct aaaacgctcc accctgctcc ctcatctgtc ctctccattt gtccccatca    11820
gatggtttaa gtgcttaagg ggactccagg gcggagtcag ggagaaccct ggctctcctg    11880
ggctaggcac aagatcattc tacaggaaac cttgtgggaa ttcttctggg acaaagtatt    11940
ggtcagcgct gagcttagct gtgtctgtga cactcgcatt ctaactaggg cctatctgac    12000
gtcaacagga agtaaggctg atgcagtggg gccaaggag tctgggagaa gaaagtcggt    12060
tcagagccct ggctgccctg tcccacactc cacccttccg gcaagaatcc agtccctaga    12120
tgaggtgggg agtgagtggt cgagttaaaa atctctgggt cgggtacgat ggttcacgcc    12180
tgtaatccca gcactttggg aggtgaaggc aggcggatca cttgaggtca ggagttcaag    12240
accaacctgg ccaatgtggt gaaatcccat ctctactaaa aatacaaaaa ttagccgggt    12300
gttgttgtgg cacgcgcctg tagtcccagc tactcggag tctgaggcag gagaatcgct    12360
```

```
tgaacccagg aggcagaact tgcagtgagc caagatccag ccactgcact acagcctggg    12420
cgacagagtg aggcttcgtc tcaaaaaaaa aaaaaatctt tgggccaaat ctccagacag    12480
cacaggcagg tgcagaaacc caccaggaag ctgcctgtgt acctctggca gattggagcc    12540
tggcctaaag ctgccttta tgcagcttgg gtcaaggtta aacatcatgt cacagtgatt    12600
tttctcacta tgtgtgagac atggagaact ggctccaagt actactctgt ccactggtgg    12660
ctggactact gatgtgcacc actctccact cctctcaccc tgcagtgggt catgccccg    12720 tgccggggca gaggagaaaa atgggctgcc ttctccagga caaaccctca ctccaactca    12780
actagggtgc tgtgatcaga atgtgcaatt gaggtgtgat tttactgatt ttttttttt    12840 ttgagaccga gtttcgctct tgttgcccag gctggagtgc gatggcacga tctcagttca    12900
ctgcaacctc cacctcccga gtttgagcaa ttctcctgcc tcagcctcct aagtagctgg    12960
gattacaggc atgtgccacc acgcctggct aattttgtat ttttagtaga cggggttt    13020 ctccatgttg gtcaggctgg tctcaaactc ctgacctcag gtgatccacc cgcctcggcc    13080
tcccaaagtg ctagaattac aggcgtgagc caacgtgccc agcctgtttt tgttttttgt    13140
gttttgaagc agggtctcac tcagttcccc aggctggagt gcagtgacac gataatagct    13200
tactgtagct gcaatctccc gggctcaaac gatcctccca cctcagcctc ctgaacagtt    13260
gggactacag gcacaccacc acacctggct aattttttt tttctttttt tagtagagat    13320
gaggtcttgc tatgttgccc aagctggtct caaactcctg aggatcaagt gatcctccta    13380
ccttagcctc ccaaaatgct gggattgcag atgtgagcca ccacacccag cctgattta    13440 ctttaaatga gagtccctct tcagagtccc tcagctgttc ctggcccctg gccatgtgcc    13500
ttcagttgcc cctgcttctg tggtatcctt aaggctacat tcagtgctga ggccctaggc    13560
aggcagcaga gagaagccaa atgattctgt ctttccctta tccacccaga gcatgcaaaa    13620
ccaggagcag tggtgggttc agggtgggca ccagctatgt atatgtacat cagggacagg    13680 gggcaaagg cagtcagttt ccaaagactg ccccagaggc cattttcag agaagccctg    13740 ggttcctcaa gggccctgtg tccatgctgg cccatcttgc aggacgagcc tgtggagtgg    13800
gagacacctg acctttctca agctgagatt gagcagaaga tcaaggagta caatgcccag    13860
atcaacagca acctcttcat gagcttggtg agttgactgc tcaggaaggg ggcgtgggga    13920
ggagcaggta cccagctatg tgcctgatac tcagagggtc acaactgagg ttatcttggg    13980
tgggcgcaag cagtaatttg tgcatacccca gcctagcccc aagtagactg acatctcacc    14040
tggaacctat tatcaaggtt tggtttctct atttctttag aacaaggacg gttcttacac    14100
aggcttcatc aaggttcagc tgaagctggt gcgccctgtc tctgtgccct ccagcaagaa    14160 gccacccctcc ttgcaggatg cccggcgggg cccaggacgg ggcacaagtg tcaggcgccg    14220
cacttccttt tacctgccca aggatgctgt caagcacctg catgtgctgt cacgcacaag    14280
ggcacgtgaa gtcattgagg ccctgctgcg aaagttcttg gtggtggatg accccgcaa    14340 gtttgcactc tttgagcgcg ctgagcgtca cggccaaggt gggcttccca ccccaccctg    14400
ccctatgtga gggtatatac gcatgcacct gagcatgcag gggctgagca gctggccctg    14460
tctctgatca ttacttcccc ttcacagtgt acttgcggaa ctgttggat gatgagcagc    14520 ccctgcggct gcggctcctg gcagggccca gtgacaaggc cctgagcttt gtcctgaagg    14580
aaaatgactc tggggaggtg aacgtgagta catagttctt agtttcttgg ttgtcactag    14640
acaggactga tgggctgtag ctacagtaag gcttggagga ggaattgtgc tggaagacaa    14700
gccctgcaaa acagttccag gagtgtatag gcattgtaac taaagcaaag gcttccagac    14760
```

```
cactcatgcc aaagcctagg gttgtcccaa gaagccagga agaattgcct tggtgctttg   14820
atctttcctg gtgtggaaaa tcttctggag atgcaggagt ccatctaatg acatgaggag   14880
gcccccttca gacttttttac ctggaagctt tctggctcca aggtattagg cctgtggagt   14940
gaaattagac tcagaatatg cctgacctgt ccacaggtaa ttggggaaca tctgacttgg   15000
ttgtctcagt aaggtgaccg ttttgtaggg cccatcttcc atacaaactg ctgtcaggga   15060
tcctaccaga gatcattcag ccaagagcct gacatcagaa agcccagtcc tagcttgtgt   15120
gaacatgagg tgctagtctt ctctggggag ggtctgctgg cttggccatc ccttctgcag   15180
cctgtacact ccccttttgc cccttgcagt gggacgcctt cagcatgcct gaactacata   15240
acttcctacg tatcctgcag cgggaggagg aggagcacct ccgccagatc ctgcagaagt   15300
actcctattg ccgccagaag atccaagagg ccctgcacgc ctgccccctt gggtgacctc   15360 ttgtacccccc aggtggaagg cagacagcag gcagcgccaa gtgcgtgccg tgtgagtgtg   15420
acagggccag tggggcctgt ggaatgagtg tgcatggagg ccctcctgtg ctgggggaat   15480
gagcccagag aacagcgaag tagcttgctc cctgtgtcca cctgtgggtg tagccaggta   15540
tggctctgca cccctctgcc ctcattactg ggccttagtg ggccagggct gccctgagaa   15600
gctgctccag gcctgcagca ggagtggtgc agacagaagt ctcctcaatt tttgtctcag   15660
aagtgaaaat cttggagacc ctgcaaacag aacagggtca tgtttgcagg ggtgacggcc   15720
ctcatctatg aggaaaggtt ttggatcttg aatgtggtct caggatatcc ttatcagagc   15780
taagggtggg tgctcagaat aaggcaggca ttgaggaaga gtcttggttt ctctctacag   15840
tgccaactcc tcacacaccc tgaggtcagg gagtgctggc tcacagtaca gcatgtgcct   15900
taatgcttca tatgaggagg atgtccctgg gccagggtct gtgtgaatgt gggcactggc   15960
ccaggttcat accttatttg ctaatcaaag ccagggtctc tccctcaggt gttttttatg   16020
aagtgcgtga atgtatgtaa tgtgtggtgg cctcagctga atgcctcctg tggggaaagg   16080
ggttggggtg acagtcatca tcagggcctg gggcctgaga gaattggctc aataaagatt   16140
tcaagatcct cctgctgttg gaatctttta tacatataaa gttttttgtag agacatgagt   16200 ctctctgtgt tgcccaggat cctcccaact tggcctccca aagtgttggg attacaggtg   16260
tgagccaccc tgcccagcct ggactctttta ttattatagg cgcagagctg cagttgcccc   16320
tcatggtgcc agaagttgcc aagggtgatg acaggctcc caggtgtctt gcaaagtcac   16380
catggaccaa tttgtgaaga tgtagtatgc atacatactt ggtcatcact cagctccctg   16440
gggctcaggt tgtggtggag acaaaaatgg actgcagtta gaacttaggg aaactggctg   16500
ggcatagtgg ctcacacctg taatcccaac actttggttg ggctaggtgg gcagatcact   16560
tgaggccagg agttcgaggc cagcctggcc agcatgcgca aacccatct ctaccaaaaa   16620 tacaaaaaaa atttagctgg gcgtggtggt gggcgcttgt agtcccagct actcagaagg   16680
ctgaggcagg agaatcgctt gaacccggca ggcagaggtt gcagtgagtg gagatcacac   16740
cactgcactc cgatagagca agactccaac tcaaaaaaaa aaaaacggc cgggcgcagt   16800 ggctcaggcc tgtaatccca gcactttggg aggccaaggc gggtggatca cctgaggtcc   16860
ggagttcaag actgcctgac caacatggtg aaacccgtc tctactagaa atacaaaaaa   16920
attagccggc atggtggcag atgcctgtaa tcccaagtac tcgggaggct gaggcaggag   16980
aatcgcttga accctggagg cagaggctgc agtgagccga gatcgtgcca ctgcacatta   17040
tcctgggcga caagagtgaa actccatctc aaaaaaaaaa aaaacaaaa ccatcccttc   17100
```

-continued

| | |
|---|---|
| aacacacaca caccacgctc tgggagaagg tgtggcataa ctccttcacc aaatacagag | 17160 |
| ctgccaccgt ggaccagaca ctgctcgtga taccgagggt atagctgtta acaattcttg | 17220 |
| cttttcattaa gcatggactc tgctgggttt gaaaacactg aattcgaagt tcttcagaac | 17280 |
| tgaatgtaac tatgtgaatc tggccagttc cttaattttc tttcaacttg gttagttcac | 17340 |
| ataagcgtgg caatcgcaaa aatacagctg tgaaaataga agccagatgg gcacccggcg | 17400 |
| gtctggcctt aggccctgaa gtgcaggttt gaggattggt gcttgcgaag tcctgctagg | 17460 |
| cctgaactca ggtgttgggg gacgtcagag ccgccaaata cacccaaaag accgggagga | 17520 |
| ctcacggcca ccactttcct cggtgggagc tgtcccagct ggtcagatcg cgcttgctgg | 17580 |
| gacctgggat ctcgcaacgc atgctgggat gcccagcatc taagggcgcc cattggtccc | 17640 |
| gcccccacga cttgagcaac agccaatcag aggtggcagc gtgcggaagc ggaagtgagg | 17700 |
| tttccgtgga gacagccgag cctgcggaag gcggcggcgg cggcacctgc gatcagcggc | 17760 |
| tggggcaggt tatggtagtg cggactgcgg tgtgagcaga gcggcacgg ggcccgccat | 17820 |
| gcgccggcgg ccctgacatg ggcgccagcg ggtccaaagc tcggggcctg tggcccttcg | 17880 |
| cctcggcggc cggaggcggc ggctcagagg cagcaggagc tgagcaagct ttggtgcggc | 17940 |
| ctcggggccg agctgtgccc cccttcgtat tcacgcgccg cgggtaaggg catgggttcc | 18000 |
| accctggcgg ggggaacagg cgggcggcca ggcgtcccgc gccacggggg aacttccacc | 18060 |
| gctgtacccc actacagcca agccaggacg accccccatat tttgagcctc attggagctg | 18120 |
| ggggtggaga aagccgggca gtggtctcct g | 18151 |

<210> SEQ ID NO 14
<211> LENGTH: 20911
<212> TYPE: DNA
<213> ORGANISM: Homo sapiens
<220> FEATURE:
<223> OTHER INFORMATION: TBX3

<400> SEQUENCE: 14

| | |
|---|---|
| agggatctcc aggctgtcat ggttgctggg aaagatgagg gagggaaagg gggcagagta | 60 |
| cggaggcacc aggtcagaaa gacaggagag aattcagaca ggaccaaaac agccagaaaa | 120 |
| aataggataa agaaggtaga aaaaaaaaaa aaacaaaaca aacatgaga agttaaagcc | 180 |
| tgggaaatag atacaagaca agaaagagaa atagaaacca agaacaagat tgatgaaagg | 240 |
| aggagaagag aaagtagaag gaaaaagaat aagaaagatt ccagacacgc attcaaataa | 300 |
| tcctaaatgg ggatgagcag aaagacaagg agaccaaaag aaaagggggg gggggggtgg | 360 |
| tggggaggag aaagaaagga atggaaaaag aaacaaaagg tgaatgtcct gccctgtctg | 420 |
| tctggtccaa ccaagaagct agtgtctgcc ctggagggag gaaaggtggg ggagtccagc | 480 |
| ctgtctccaa gggactgaca ggcagcttct ggaccagaga ggaactaagc tctcaaagca | 540 |
| agctttgggg aggaggaagg gatgggggtg catggtgagt ggagactcct ggaggaagag | 600 |
| caagcctcca ctgggttcag cactgccagg gggagagtca gggttcaggg tagcatagca | 660 |
| gtgctaatgt atgtacccca gaggggtagg gggtgctagg gcaatttgca ggaggaccac | 720 |
| aaacagtaaa ctagagagct acttccctgg gatccgtgat aagaaaatca cttcctcagg | 780 |
| tgggagaatt gagcccgaaa gagaatggga gcccttgggg ggcaggcacc tggtcagttt | 840 |
| caaagctcgt caatatcaaa agaggctggg atcctgagat caaatgggct ggggcactgg | 900 |
| gcagaaacga ggagccattg ccaaactgcc aggatgacca gaacgcccct cccccaggaa | 960 |
| aagttcatat atgaacccac ccctgtatga aacttcttaa ttaggtctca taccccggt | 1020 |

```
gaatcttgga tgcccttctg tcaacagaat tcccaattta gtgacacctc ggactgaaaa    1080
gagctctgcg gcaaacgggg gtgaaagttt aagagggaat aagcatataa tactcccttg    1140
ccagacctca cacatgctga agggaatatt tacagcaaac tggccaaagc aaacgacccc    1200
gcctacccac catccttttta ccctcctccc cgcccttttt gtaaactcca gataaacacc    1260
atttgatcac aaaagggtcg gtttgtcccc tttatagttt gaggcaggca gtgcggcagg    1320
gaaaagtggg gtgggctaag cttccgtctc gggcaaggcc agcttctttg ctggcaccgt    1380
ggcctgggct aaggacagtt gatttggttt tgtttccccc gacccccacc ccgacccac     1440 ccccacaaag gaacattatt ttcagggtcc tcccccacc cagctttaac actcgcctac     1500
ttgcacccgc actactttaa atgctgcggg cattgcagat agagaggttt ttcagttaat    1560
ttactttttt aattctagag ctacaattaa gtgaaaactc tttttgcgaa aaggtggagg    1620
aatatttcag agacgccaga aattatctgg gtcttttctg acccggaatc tgccctcttt    1680
ctcccttctc ctcccttaa gtcaccctt tctgggactc tgttgaaggg caggctcttt     1740
caacgtctct agtctgtctt ttgttgagtg tgagaccgaa ggaaagagga tcgaggggtc    1800
tgcagagaga aaaagaccgc agatagccgg cagctggcgc ctaatgccgg ggtccgggga   1860
gcgctggcct cgtgggttct cctggaggcc aggcccagca caagccttcg gaacacgctg    1920
gccaatgttt aacccgaatg cagtggccac caggccgctt ttgtttgttc gcaaattaat    1980
cacccagcgc atggccggcg ccagagtggg tttatcaccc accgggaggg gggcgcgccg    2040
ggcacgcaga gacaaagagg agttcgcacc ttcccgctttt tgatcccaga attacgcgg    2100 cctccctgcc taatacgagc ctcctggggc cgagtctggg aggtcagtca taattggcgg    2160
aagtttgcag accattagca agatgtcgac atttttcgatt cgaaccccgc aaactttcct    2220
ctcgttctct gcttcgcgcg ctggaggttg gtgtgggaga ggagatgggg gtcagaagta    2280
gcgatctggg gtgatcacag ggttaagtta gagctatggg caaaaaatag gcaattgagg    2340
gaggaggaca gtgtgagggg cagaactccc tctcagtcca cccgcggagc caaaaacaaa    2400
tctagacatt tttaagtaaa atccgcaagc tccctcccaa tttccaaagc tgacagctgg    2460
ccagaatgca gaggaatgtc tctctgctgt gcgtgggacg cttgggggca ccgagtgggt    2520
gaggaggagg tcggtcacag tgtggttgta gaactacttt gcttccaccc caagtagtgg    2580
ggcagagatt ggcctgcgag ggcaggcagg caaaaccaga tcgctgggat ttggggccgc    2640
tcttgaaaga gcagcgaagg ggccccaggc cccggaggcg agcagtctgg gggagggggt    2700 gcacttttttt tttctatttc tttctttttct tttcttttttc tttttttttgg ggcggggtc    2760 cccagagact catgaaaccc tgcagtgact tccgtgttct gtgtaaggcg ggaaatggcc    2820
tggcctttcg caccctttcag gtggggagga gggatgcgg gaggggtgt tatgagccaa     2880 cactctgggg caccaccacc tcgtaatttt ccctctctct cctttctcta ttttaaccac    2940
tggcagagac agagaggacg ccagagaaag acagactgaa aggaaagaa aggggcgaga     3000 tggcgagcca gacggagttc gcagaaccac actattctct ctggtgactt cagggaattc    3060
tcaacgctgg cgccaagctc tcttaaccat gtgcgtcaaa aatgcgaggc tggagaagcc    3120
tgtcgcctca aaagatcctc ccctatctca gcgtggttgg cccacaagag cacttcattt    3180
tcacccttcc cttggtgcca cgttggggtt tcggggttgc tgggggttgc gcgggtgcac    3240
aaggcaaaat gcgagagagg cctgtgctgg cctacagaga cacacacatc caaagccctg    3300
agtctcttaa accctaagc ccccagatca gcccttctc cgttccctttt ccatcgaaga    3360
```

```
agctttcatc tcaggaaaga taaaagaaca ttgttttcaa gatttccctc catctaagca    3420
aggatggtcc aagacattgg cccccagaat caagaactgt gggcttaggc gaatcctctg    3480
accccgaccg ggcgctgcgg taacagagtt ggtaattcgg cgattggtaa gatccggtcg    3540
tttcctccc gtccgcctaa gaggaggccc ccaccctacc cgtactaaaa acagtcaact     3600
cgcctctgag gtggggcgt ttcacggttt gttttacaaa ttcaccctcc ctccccgact     3660
tctggccaga ttaagtcccc ggggtggaga aagaactgag gcaccgagag ataagtgcga    3720
tgcctagaga agataccagg ctggcgcgcc tcccccaacc caatcgccca cccctaccc    3780
tgtgctgtgc acccagccgg gcctcgaggt gagggcagcg gcttggaggg gacaggctca    3840
gaacccagtc tctcgctgtg ctcgctttgt ccagatcctc cattctcttc tctacaccca    3900
cacccacatc caggtggaat atgggggccc gcatgcaaat gaaagacgag atccaaaagg    3960
gctggtaaat gcatttcata aaaatcccaa atccatcttc cccaggagct caggcagggc    4020
cagccgcgca ggctgtgtac gtgtttgtgt gtacgtgttt ttcggtgtgt gtttcagtcc    4080
cagtgtgttg gcgcgtgttc gagtacagat acaccggggg tgtttgggta cccgcacatg    4140
gctgcgggtg gggcgcagtg gagaggaagc ccacacatgc gtgtgctgag atatggccgc    4200
atccttgtgc tccccagcc cagacgcagg ggagaccagc accgagacac ccgagctcgg    4260
gagcccttca gcggcggccg ggcggagctt ggctccacgt ggggctggag agcacgcaag    4320
cctggagtct cggcgctcgc ttctcggctg ccgccggctt ttgtagaacc gagtggccgg    4380
atggcagctc gcggggaggc tcggccaccc gcccggctcg ccggggcgg ggagaagaag     4440
gagagctgga gagagaaccg gccgcggcgg tcggagaggc gagcggagtg caagagaggc    4500
gagcgcccct gcccggcgcc cgggcgcgct ctccgccttc cccgcccggc tcgcctgctc    4560
gctggctccc tccctctctc cctcccctt cctccttggc cctgcctcct ccctcgatcc     4620
ccggctggat gactgaggca tttcagacgt gggctgaacc agagcgagcg agcgagctca    4680
ggggctgcag cgatctctcg ataagccacc tagaggcgac tctgtgcgcg cgcgctcccc    4740
agtggctccc gcccgccctc tgatcatgtt gacatattca caggacaggc agtagtaccg    4800
atgcggcgct gcgacgttac agtttccgac accttctttt tataactcag ctctatcccc    4860
cagcactcga cctgtgaaaa ccacgcctat gcagcaacac aattggtccg aaagcgtcaa    4920
agagccaatc aagaggcctc cggctccccg cagcccacag cgcagcccga ccttctagag    4980
ccgccgagca gacgcccggt gaattctaga ggcggcggag ggtggcgagg agctctcgct    5040
ttctctcgct ccctccctct ccgactccgt ctctctctct ctctctctct ctcccctccc    5100
tctctttccc tctgttccat ttttttcccc tctaaatcct ccctgccctg cgcgcctgga    5160
cacagattta ggaagcgaat tcgctcacgt tttaggacaa ggaagagaga gaggcacggg    5220
agaagagccc agcaagattt ggattgaaac cgagacaccc tccggaggct cggagcagag    5280
gaaggaggag gagggcggcg aacggaagcc agtttgcaat tcaagttttg atagcgctgg    5340
tagaaggggg tttaaatcag attttttttt ttttaaagga gagagacttt ttccgctctc    5400
tcgctcctg ttaaagccgg gtctagcaca gctgcagacg ccaccagcga gaaagaggga    5460
gaggaagaca gatagggggc gggggaagaa gaaaagaaa ggtaaaaagt cttctaggag    5520
aaccctttcac atttgcaaca aaagacctag gggctggaga gagattcctg ggacgcaggg    5580
ctggagtgtc tatttcgagc tcagcggcag ggctcgggcg cgagtcgaga ccctgctcgc    5640
tcctctcgct tctgaaaccg acgttcagga gcggcttttt aaaaacgcaa ggcacaagga    5700
cggtcacccg cgcgactatg tttgctgatt tttcgccttg ccctctttaa aagcggcctc    5760
```

```
ccattctcca aaagacactt cccctcctcc ctttgaagtg cattagttgt gatttctgcc    5820
tcctttcctt ttttctttct tttttgtttt gcttttcccc cccttttgaa ttatgtgctg    5880
ctgttaaaca acaacaaaaa aacaacaaaa cacagcagct gcggacttgt ccccggctgg    5940
agcccagcgc cccgcctgga gtggatgagc ctctccatga gagatccggt cattcctggg    6000
acaagcatgg cctaccatcc gttcctacct caccgggcgc cggacttcgc catgagcgcg    6060
gtgctgggtc accagccgcc gttcttcccc gcgctgacgc tgcctcccaa cggcgcggcg    6120
gcgctctcgc tgccgggcgc cctggccaag ccgatcatgg atcaattggt ggggcggcc    6180 gagaccggca tcccgttctc ctccctgggg ccccaggcgc atctgaggcc tttgaagacc    6240
atggagcccg aagaagaggt ggaggacgac cccaaggtgc acctggaggc taagaacttt    6300
tgggatcagt ttcacaagcg gggcaccgag atggtcatta ccaagtcggg aaggtaagca    6360
gtgggggcct cctcccctaa gctgttggag agttttttcc tcccttttatt tctctgctcc    6420 cagaacagtc ggttggtcgg ttattacggc ttggacgaaa agttagttcc cctagaaatg    6480
tatgcacaga cttccaggcc ctgccccggt ggcaggaaat ttcagcttac ctgggcatct    6540
gcatgggtct tgcatttggt ctgcatcctg ggttccctcc cgaacagaca gaattttca    6600 gtggagcaca gacatccctg cagggagcag gaaagaaaaa aaaaaaggc actctactgc    6660 aagaaactca ctcttcaaac cctcctggaa catccttatt tctttgttga tgttgtgttg    6720
tctgttttat tttgttctca gagagaaaaa cttaaagccc tttccttttg tgtgggtatt    6780
gggaggcctg acaccattcc ccggccctttt ctgccctcca gtctagcctc tgggtctaaa    6840
ggggcctgct gctgccctgg tcagagagaa atcgaagggc attttggttt gtttgcccac    6900
actacttcac gtgtctgtaa cccaagggcg agttcagcag gcaattttgc ataatttaag    6960
attatgtttg cagacttaag gagccagtga ggagacacac cctttttttt taatgtgtga    7020
atattatcaa ccatatttta cataatgttt aaaggtcctt gcctgaccaa aacctgcctg    7080
gaagagaaga tcctgtaata gtcatttaaa atcactgatt tttttttgt aatagcattg    7140 aagcctgtaa aggcataaag ttgatacaaa ataaaatcc ccttcatgat atcttaagcg    7200
ttctgtctcc ttccaagcta aatgaggcca aagtttggca taaaatcctc ctcaaactca    7260
caagacattt agtcagtttt ccagcaaagt gcttccttgc ttccttttaa gtcaagacta    7320
cagaatgcca acccttctgt gaaattaaca gcaatgtggt ggcacagtct tgcggttttg    7380
gactggccta agaagtgggg gaatgtgtta gcagctccac gggcagatcg gttatcaggc    7440
ccaggagtgc accgaagtct gcaaaattcg ttctgggaac tcactgaagt ccagtttcac    7500
ttcgcccaca gcgggattgc tattctgcag cagggagggg tgcaacttga cgttcatttc    7560
cttgataagt ttaacatttt ctcatcaatg ggtggtggaa aattctagtc ttaactgacc    7620
gcgctttaca aaaatcttac cccaacctgt ttagatctag atacccacag aaaaagacat    7680
gggcaagaat ttgctctcag gagggcaatc tgtaaagtca agcaaggaca aaaaaaatat    7740
tgaagaaatt gttagacaat gtagagaatt gcagtgccac aatgcatttg ttttgaacct    7800
tgggacgtct aaatatggcg aaactgagaa tatttaatac gttagttgtg gaagaaaacg    7860
attttgcaac cagttgcctc actctgaaac atgtaagctt atcagtcaca atataaagtc    7920
ttagacttgg tttcaatatt atgtgataca taggaaatca aacccaagat tacgggtggt    7980
ttatctttct ttttctttc tattctttcg ttttataggc gaatgtttcc tccatttaaa    8040
gtgagatgtt ctgggctgga taaaaaagcc aaatacattt tattgatgga cattatagct    8100
```

```
gctgatgact gtcgttataa atttcacaat tctcggtgga tggtggctgg taaggccgac    8160
cccgaaatgc caaagaggat gtacattcac ccggacagcc ccgctactgg ggaacagtgg    8220
atgtccaaag tcgtcacttt ccacaaactg aaactcacca caacatttc agacaaacat     8280 ggatttgtaa gtttcattgc tctcttcagt aaaattttct cctccttcac tcagtcaaag    8340
gcagtgcttc ccatttcatg agtttcagcc cagacttctc ctttgcttct ccctaagcat    8400
agcaaacttg tcctcgtctg gaaaaaggat tcggggtgtt tctctccaaa taatggaagg    8460
cctggcgttc taaaagaaat ggggcaagaa aacttaccgg cttgtgttct atagcaattc    8520
cagctctttg gtagattcct gacctgagag tgaagttaaa aaccatttt taagagctaa     8580 aatcaatttc aaggctatgt attcctaaag gatttgtttt gttttaaaat atcatacttc    8640
tgttttgaaa ccagtgatat tattttctca ggagagttta cgtttcggag ccttgactct    8700
gttggttaaa tggtgtgaat acattttaa aaactcgttc ttttactaaa aaaagaattg     8760
ggcttaggtg ggagtccggc ttaccctaaa tgaggcttag atcttcagaa aaaaatggtt    8820
tgtgtgttgg gagtgtatat atggattcag tgacagtgct tagaaactta gaaactttc     8880 attgcttgta gatatcaggc aaaggacctt ttgcgccttt tcctacccct ccccaacatt    8940
tcaataaaat aaacagcgtg ataagcaagg agtaagcaga aagattaggc ccaggaagac    9000
gcgaatggcg cggaaatatc ttcagcgggc aggaattgca tttgaagccc ttgatttgat    9060
taaggcataa atattcctct ctagagttca gcctttcagg gctttaagtg gattgggctc    9120
gtcaattagt gggcgcttaa agtactgaat cattttgtaa attaaaatgc atgttttct     9180 ctatctttta agactttggc cttcccaagt gatcacgcta cgtggcaggg gaattatagt    9240
tttggtactc aggtaggcta gggttcaagg tatgaatgat ccttagatgg tgagggtggg    9300
gggggccctt tggcaactga ggagcaattt ggattctcca gaagataaca tctgtggagc    9360
gaaacgtacc caggggggtac tccaaggagg tgggctcggt acaagcgtgg taccctgcgg    9420
tggggaagat ttcagcctgg caggggtcct aagatcccgt ttgttctgct aaatccttgt    9480
tttatgtatg tctcctcttc cctgcccctg cagactatat tgaactccat gcacaaatac    9540
cagccccggt tccacattgt aagagccaat gacatcttga aactccctta tagtacattt    9600
cggacatact tgttccccga aactgaattc atcgctgtga ctgcatacca gaatgataag    9660
gtaaactcaa ggggctttcc tttttaatgg tgatattttg ccttcccctt aaaagctgct    9720
ttaagtcagg atgagaaagt tacaagagag tggagacgag agtcttgagt tgtcttttgt    9780
gatttgtgga gcatttgggg ggaaaggaca atgacacctc gaggagacag aaaaacacct    9840
tgactaggta ggaacaatgc tgagcaaaaa aacgccatac taattttgcc acagagaaac    9900
tcctagaact gctgtcattg atgccaccca ctcctccccc cctcttgggc tttgtcctgt    9960
ctgttttaag gttcatcttc ttcccttgg ggaagaagga tcaagaagtc acattcaaaa     10020
ggaaccagct aaaatttaa ggcaaaagcc atttgggatc ctgggaggag aatcctagta     10080
gagaccagct tttctcccct agccagaaat cctgagtagc tggtctggtt tttattacct    10140
tttatgctgc tgtgttatga tgtgtgtgtg tgtgtgcatg tgtgtgcatg catgcgtgtg    10200
gttgaaaaaa cctaccctga tcacaggggtc atattaatcg agttgtctga ggcttttgag    10260
ttggggtggc caaagtcacc acttcatttg aattccccccc ctccccagg cctgaatctg    10320 gaggttagaa ggatccccaa aagggaaagc acctgatatc tagagctatg gtggcctgaa    10380
ggtcatgggc acagaaaaag tgaccccttac tgctgattca ccagttccca gattggctgt    10440
tagcagttat ggggtgggag gagggactga agacccctgc tctgcaatcc tggacttcaa    10500
```

```
agagagtcca ttttacctga caacacactt cattttgaac tcactgtcat tgtcactgtc   10560
cttgggtcct ctgtggactt catgatgggg atgttccagc taaatttctt tagtgtgaat   10620
accaaaacat gatcttctct ccctgtgaaa cctgaagtct tcaatagagc aatttattcc   10680
aagaacatga atccaaccaa gggtccccct ttccacctct gagtaactct gtgtatataa   10740
cttcttcttc ccaccaaggg gaagggattt gaaagattac acactatagc attttctca    10800
aagtgcaaaa tgcatgtgcc ctctagaccc agaatcctgt gaaatgaagt tgttaatgta   10860
ataataaaat gtagcatttt tgatcagaca aaaaggccat gggccttctc cacctaatgg   10920
ccatggcaga gcatataaat gaaaacagat gtttccagtg gtcattcagt actgtaactg   10980
tcaatattgt aatttcctca aaccaccccc caggcaaaga aaaaaaaaat taaactcact   11040
cccgcactca ctcccgcaca agggtagtga accccataa atcatttatt ggattcatgg    11100
aaaaggagtg tgtgtgtgtg tgtgtgtgtg tgtgtgtgtg tgtgaaggga gtatgctata   11160
atttatgatt aattgcactg tataaaaatc aaaatgaaag cataatttta agatctacag   11220
gttttccctc ttgatgactt tgacaacact tccatgtcta aacccaaact gttggctgcc   11280
caaagaaaag aatttctttg aataatttca tccccaaatc cctggtttgg cctcatatag   11340
gagatacaag ccctgccaca gtttccttat tatctccttt ccctggcata tctatatgac   11400
ttctgttggc agtcacatct ctagacttgt tgagttggga aaaacaccct caaaacattc   11460
tagaaaatga gaacaatgtc tctgtcttgc ttgtgtctct tccaatagat aacccagtta   11520
aaaatagaca acaacccttt tgcaaaaggt ttccgggaca ctggaaatgg ccgaagagaa   11580
aaaaggtgag ttgaaacaat tatttattag atagtttaga aaaatcccctt ttttttaggat 11640
ccaactctga agtgttagaa gtgagatgca ggcacttatc ctaagagcgg gtggaaatca   11700
ttcactttcc ccactgctac atgcttgccg ctatcagtat acccaggaca agtactttc    11760
ctacctcctt acctttaagg aaattaacta ggctacacca tacttatctc tggaagagaa   11820
gcatcaggga taatagatta tacagggatg cctattaatt cctaattaat ttaagttcat   11880
cctaggcagg tcccagaaag aaccatgcca ttgagaaaat acttgggaat ttttgcaatc   11940
ctgtcttcca aataccatca gacagagctg gggacttcgg aaagatgtat ggctctctcc   12000
ctccttcgtg gggacatgta tcattttgca ttacgtagac agctggagag tatatgaaag   12060
agggtctccc ctcccccacc ccctttcaaa gaatttctaa aatccagaaa atcaccccca   12120
aattttttaac ctatcccctt ggggcgggca ttaaaaaata attgctaaca gctaaatata  12180
tttttattcc aattaatttg ttagtaaaac gattacagta aagtgcagca tgaaataacc   12240
acttcctccc aatcttagcc accatccaaa atttgggtat gctggggaca gacagcgttg   12300
tgtttgcagg attggacacc cggttctccc tatataaggc tggcagtcca gctgtctctg   12360
actagatcca gcctcttctc ctgctttttaa ataaaatttc acagcccaag caaatgcctt   12420
ttcctaatga aaccccatct tgaataaatg caactgaagc ctccttcctt tctccctaac   12480
cctctgccac actcttcagc ccagttagag ggtcaaggac aaagcttggg tctatgtggc   12540
tgccctgggg caagcagatt tcagtgaatt agcgttgtcc ctgggcagca ggcagggtgt   12600
gaggtatgtg tgtgccgctt tggaaagggt aaggaaaca aagagggggaa atgtatgtta    12660
cattctgtaa cctgggtgtg ggcttctgcc acagaaaaca gctcaccctg cagtccatga   12720
gggtgtttga tgaaagacac aaaaaggaga atgggacctc tgatgagtcc tccagtgaac   12780
aagcagcttt caactgcttc gcccaggctt cttctccagc cgcctccact gtagggacat   12840
```

```
cgaacctcaa aggtaaacca tgtcaccttt gtgatcactg gactccagtc cctcgtggcc   12900
tggaagagtt gaaggggat gggcaccaa ccagggcact tgcccttaaa aagctagaag     12960
ccttctaaac atccttaaac agaagccaga gttcaaaaag ggctatcagg tgtgtctccc   13020
cttccccgct aaggcagtag aaggagagca cagaggcctt tctcccagat ccttatttgg   13080
ctggtgggga gggaggtgg gtgtctgttt gcatactacc tcttggcaag cagctttgaa    13140
aacttgcttg aagcgcttct ctcttttctc tctgtctctg tttctttctc ctcccattct   13200
ctccaaccaa cagaggctcc aactgctgac ttttcactgt ctttgaactc taggttacaa   13260
tgtgttggac tgggtgggg ggaagcaagg gactctgcca cctggaaccg agaaggtggc    13320
ctagaaaaca tccagctata aagcaacaat tgacctggga gaggaggtgg agcactgggg  13380
atctgcggtg ggggtagagc tgggggaggt gggtgaggag tggacaagat ggctcaaatc  13440 cccctcagt tacctgtgtt taaagagcaa gcagtattta tttggaaaga cacacacaca    13500
cacacacaca cacacacaca cacacacaca ctctcaacgg gaagaaacct gtttttagt    13560 gaaataaaat gcaagtcctt tatgtcttca atccatttaa gctttaaaca taaaatagga   13620
tccctttttc ttttcttctg gtggaacacc cacagagggt gtggtaaaag cgaaaaaaga  13680
atctatgatc gtccccgggc tgtgagccat ctgtccgaca ctcatctctc tctgcaggga  13740
ctggggcaaa tacaaacggt tcaactgagt actggtgttg aaggacaggt gtccgttctg   13800
ccattatcaa ttcagatgtc agggttcttg ccaaacaaat ccttccagag taattccaca   13860
atttgtggaa ggtgctgctc tctgtcattc actgattttt tgatagtaat tagaatatgt   13920
tccagctgtg agttttaatg ttactttta cttttaaaaa gttaatttgc aatcgaatgg   13980
ggagatgcat gtgaaatctg ccactgtagg aactcaaaaa agaagtaaa attcattaaa   14040 ataagaagag ctactgatta ggggattgtc catctaaggg aaagttaaa ctctgggtaa   14100 atactttaaa ttcataatcg cttattgaat tttccagcaa tgttgttggg cacgattatc    14160
cccattttgc agatgacaac actgaggtgc agagaggcta aggggcttc cccgggatta    14220 cacagccact aagccacgag ctgggattcc aacttgggaa ctggagttcc gttggctcat   14280
actggagata acgcccttct gccttggttt tttccttcgc ctgtggtaga tttatgtccc   14340
agcgagggtg agagcgacgc cgaggccgag agcaaagagg agcatggccc cgaggcctgc    14400
gacgcggcca agatctccac caccacgtcg gaggagccct gccgtgacaa gggcagcccc   14460
gcggtcaagg ctcaccttt cgctgctgag cggccccggg acagcgggcg gctggacaaa    14520
gcgtcgcccg actcacgcca tagccccgcc accatctcgt ccagcactcg cggcctgggc    14580
gcggaggagc gcaggagccc ggttcgcgag ggcacagcgc cggccaaggt ggaagaggcg   14640
cgcgcgctcc cgggcaagga ggccttcgcg ccgctcacgg tgcagacgga cgcggccgcc   14700
gcgcacctgg cccagggccc cctgcctggc ctcggcttcg ccccgggcct ggcgggccaa    14760
cagttcttca acgggcaccc gctcttcctg caccccagcc agtttgccat ggggggcgcc    14820
ttctccagca tggcggccgc tggcatgggt cccctcctgg ccacggtttc tggggcctcc    14880
accggtgtct cgggcctgga ttccacggcc atggcctctg ccgctgcggc gcagggactg   14940 tccgggggcgt ccgcggccac cctgcccttc cacctccagc agcacgtcct ggcctctcag  15000
gtatggatcc ttcttcctgc ctccaccagt cttttccacct ttcgtccagt ttccctgtcc  15060
tttgccagca gaccctcacc cgatcccttt ggcctagtag ctgtaataat ttttactgag   15120
ccattaccgg gttcaaggct tagctcatgg agttattatg acttcattct ccccattcac   15180
cccaaaaatc tttaaaattt ttccgaagtt aaaggctgtt tccagcagag tagataggta  15240
```

```
gtaacaaaga taacagctgg acacagcact tactttcagg cattcttcta agtgcttgct   15300
ctgtattgac tcatttgacc taaccottca ggggtactat tatcacctcc actttacaga   15360
tgaaggcgaa gacgcccaga gatgttgagt gacttgtcca aggtcacaca gcgggtacat   15420
ggtggagctg agactcaacc ccaggctatc tgactccagg gcctctttga gggtttctga   15480
ttttagcttc agagctgaca tgtctcttaa gtgtctcata gccaacccet ccccaggaat   15540 gggactctag gcctggggag gggaagtgac tacttcctga gtaggagttc agtcttgatt   15600
cctccagcct ttcctcccag ttcgaagctc ttctccccac ccccaacccc aagcaggcca   15660
gcctattcct cgaagggtta atggtttgtg cacacgtggg aaatgtcaga ggacaggat   15720 aagcagggac tggggcaggc ctggaggcct gtgtgtggct cagacagctg tgctgggggg   15780
aggtctcagg cggctggaaa caccctgaac tcgatgaaaa ggttctatga ggttttgcat   15840
gctgttgcct tttgttttgt ctgagcacat tcgtctggtc tcccttccct gcgccaagaa   15900
accagattgg cctccccact ccagggagga gggagctgag gaaaggcttg gcttctggca   15960
tttctcaatt cctcccatct cctctgctgg cttctccggg agaccctgtc ctaggtgggc   16020
aggtggttgg tacaccaagg actacctgaa cagacaaaac cttaagggca cctcaaggca   16080
tgatgcagag aactggccca ggccagggtg cctgcatctt aaatgctgct tctgccaatt   16140
cccagcttag tgcactcctg aactcctgcg gcctacctcg gcttctcacc tggaacacca   16200
gtgaatcatg ctggacgatt tctttgtctc tgtttataac aaatgccctt tttccctccc   16260
ccagccccag tttccttttg cttaagatct tcactgtctg ttttttttgt tttgttttgt   16320
tttgtttgga gaaacttcta ggattgggt gggaggatgg gggttgggga agaagaaaga   16380
tttaaaaaat tattcctact aatttatgtc ctccggcttc cccttggtta cctctgtggg   16440
gtaaactgaa tctgtatccc catttaacag gtgcaaggag atttcctggg ggctgcacac   16500
actgtgtgca gcatattgca ggcttttcact catttaatat ctacaaagtc ctcaataagt   16560
atatgaatta cttatgattt ccctgttttt tcttcctata aggaagctga ggcacaagtt   16620
aatcaaagtc tcttggccta gggtgacaca gctaagattt gtacctagag atttctgagt   16680
gttgacttct ctcctgcccc cacctatctc ccccccaaa aaaaaaaca caacaacaac   16740 aacaacagaa cataccaggg attcatggct tgcccaatgt tggaggggga gaagagagga   16800
gagggatgag ataagctcct cccacccggc tgactcgctg tgtgtctctt ttctcacccc   16860
agggcctggc catgtcccct ttcggaagcc tgttcccta cccctacacg tacatggccg   16920
cagcggcggc cgcctcctct gcggcagcct ccagctcggt gcaccgccac cccttcctca   16980
atctgaacac catgcgcccg cggctgcgct acagccccta ctccatcccg gtgccggtcc   17040
cggacggcag cagtctgctc accaccgccc tgccctccat ggcggcggcc gcggggcccc   17100
tggacggcaa agtcgccgcc ctggccgcca gcccggcctc ggtggcagtg gactcgggct   17160
ctgaactcaa cagccgctcc tccacgctct cctccagctc catgtccttg tcgcccaaac   17220
tctgcgcgga gaaagaggcg gccaccagcg aactgcagag catccagcgg ttggttagcg   17280
gcttggaagc caagcggac aggtcccgca gcgcgtcccc gtagaccgt cccagacacg   17340 tcttttcatt ccagtccagt tcaggctgcc gtgcactttg tcggatataa aataaaccac   17400
gggcccgcca tggcgttagc ccttccttt gcagttgcgt ctgggaaggg gcccggact   17460 ccctcgagag aatgtgctag agacagcccc tgtcttcttg gcgtggttta tatgtccggg   17520
atctggatca gattctgggg gctcagaaac gtcggttgca ttgagctact gggggtagga   17580
```

-continued

```
gttccaacat ttatgtccag agcaacttcc agcaaggctg gtctgggtct ctgcccacca   17640
ggcggggagg tgttcaaaga catctccctc agtgcggatt tatatatata ttttccttc   17700
actgtgtcaa gtggaaacaa aaacaaaatc tttcaaaaaa aaaatcggga caagtgaaca   17760
cattaacatg attctgtttg tgcagattaa aaactttata gggacttgca ttatcggttc   17820
tcaataaatt actgagcagc tttgtttggg gagggaagtc cctaccatcc ttgtttagtc   17880
tatattaaga aaatctgtgt cttttttaata ttcttgtgat gttttcagag ccgctgtagg   17940
tctcttcttg catgtccaca gtaatgtatt tgtggttttt attttgaacg cttgctttta   18000
gagagaaaac aatatagccc cctacccttt tcccaatcct ttgccctcaa atcagtgacc   18060
caagggaggg gggatttaa agggaaggag tgggcaaaac ataaaatg aatttattat   18120
atctaagctc tgtagcagga ttcatgtcgt tctttgacag ttctttctct ttcctgtata   18180
tgcaataaca aggttttaaa aaataataa agaagtgaga ctattagaca aagtatttat   18240
gtaattattt gataactctt gtaaataggt ggaatatgaa tgcttggaaa attaaacttt   18300
aatttattga cattgtacat agctctgtgt aaatagaatt gcaactgtca ggttttgtgt   18360
tcttgttttc ctttagttgg gtttatttcc aggtcacaga attgctgtta acactagaaa   18420
acacacttcc tgcaccaaca ccaatacccct ttcaaaagag ttgtctgcaa cattttgtt   18480
ttctttttta atgtccaaaa gtgggggaaa gtgctattc ctattttcac caaaattggg   18540
gaaggagtgc cactttccag ctccacttca aattccttaa aatataactg agattgctgt   18600
ggggagggag gagggcagag gctgcggtt gacttttaa ttttttcttt gttatttgta   18660
tttgctagtc tctgattcc tcaaaacgaa gtggaattta ctactgttgt cagtatcggt   18720
gttttgaatt ggtgcctgcc tatagagata tattcacagt tcaaaagtca ggtgctgaga   18780
gatggttaa agacaaattc atgaaggtat attttgtgtt atagttgttg atgagttctt   18840
tggttttctg tattttttccc cctctcttta aaacatcact gaaatttcaa taaattttta   18900
ttgaaatgtc tttgggcctt tgtgttaaatg ttttttctt gggaaccttt cctgaagatg   18960
gacagtcagg ggagggttta gtatcttctt gttctgagtt tacccccttc ccttcgcctt   19020
taaataatta agaccgcccc cagcgaacca aaatgagatg tcactcaagt tacaaagcta   19080
aaaacaaaag tcccttactt gagcgaaggg agccacttca atctgaaatt acttttcctt   19140
taaattaggg agcaaagcag ggagacggaa aggggcctga tgagaataca gaaagaaggg   19200
taatttcaga tacttttaag ttttaatgga aaaagactga tgtgctccct aagtcaggtt   19260
ttcccacccg aatccgacca aaagtaagct cggcaagtac gaatgttttt cgttttaagc   19320
tcgccctcag ttttgacatc aatctggcga atccaagtcg aaaataccttt cttgcaccag   19380
tgtgtttggc tcggggaaaa ggccagcaga atgccccagc agtccgagcg ggcttggcta   19440
ggcagcaacc ctccaggttg tagaagtgga caagacgcaa cgccttttcca ctcggcaacc   19500
ccccacacag cctgcagtcc ctggtgcctc aaattgaacc cggctggccc aaggcgcccc   19560
tacgaggccc catccatccc gagttgtgcg tgcaaagcgc ggccagctcc gcgaaaactt   19620
agctgtgtca cgcgagggag gagggaaatt atccccgaaa ggggaaaggt aattccaggg   19680
tgcacatttc accccctcca cggcaaaagt cacccaggag gctgacatcc tcccctagtc   19740
tccccttcaa acccgtctcc aggctgttcg gggagttgcc ttttgaagtt caatttatct   19800
ttgaaacatt caataaaaaa tgatgaggca ctgtcagtct tttggtctcc cgaccccccag   19860
cctcgcctcc gaggtgtgtg tctgttgggg ggcggggcg gcacgggaag gttcgagggt   19920
tagtccttag cccttttctt gccctggggg ccatgacgtg aagacccagc tggagcctgc   19980
```

```
ctggcggctg cctccctccc caccccccac ccgccacccc ctggagcccg ccagcccggc    20040
cccaagtccc tgtcaccttc aggcctcttg aatgaccgga gaggaggacg cccccctccct   20100 tccctcatcc tgtacttgga agggatcgag gtcgagacct tttggagagc ggggcaaagc    20160
cccttccatc tctggccagg cacgtgggga cccctacagc ctcctctgcg atgtctccgg    20220
gggtgggagg gaagacagac aaccagagta tgttggtgcg gagtcgcggg ggggggagg    20280 ggcggggtgc gctgcggggg tggcagggcc tgagctgaga cgggccctgg ggacctttga    20340
ggctggggct cccccgagga ctgggagatt tccagggcgc gctccttctg cgcagcggct    20400
acagcctgaa gggggcagct ctggatccag cgacaacgcg cggtgtccgc gcctctgaga    20460
aggtggtagt tggctggttg cgctctcccg aattggggaa aaaagaactc agcctccaaa    20520
agggaagaaa tgctttgctt ttctcttctt tctcagtcca aatttgctta cctcctccct    20580
tctctccccc cgcccccgat ttggggaccc tgctcagact tgtgtccagc ctctcttact    20640
ggcgttcctc tttttttttt tttttttttt ttaatctcct gtgtatctca tttgtatatt    20700
gtgatgttaa tgagtaactc ctgtagcgct gatgggcggg gggtggaggg gatgaacggc    20760
tcgcagtctc tctggatttt gctgcctatt actcacctgg cgccggtcgc aatctcgccg    20820
caggctttat ggtggctgcg gccgcccag aggccactca gggcaggcgc cttcgcctt    20880 tttctgggct tcgagtgcca cctatctgtc t                                   20911
```

MULTIPLEX DETECTION OF DNA THAT ORIGINATES FROM A SPECIFIC CELL-TYPE

CROSS-REFERENCE TO RELATED APPLICATIONS

This application claims priority to European patent application 14 167 769.0 filed 9 May 2014, the entire disclosure of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 27, 2015, is named DFMP-112_SL.txt and is 53 kilobytes in size.

The present invention relates to methods to detect an amount of DNA that originates from cells of a given type, where the sample comprising such DNA in admixture with DNA that does not originate from such cells. Such methods are based on differential methylation, at certain regions, of the DNA that originates from the given type of cells compared to the admixed DNA. Such methods have particular application in the detection, from a biological fluid from a pregnant female, of cell free DNA that originates from a foetus or the placenta of a foetus, or the detection, from a biological fluid from an individual, of cell free DNA that originates from cells of a tumour. Accordingly, such methods have diagnostic, prognostic and/or predictive utility for detecting an increased risk of an individual suffering from or developing a medical condition such as preeclampsia or cancer, and/or to aid subsequent diagnostic, prognostic and/ or predictive methods such as the detection of chromosomal trisomy in a foetus, including for twin-pregnancies. The present invention also relates to compositions, kits, computer program products and other aspects that are used in, useful for or related to the practice of such methods.

Cell-free DNA (cfDNA), especially that found in plasma or serum, has been the subject of considerable research over the past decade. Despite the original finding of circulating cell-free nucleic acids in the bloodstream being described by Mandel and Metais as early as 1948 (Mandel and Metais 1948, CR Acad Sci Paris 142:241), it took until the mid 1990s for proof that tumours shed DNA into the circulatory system (Sorenson et al 1994, Cancer Epidemiol Biomarkers Prev 367; Vassioukhin et al 1994, Br J Haematol 86:774), and until 1997 for the discovery of cfDNA originating from a foetus in the circulatory system of the mother (Lo et al 1997, Lancet 350:485).

Among other forms of characteristics shown by circulating cfDNA, numerous studies have described the presence of methylated circulating cfDNA in the plasma/serum and other body fluids of patients with various types of malignancy and the absence of methylated DNA in normal control patients (for review see Muller and Widschwendter 2003, Expert Rev Mol Diagn 3:443). Although other characteristics of circulating cfDNA exist and are important for diagnostic, prognostic or predictive studies (for example, sequence mutations and micro duplications/deletions), such methylation-based epigenetic characteristics have become an increasingly important source of serologic markers for diagnosis, risk assessment and even for therapy monitoring during follow-up of cancer patients.

Likewise, the use of differences in foetal cfDNA present in the maternal circulation has been the main goal for the development of non-invasive prenatal tests (NIPT). Foetal cfDNA is derived from embryonic cell degradation in maternal peripheral blood (Lo et al 2000, Clin Chem 46:1301) or from apoptotic placental cells (Smid et al 2006, Prenat Diagn 26:785). It has been demonstrated that foetal cfDNA from maternal plasma is cleared immediately (within s few hours) after pregnancy (Lo et al 1999, Am J Hum Genet 64:218). This finding is of great importance, since the presence of foetal cfDNA from previous pregnancies would otherwise interfere with the correct interpretation of subsequent pregnancies.

It is believed that 60% of tissue-specific differentially methylated regions are methylated in embryonic cells, while during the differentiation of embryonic tissues to adult tissues, they undergo de-methylation (Kawai et al 1993, Nucleic Acids Res 21:5604). Based on the evidence that foetal cfDNA in maternal plasma is of placental origin, epigenetic differences between maternal peripheral (whole) blood and placental DNA have been used to detect a hypomethylated gene sequence (maspin/SERPINB5) in maternal plasma derived from the foetus (Masuzaki et al 2004, J Med Genet 41:289; Fiori et al 2004, Hum Reprod 19:723: Chim et al 2005, Proc Natl Acad Sci USA 102: 14253). Subsequently, a number of additional differential foetal methylation-based epigenetic molecular markers have been described, including the RASSF1A gene on chromosome 3, as well as a marker on chromosome 21 (Chiu et al 2007, Am J Pathol 170:941; Old et al 2007, Reprod Biomed Online 15:22; Chim et al 2008, Clin Chem 54:500) and others including T-box 3 (TBX3) (Nygren et al 2010, Clin Chem 65:10; WO 2010/033639; WO 2011/034631).

Various methodologies exist for NIPT based on the analysis of foetal cfDNA. For example, foetal sex determination using eg DYS14 (Lo et al 1997; Lancet 350:485), as well as foetal Rhesus D found in maternal circulation in pregnancies in which the mother was Rhesus D negative (Lo 1998, N Eng J Med 339:1734). Also, and of particular relevance, are those using next generation sequencing (NGS) technologies on cfDNA isolated from maternal plasma with the primary aim of detecting the most common chromosomal aneuploidies as commercially available tests (for example, those using random massively parallel sequencing: www.sequenom.com; www.lifecodexx.com; www.verinata.com). Other technologies include targeted approaches, the aim of which is to enrich specific genomic regions of interest before sequencing to reduce the number of sequence tags needed to perform a reliable statistical analysis (eg www.ariosadx.com or www.natera.com), polymorphism analysis or digital PCR (for review, see Go et al 2011, Human Reprod Update 17:372). However, regardless of the specific technology used, current applications of NIPT rely on the qualitative detection of foetal cfDNA to determine the genetic makeup of the foetus. Such an approach leads to an analytic dilemma, because test results from samples that do not contain any or sufficient foetal DNA or are contaminated with maternal cellular DNA can be misleading. The analogous issue arises in diagnostic, prognostic or predicative tests of tumour derived cfDNA from the circulatory system; the quality of the test result often is dependent on the presence of sufficient, or sufficiently pure, tumour-derived cfDNA in the total DNA from the sample.

The quantitative determination of an amount of DNA originating from such a cell type may, in itself, form a critical part of a diagnostic, prognostic or predicative test. For example, even though studies have demonstrated that the amount of foetal DNA released in maternal circulation increases with pregnancy progression (Lo et al 1998, Am J Hum Genet 62:768), preeclampsia, which results from abnormal trophoblast invasion, is also associated with further elevated foetal cfDNA levels in the maternal circulation. Lo et al (1999, Clin Chem 45:184) demonstrated a fivefold increase in circulating foetal cfDNA concentrations in the plasma of symptomatic preeclamptic women compared with control pregnant subjects, and further studies have investigated if elevated serum foetal cfDNA developed into early-onset preeclampsia (Yu et al 2013, Int J Mol Sci 14:7571), and the potential of cfDNA as a marker for preeclampsia is being increasingly studied (for review, see Hahn et al 2011, Placenta 32(Supl):517). An increased level of circulating cfDNA and/or the level of methylation of such DNA at certain regions is also associated with other medical conditions. For example, hypermethylation of serum cfDNA was found to be common in patients suffering from oesophageal squamous cell carcinoma, and diagnostic accuracy was increased when methylation of multiple genes (RAR-beta, DAPK, CDH1, p16 and RASSF1A) were analysed in combination (Li et al 2011, Epigenetics 6:307). Elevated levels of circulating cfDNA have been reported in patients with acute dengue virus infection (Ha et al 2011, PLoS One 6(10):e25969), in acute Puumala hantavirus infection Outinen et al 2012, PLoS One 7(2);e31455) and high cfDNA has been reported to predict fatal outcome among *Staphylococcus aureus* bacteraemia patients with intensive care unit treatment (Forsblom et al 2014, PLoS One 10;9(2): e87741.

It is known that foetal cfDNA present in the maternal circulatory system and tumour derived circulating cfDNA is degraded. For example, studies characterising cfDNA in maternal plasma have found that the size of foetal DNA fragments were estimated to be <0.3 kb, whereas that of maternal DNA was >1 kb (Chan et al 2004, Clin Chem 50:88). Follow-up studies have demonstrated that the release of foetal DNA is due to the apoptosis of no more than three nucleosomal complexes, it has also been shown that the average foetal fragment size is 286+/−28 bp with a maximum foetal cfDNA fragment size ranging from 219 to 313 bp (Kimura et al 2011, Nagoya J Med Sci 73:129), and another study has reported that the most significant difference in the size distribution between foetal and total DNA is that foetal DNA exhibits a reduction in a 166-bp peak size and a relative prominence of the 143-bp peak; the latter likely corresponding to the trimming of a ~20-bp linker fragment from a nucleosome to its core particle of ~146 bp (Lo et al 2010, Sci Transl Med 2:61).

In cancer patients, circulating cfDNA in plasma is protein-bound (nucleosomal) DNA and has a short half-life (10 to 15 min) which is removed mainly by the liver (Elshimali et al 2013, Int. J Mol Sci 14:18925). Accumulation of cfDNA in the circulation of cancer patients cars result from an excessive release of DNA caused by massive cell death, inefficient removal of the dead cells, or a combination of both (Zeerleder 2006, Crit Care 10:142). It should be noted that although cancer patients requiring renal support have higher values of circulating cfDNA, the renal elimination is not the main mechanism of its clearance. The plasma levels of circulating cfDNA do not seem to be dramatically altered in chronic kidney disease, peritoneal dialysis or hemodialysis (Kirsch et al 2008, Ann NY Acad Sci 1137:135).

Although the nucleosome is a very stable protein-DNA complex, it is not static and has been shown to undergo a number of different structural re-arrangements including nucleosome sliding and DNA site exposure. Depending on the context, nucleosomes can inhibit or facilitate transcription factor binding. Also, packaging of DNA into nucleosomes varies depending on the cell cycle stage and by local DNA region (Russell 2010, "iGenetics", 3rd ed. San Francisco; Pearson Benjamin Cummings, pp 24-27). The degree to which chromatin is condensed is associated with a certain transcriptional state. Unpackaged or loose chromatin is more transcriptionally active than tightly packaged chromatin because it is more accessible to transcriptional machinery. By remodeling chromatin structure and changing the density of DNA packaging, gene expression can thus be modulated. Accordingly, and without being bound by theory, the qualitative and/or quantitative level of chromatin packing of a given region of cfDNA may affect its stability, and hence the amount detected in the circulatory system at any given time. Correspondingly, differences between the level of chromatin packing between different DNA regions (for example, due to differences in each regions state of transcription) may influence the relative quantities of DNA from each of these regions when detected as cfDNA, particularly as two studies have investigated in more detail the kinetics of, and reported the rapid, clearance of cfDNA from the circulatory system (Gauthier et al 1996, J Immunol 156:1151; Lo et al 1999, Am J Hum Genet 64:218).

Various prior art methods have been described to detect, and quantify, cfDNA from a specific cell type. Quantitative analysis of aberrant p16 methylation was described using probe-based real-time quantitative PCR (Lo et al 1999, Cancer res 59:3899). Analogously, differences in the methylation of the placental mapsin gene found in material plasma has been described, and the methylation signature further analysed using MALDi-TOF mass-spectrometry (Chim et al 2005). Total cfDNA and that from male foetuses (only) were accurately and robustly quantified in material plasma from 5 to 41 weeks of gestation using a Y-chromosome specific marker (SRY) (Birch et al 2005, Clin Chem 51:2). Hypermethylation of RASSF1A has been proposed as a universal foetal DNA marker to improve the reliability of NIPT, and was studied in a duplex probe-based real-time PCR reaction compared to the non-differentially methylated region on the beta-actin gene (Chan et al 2006, Clin Chem 52:12). A complex method of quantification has been described (Nygren et al 2010; Clin Chem 56:10; WO 2010/033639; WO 2011/034631): starting from a 13-plex competition-PCR reaction (5 differentially methylated regions (DMRs) including TBX3, 3 regions on different genes for total DNA quantification, 3 for quantification of chromosome Y and 2 for restriction enzyme controls), such a complex reaction is subsequently processed for singe-base extension reactions and finally mass-spectrometry is subsequently conducted to both quantify and identify each of the single alleles my mass differences. Also using a complex process starting from methylated DNA immunoprecipitation, and based on SYBR green based quantitative PCR of a plurality of DMRs, has been claimed to be able to accurately quantitate foetal cfDNA and use such quantitation from eg chromosome 21 DMRs, to prenatally diagnose trisomies (Papageorgiou et al 2011, Nat Med 4:510; WO 2012/092592); although technical concerns about such an approach to diagnose trisomies have been raised (Tong et al 2012; Nat Med 18:1327). High-throughout droplet digital PCR (ddPCR) has been described for absolute quantification of DNA copy number from normal and tumorous breast tissues, and also total and foetal cfDNA in maternal plasma using duplex probe-based quantitative PCR of RASSF1/RNaseP and RASSF1/beta-actin (Hindson et al 2011, Anal Chem 83:8604). Separate SYBR green quantitative PCR reactions of RASSF1A, SRY and DYS14 have been evaluated as an assay to detect RASSf1A to facilitate improved diagnostic reliability of NIPT (White et al 2012; PLOS ONE 7(9):e45073). However, generally considered as the "gold standard" for the quantitative measurement of foetal cfDNA against which other assays are often compared, remains the quantification of Y chromosome-specific genes (eg 5FY) of male foetuses eg, as used by Yu and co-workers to determine whether the increased foetal cfDNA in maternal serum level of gravitas developed into early-onset preeclampsia (Yu et al 2013, Int. J Mol Sci 14:7571).

Accordingly there is a need, from one or more of the above or perspectives, for improved methods to detect, preferably quantitatively, an amount of a species of DNA that originates from a particular cell type, such as a tumour-, foetal- or a placental cell, in particular to so detect cfDNA eg from the circulatory system of an individual.

Accordingly, it is an object of the present invention to provide alternative, improved, simpler, cheaper and/or integrated means or methods that address one or more of these or other problems. Such an object underlying the present invention is solved by the subject matter as disclosed or defined anywhere herein, for example by the subject matter of the attached claims.

Generally, and by way of brief description, the main aspects of the present invention can be described as follows:

In a first aspect, and as may be further described, defined, claimed or otherwise disclosed herein, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA,
wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

In another aspect, the invention also relates to a method for detecting an increased risk of an individual suffering from or developing a medical condition, said method comprising the steps:
(i) conducting a method of the first aspect of the invention, wherein each of the detection steps comprises quantitative detection; and
(ii) comparing the amount of said species of DNA detected with a threshold amount and/or a reference distribution of amounts,
wherein an increase in, or outlying of, the amount of said species of DNA indicates an increased risk of the individual suffering from or developing said medical condition.

In other aspects, the invention also relates to a composition, a kit and a computer program product, in each case as may be described, defined, claimed or otherwise disclosed herein, for use within or in connection with a method of the invention.

The figures show:

FIG. 3 depicts the correlation of the amount of male specific DNA (Y chromosomal-representation) to the foetal cfDNA fraction measured by a method of the present invention (Example 1) for study twin cases with known foetal genders.

FIG. 4 depicts the improved sensitivity of a method of the invention compared to foetal cfDNA fraction detected using separate reactions of a single DMR. The number of PCR cycles (Cp) required for detection of foetal cfDNA (Example 2) in a sample using either RASSF1A or TBX3 alone as a single DMR, or as a multiplex (using the same labels) of RASSF1A and TBX3.

FIG. 5 depicts a schematic representation of the operations conducted by a computer program product of the invention.

Figure 1:
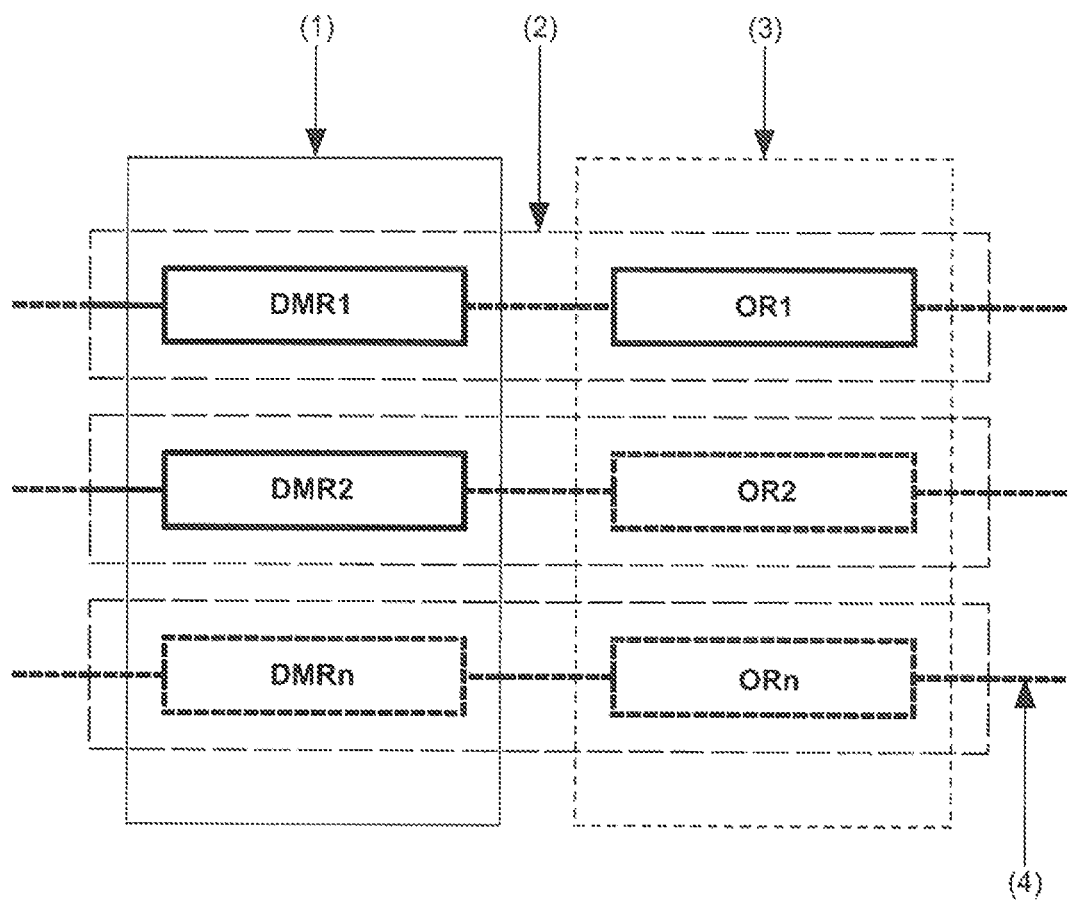
FIG. 1 depicts a schematic representation of the differentially methylated regions ("DMR") and other regions(s) ("OR") used in the method of the invention.

The present invention, and particular non-limiting aspects and/or embodiments thereof, can be described in more detail as follows:

In a first aspect, the invention relates to a method for detecting in a sample from an individual an amount of a species of DNA originating from cells of a given type, which sample comprises said species of DNA in admixture with differently methylated DNA not originating from cells of said type; said method comprising the steps:
(a) treating the DNA present in said sample with a reagent that differentially modifies methylated and non-methylated DNA;
(b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
(c) detecting an amount of total DNA present in said sample using at least one other region that is not differently methylated between said species of DNA and the DNA not originating from cells of said type, the modification of which region(s) by said reagent is insensitive to methylation of DNA,
wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

Terms as set forth herein are generally to be understood by their common meaning unless indicated otherwise. Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments. Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

In certain embodiments of the present invention, the individual is a human or a non-human animal, where such non-human animal may, in particular embodiments, be selected from the group consisting of: horse, sheep, cow, pig, chicken, mouse and rat. In a more specific embodiment, the individual is a pregnant female human or a human individual suspected of being at increased risk of developing or suffering (or suffering from) a medical condition, such as one or more of the medical conditions disclosed herein. Such a method of the present invention is not intended to be practiced on the human or animal body; for example it is intended to be practiced in an in-vitro manner.

In all aspects of the invention, the cell(s) of a given type may be a cell of a particular organ or tissues of the same individual. For example, the cell may be a tumour cell of the individual. Alternatively, such cell(s) may originate from a different individual or organism. For example, in the case of an individual being a pregnant female, the cell of a given type may be a cell of the foetus, including of the placenta of such foetus, and in other embodiments, the cell type may be an infectious agents such as a bacteria or a protozoa.

In certain embodiments of the present invention, said species of DNA and/or said differently methylated DNA is cell-free DNA, and in particular of such embodiments is circulating cell-free DNA. In one particular embodiment, said species of DNA and the differently methylated DNA that is admixed therewith are both circulating cell-free DNA. The term "cell-free DNA" (or "cfDNA") is art recognised, and includes the meaning of DNA that is found outside of a cell, such as in a biological fluid (eg blood, or a blood fraction) of an individual. "Circulating" is also an art-recognised term, and includes the meaning that an entity or substance (eg cfDNA) is present in, detected or identified in, or isolated from, a circulatory system of the individual, such as the blood system or the lymphatic system. In particular, when cfDNA is "circulating" it is not located in a cell, and hence may be present in the plasma or serum of blood, or it may be present in the lymph of lymphatic fluid.

The term "differentially methylated region" or "DMR" will be recognised by the person of ordinary skill in the art, and is also intended to refer to a region in chromosomal DNA that is differentially methylated (eg at a CpG motif) between said species of DNA and the other DNA with which it is admixed in the sample. For example in one embodiment, the DMRs used in the present invention are differentially methylated between foetal and maternal DNA, or are differentially methylated between tumour-derived and non-tumour-derived DNA from the same individual. In particular embodiments of the present invention, the DMRs are hypermethlyated in foetal DNA and hypo methylated in maternal DNA, or are hypermethylated in tumour-derived DNA and hypomethylated in DNA that is derived from non-tumour tissue of the individual. That is, in such regions exhibit a greater degree (ie more) methylation in said species of DNA (eg the foetal or tumour cfDNA) as compared to the other DNA (eg maternal or non-tumour DNA), such as about 10%, 20%, 30%, 40%, 50%, 60%, 70%, 80%, 90% or 100% or, or more of, the sites available for methylation at a given DMR are methylated in said species of DNA as compared to the same sites in the other DNA.

A reagent is used in the present invention that differentially (eg selectively) modifies methylated as compared to non-methylated DNA. For example, treatment of DNA with a reagent comprising bisulphite (bisulfite) converts cytosine residues to uracil, but leaves 5-methylcytosine residues unaffected. Thus, bisulphite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information, including the use of PCR primers and/or probes that can distinguish between such singe-nucleotide changes.

Such a reagent may alternatively (or in addition) comprise a restriction enzyme that is sensitive to the DNA methylation states. Cleavage Of such a restriction enzyme's recognition sequence may be blocked, or impaired, when a particular base in the enzyme's recognition site is modified, eg methylated. In particular embodiments of all aspects of the invention, the reagent comprises a methylation-sensitive restriction enzyme, such as a methylation-sensitive restriction enzyme disclosed herein, including such embodiments that comprise two, three, four, five or more of such methylation-sensitive restriction enzymes.

Prior to step (a), the sample may be processed to isolate, enrich and/or purify, the DNA present therein. For example, a plasma sample may be processed using a cfDNA isolation process or kit to provide a (non-natural) subsequent solution that comprises an admixture of said species of DNA together with the differentially methylated DNA that does not originate from the cell-type. The step of treating in (a) may comprise the step of adding a separate solution that comprises said reagent (eg a methylation sensitive restriction enzyme) to the admixed DNA of the sample (eg, to a non-natural solution comprising such admixed DNA); and/or may comprise maintaining (or changing to) certain conditions. In particular, when said reagent comprises one or more methylation sensitive restriction enzyme, the step of treating in (a) may comprise incubating the DNA and the enzyme(s) together at about 37° C. for between about 5 min and 300 min, such as between about 30 min and 90 min or about 60 min, and optionally may comprise a step of incubating such mixture at a higher temperature (for example, between about 50° C. and 90° C. such as about 80° C.) so as to deactivate the enzyme(s). In certain embodiments, the composition formed for a treating step of (a) may be non-naturally occurring. For example, particular salts of components of the solution (or buffer); and/or the mixture of (eg human) cfDNA together with one or more bacterial-derived restriction enzymes (or a non-natural mutant thereof) may be a non-natural composition or mixture.

In contrast, an "other region" ("OR") used in the present invention is not (significantly) differentially methylated between said species of DNA and other DNA with which it is admixed in the sample. For example, under the conditions and nature of the reagent used, there is not detectable difference between modification by such reagent at the other region of said species of DNA (eg foetal DNA) as compared to the other region of the admixed DNA (eg the maternal DNA). Such a non-difference may be achieved if the other region comprises no sites for methylation, if there is no difference in the degree of methylation if such sites are present or by the use of a reagent that does not recognise any sites of methylation present in the other region. In particular embodiments, the other region used in the present invention (that is not so differentially methylated) may be non-over-lapping with the DMRs used in the present invention. For example, the other region can be located further than about 10 bp, 20 bp, 50 bp, or more than 100 bp, 500 bp, 1 kb or 10 kp, away from either of the DMRs.

One feature of the present invention is that the detection of the various DNA regions, ie the DMRs and the other region(s), occurs in a simplified process. For example, using a single aliquot of DNA from the sample, such DNA regions are detected in a single vessel. This feature simplifies the method, and can provide for more efficient: and accurate detection (especially in those embodiments when detection is quantitative). The term "vessel" will be art recognised, and includes embodiments of a vessel (such as a tube, well of a microtitre plate, nano-well, capillary reaction vessel etc) in which a process or procedure comprised in the method occurs, such as a reaction and/or detection process or a step of a method of the present invention. Other such vessels may include droplets in oil/water emulsions, nanoparticles or a hybridisation chamber; as appropriate to the detection technology used. The detectable labels used, in such methods is the same for each DMR and, in certain embodiments, is the same for each other region, provided that the label(s) used for the other region(s) is different (ie, can be separately detected) to the label(s) used for the DMRs. Detectable labels that are "the same", can also include labels while structurally different, are functionally (essentially) similar as they cannot be significantly differentiated by the detection technology employed. For example, structurally different fluorescent dyes may be considered "the same" if their excitation and emission spectra are (substantially or essentially) similar, or overlap to such a degree that they are able to be excited and detected simultaneously with the same wavelength(s). Suitable labels (and detection modalities) are further described elsewhere herein. In addition, the detection of the DMRs and other region(s) is made effectively simultaneously. For example, within the same (reaction/detection) vessel, all such regions (and hence said species of DNA and total DNA) can be detected within less than about 5 s, 1 s, 0.5 s, 100 ms, 10 ms, 1 ms, 100 us, 10 us or 1 us of each other, and for example without transferring the vessel, or the reaction/mixture, to any subsequent vessel, assay or equipment, or for example, without adapting or recalibrating the detection process for either of the DMRs or the other region(s) separately. The use of two different detectable label(s)—one for said DMRs and one for the other region(s)—utilises components, process and/or steps that are non-natural. For example, a composition of two specific labels together with the specific DNA regions would (generally) not be found in nature. In particular, short probes used in quantitative probe-based PCR, while may comprise a DNA sequence that is a fragment of that found in a natural genome, when linked to a one or more labels (such as a fluorescent dye) form a specific labelled fragment that is non-natural.

Collectively, the features of the present invention provide for certain advantages over prior art methods. These can include sensitive detection of methylation (and hence the species of DNA to be detected) and/or accurate quantification of the amount of said species of DNA by reference to the amount of total DNA detected within the same assay, from the same aliquot of admixed DNA and effectively simultaneously with the detection of the two or more DMRs, and optionally using a co-located other region.

By way of graphical description, a schematic representation of the general arrangement of the DMRs, the other region(s) and the detectable label(s), as used for the present invention, is presented in FIG. 1. (1) The presence of methylation in DNA at two or more DMRs, DMR1 and DMR2 (and, optionally, up to DMRn), is in each case detected using the same detectable label(s). (2) Optionally, an other region ("OR") is located within the same portion of the genome (eg, between about 20 bp and about 20 kb upstream or downstream of) one of the DMRs. (3) The amount of total DNA detected using at least one OR (OR1, and optionally, OR2 or up to ORn) is detected using different detectable label(s) to those used to detect methylation at the DMRs (optionally, the detectable label(s) used is the same for all the ORs). (4) Optionally, methylation at more than two DMRs is so detected, and/or the amount of total DNA is detected at more than one OR.

In certain embodiments, poor to or as part of the detection that occurs as part of a step (b) and/or a step (c) of any method of present invention, each DNA region comprising said DMRs and/or said other region(s), respectively, is(are) amplified. Amplification of DNA may be conducted using any suitable replication process, and in particular of such embodiments, each of the DMRs and/or an other region, is amplified by a polymerase chain reaction (PCR) using primers suitably designed for each DMR and/or other region. The person of ordinary skill will readily be able to design such PCR primers for use in the method of the invention, for example by use of primer design algorithms and programs such as Clone Manager Professional 9 (Sci-Ed Software), Vector NTI (Life Technologies), or web-based tools such as those found from www.ncbi.nim.nih.gov/tools/primer-blast/ or molbiol-tools.ca/PCR.htm. Those embodiments of the present invention that comprise PCR amplification can further comprises specific steps that are related to the practice of PCR, such as any of those described herein, or in particular the steps of: (A) providing a reaction mixture comprising a double-stranded target DNA, a pair of primers (for example, a pair of primers disclosed herein) designed to amplify a region of such DNA (such as a DMR or an other region as described herein) wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; (B) heating the reaction mixture to a first predetermined temperature for a first predetermined time to separate the strands of the target DNA from each other; (C) cooling the reaction mixture to a second predetermined temperature for a second predetermined time under conditions to allow the first and second primers to hybridise with their complementary sequences on the first and second strands of the target DNA, and to allow the Taq polymerase to extend the primers; and (D) repeating steps (B) and (C) at least 20 times.

In other embodiments, a detectable label used in step (b) and/or step (c) of a method of the invention is independently selected from the group consisting of: fluorescent, protein, small molecule or radioactive label. For example, fluorescent labels that are the same (including, by having similar or overlapping excitation and/or emission spectra) may be used for the DMRs, and a fluorescent label that has an excitation and/or emission spectra (in particular, a different emission spectrum) may be used for detection of the other region(s). The person of ordinary skill will be able to select appropriate such fluorescent label(s) for use in the present invention from, for example, the group consisting of: FAM, TET, JOE, VIC, HEX, NED, PET, ROX, TAMRA, Quasar and Texas Red. In other embodiments, a detectable label may be a protein or small molecule tag that, for example, can be detected using a specific antibody and ELISA-type detection approaches. The use of the same protein or small molecule for each of the DMRs, and a defectably different protein or small molecule for the other region(s), may also be utilised for the detectable label(s) used in the present invention. Different radioactive labels may be distinguished by their emission energy, penetration/excitation characteristics and particle-type (for example, by distinguishing between alpha and beta particles). Other detectable labels (such as nucleic-acid coded tag) may also be employed in the present invention.

In particular embodiments, the detection in step (b) of a method of the example comprises real-time quantitative probe-based PCR, eg by using at least two labelled probes, each of which is specific for one of said DMRs, PCR amplification of said two or more DMRs m the same reaction can be considered as "multiplex" (or "duplex" if only two DMRs are so amplified). Likewise, the detection in step (c) in the methods of the invention may, in addition or alternatively, comprise real-time quantitative probe-based PCR, such as by using at least one labelled probe specific for one of said other region(s).

The term "probe-based" quantitative PCR is art recognised, and encompasses various embodiments described and marketed under different brand names (such as "TaqMan" PCR of Roche), and uses a (eg fluorescent) reporter probe that is specific for the detection of a given amplicon (eg a DMR or an other region). Probe-based quantitative PCR is distinct from quantitative PCR using double-stranded DNA-binding dyes (eg SYBR Green) as reporters, as such double-stranded DNA-binding dyes bind non-specially to any double-stranded amplicon and eg cannot be used to distinguish between detection of the DMRs (ie said species of DNA) from detection of the other region(s) (ie detection of total DNA). As the person of ordinary skill will appreciate, a specific amplicon of PCR may be detected using a single probe or by using multiple probes (such as two or three probes) for an amplicon.

Such probe-based quantitative PCR may be conducted in an analogue-approach, using a machine such as a LightCycler in which the intensity of signal (eg over time) is measured and used to quantitatively determine detection. Alternatively, digital PCR (dPCR), ie, PCR conducted in multiple events so as to determine the number of amplification events as method to quantitate an amount of detected DNA. For example, dPCR that is conducted in nano-wells or droplets (ddPCR).

The person of ordinary skill will be able to design suitable primers and probes (and with suitable labels, eg dyes) for probe-based quantitative PCR detection of the DMRs and/or other regions(s); for example by using primer/probe design software as described elsewhere herein. As will be known, the PCR primers may overlap methylation site(s) specific for the methylation-specific modifying reagent used in the methods, in particular when the reagent comprises one or more methylation sensitive restriction enzyme, such as one (or a combination thereof) as disclosed herein. In particular such embodiments, one or other (or when considered together, both) of the PCR primers for a given DMR may overlap two or three such methylation sites (such as two or three restriction sites for methylation-sensitive restriction enzymes, each of which may comprise, or comprises, a methylation site). Alternatively or in addition, the primers for a DMR may be designed to flank one, two, three or more such methylation sites, such as up to 10, 15, 20, 25 or 50 such methylation sites, in particular flanking restriction sites for one, two, three or more such methylation sites, such as up to 10, 15, 20, 25 or 50 methylation-sensitive restriction enzymes, each of which may comprise, or comprises, a methylation site.

In a particular embodiment, the genomic location of the other region used in the present invention is generally located in the same portion of the genome, such as between about 20 bp and about 2.0 kb upstream or downstream of (including embodiments within the same gene as) the genomic location of at least one of the DMRs used herein. In certain embodiments, the other region does not overlap with the DMR. The inventors find that detection (and particularly quantification) of the species of DNA is enhanced (eg, in terms of sensitivity, accuracy and/or precision) if the other region is so located in the same portion of the genome as one of the DMRs. Without being bound by theory, it is believed that with such similarly-located DMR(s) and other region, the effect of variation in chromatin/nucleosome packing across the genome—and hence stability/degradation of different regions of genomic DNA—is mitigated, such that any difference in stability/degradation of a DMR (ie detecting the species of DNA) as compared to rise other region (is detecting total DNA) is less, and hence a relative (and absolute) quantification may be made without it being (significantly) confounded by quantitative differences brought about by (significantly) differential chromatin/nucleosome packing across the genome between a DMR and an other region. The combination of this feature (similarly-located DMR(s) and other region) with another feature of the present invention (the use of at least two DMRs, and the detection in step (b) and the detection in step (c) are made using the same aliquot of DNA of the sample, and in the same reaction/detection vessel, and effectively simultaneously for such DMRs and other region, and using: (x) the same detectable labels(s) for each of said DMRs; and (y) a different detectable label for said other region(s)), is a preferred embodiment of the present invention. The use of such a combination of features in the present invention provides opportunity for efficiency improvements and/or synergistic enchantment of outcome. For example, an improved sensitivity and/or accuracy and/or precision of detection (eg, detection of a quantitative amount) or said species of DNA can be obtained by the use of such a combination; the degree of improvement of which can be synergistic, as compared to the use of each feature alone; eg the enhancement obtained by use of the combined features being greater than the sum of each enhancement obtained by the use of each feature individually.

The present invention includes the use of one other region to provide for the detection of an amount of total DNA in the admixture. However, the present invention also encompasses embodiments that use more than one other region. For example, the invention includes such embodiments wherein said detection in step (c) comprises using at least two of said other regions, such as two, three or four of said other regions. In particular embodiments of all aspects of the present invention, the number of said other regions is the same as the number of DMRs used in step (b). For example, if two DMRs are used then two other regions are used in such an embodiment, and if three DMRs are used then three other regions are used (such as depicted in FIG. 1).

As described elsewhere herein, certain embodiments of the present invention include where the other region is generally located in the same portion of the genome, such as between about 20 bp and about 20 kb upstream or downstream of (including embodiments within the same gene as) the genomic location of at least one of the DMRs used herein. In certain embodiments, the other region does not overlap with the DMR Accordingly, if multiple other regions are used in the present invention, then embodiments are included where two or more of such other regions are similarly located in the genome to the two or more DMRs. For example, one of said other regions may be located between about 20 bp and about 20 kb upstream or downstream of (including embodiments within the same gene as) a DMR used in step (b) and each other of the said other regions (eg, a second other region) is located between about 20 bp and about 20 kb upstream or downstream of (including embodiments within the same gene as) another of said (eg, non-overlapping) DMRs (eg, the second DMR). In certain embodiments an additional other region, may overlap with a DMR.

An other region used in the present invention, when generally located in the same portion of the genome as a DMR, may be located upstream or downstream of one of said DMRs within a distance selected from the group consisting of: between about 16 Kb to 20 bp, 14 kb to 20 bp, 12 kb to 20 bp, 10 kb to 20 bp, 8 Kb to 20 bp, 6 kb to 20 bp, 5 kb to 20 bp, 4 kb to 20 bp, 3 kb to 2 bp, 16 kb to 20 bp, 1 kb to 20 bp, 500 bp to 20 bp, 200 bp to 20 bp, 20 kb to 15 kb, 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, 2 kb to 500 bp, 1 kb to 100 bp, 500 bp to 50 bp, 400 bp to 200 bp and 500 bp to 100 bp. In particular embodiments, each other region used in the present invention is so generally located to a different of the DMRs used.

If multiple other regions are used, then the present invention includes embodiments where the detection in step (c) is made using the same detectable label for each of said other regions and/or comprises multiplex real-time quantitative PCR using at least two labelled probes each of which is specific for one of said other regions.

In particular embodiments, all detection steps (ie, those required for all DMRs and all other regions) are conducted in an efficient and effective manner using multiplex quantitative probe-based (eg TaqMan) PCR, in one process step or reaction. For example, the detection in step (c) and said detection in step (b) are made using the same aliquot of DNA of said sample, and in the same reaction/detection vessel, and effectively simultaneously with each other, and by multiplex real-time quantitative PCR using at least one labelled probe specific for each of the said DMRs and other region(s). In particular of such embodiments, the reagent comprises one or more methylation sensitive restriction enzyme, such as one (or a combination thereof) as disclosed herein.

The present invention may also include further procedures, such as one or more control procedures. For example, the present invention can include one or more steps directed to the detection of a third class of DNA region that acts as a control for the modification step (eg, as a control for restriction enzyme digestion). Such embodiments may, for example, also be conducted using multiplex real-time quantitative probe-based PCR wherein such control region is amplified and detected by a third set of primer/probe(s) with a third detectable label used for such class of region.

In one embodiment of the present invention of particular relevance, said species of DNA originates from cells of a foetus and/or the placenta of a foetus and said sample is from a pregnant female. In such embodiments, the sample may be obtained in a non-invasive manner. For example, said species of DNA is circulating cell-free DNA that has been detected from the sample being blood or a blood fraction (such as plasma or serum) that has been obtained from the pregnant female by conventional means such as a blood collection tube.

The present invention includes embodiments where the DMRs are hypermethlyated in foetal DNA and hypo methylated in maternal DNA. In certain embodiments, such a DMR may be located in a promoter, enhancer region or an exon of a gene, such as a gene disclosed herein. Alternatively, a DMR may be located in an intron of such a gene, or in a non-coding region of the genome. In particular embodiments of all aspects of the present invention, such genome and/or gene is a human genome or gene. Specifically included in the present invention are embodiments wherein said DMRs comprises at least one, preferably at least two, methylation site(s) specific for said reagent, and at least one of said DMRs is located in a portion of the genome and/or gene (eg a human genome or gene) that is RASSF1A and/or TBX3, or selected from the group consisting of: RASSF1A, TBX3, HLCS, ZFY, CDC42EP1, MGC15523, SOX14 and SPN. Also, embodiments are included wherein said DMRs comprises at least one, preferably at least two, methylation site(s) specific for said reagent, and at least one of said DMRs is located in a region and/or gene selected from the group consisting of: AIRE, SIM2, ERG, VAPA-APCDDI, one disclosed in WO 2011/034631 as being hypermethylated in foetal DNA relative to maternal DNA (eg, SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and/or 261 of WO 2011/034531) and one disclosed in WO 2011/092592 (eg, EP1, EP2, EP3, EP4, EPS, EP6, EP7, EP8, EP9, EP10, EP11 and/or EP12 of WO 2011/092592, as further investigated in Lim et al 2014, BMC Medical Genomics 7:1).

In particular embodiments of all aspects of the present invention, the two DMRs used are not located in the same portion of the genomic and/or gene. For example, such DMRs may be located on separate chromosomes, or separated by more than about 20 kb, or more than about 15 kb, 10 kb, 8 kb, 6 kb, 4 kb, 2 kb, 1 kb, 500 bp or 200 bp. Alternatively, it is envisioned, that the two (or more) DMRs used in the present invention may, in certain embodiments, be located in the same region or gene (such as one described herein) and, further, may overlap with each other.

In particular embodiments of the present invention, both of said DMRs are (or each, in the case of more than two DMRs are being used, is) located in a portion of the genome and/or gene (preferably that is human) that is RASSF1A and/or TBX3, or is selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A (NCBI Reference Sequence: NG_023270.1: Homo sapiens Ras association (RalGDS/AF-6) domain family member 1 (RASSF1), RefSeqGene on chromosome 3; SEQ ID NO.: 13) or about positions 1,660 bp and 2,400 bp of TBX3 (NCBI Reference Sequence: NG_008315.1: Homo sapiens T-box 3 (TBX3), RefSeqGene on chromosome 12; SEQ ID NO.: 14). In a more particular embodiment, two (or more) DMRs are used, and a first DMR comprises one located between about positions 4,000 bp and 5,600 bp of RASSF1A and a second DMR comprises one located between about positions 1,650 bp and 2,400 bp of TBX3.

In particular embodiments, a DMR is located in RASSF1A between about positions 4,900 bp and 5,500 bp, 5,000 bp and 5,400 bp, or 5,100 bp and 5,300 bp of RASSF1A; and/or is located in TBX3 between about positions 1,800 bp and 2,260 bp, 1,920 bp and 2,160 bp or 1,920 bp and 2,080 bp of TBX3.

Figure 2:
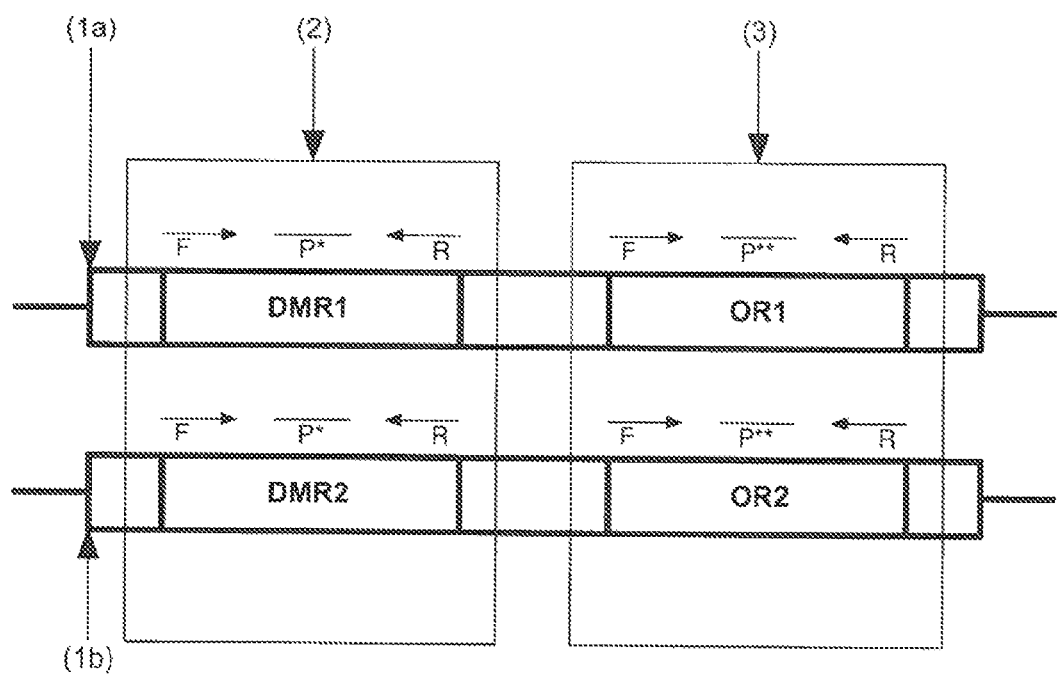
FIG. 2 depicts a schematic representation of the differentially methylated regions ("DMR") and other regions ("OR") used in Example 1.

The general arrangement of the DMRs and other regions ("OR") used in one embodiment of the present invention, is graphically represented by FIG. 2: (1a) DMR1 is found in exon 2 of RASSF1A and OR1 is located within exon 4 of RASSF1A, with DMR1 located between positions 50,340,672 bp and 50,340,784 bp and OR1 located between positions 50,331,604 bp and 50,331,702 bp of the RASS1A genomic sequence (NCBI Reference Sequence: NC_000003.12 Homo sapiens chromosome 3, GRCh38 Primary Assembly), separating DMR1 and OR1 by a distance of 8,969 bp. (1b) DMR2 is found in the promoter region of TBX3, with DMR2 located between positions 114,687,095 bp and 114,687,189 bp and OR2 is located between positions 114,676,384 bp and 114,676,454 bp of the TBX3 genomic sequence (NCBI Reference Sequence: NC_000012.12 Homo sapiens chromosome 12, GRCh38 Primary Assembly), separating DMR2 and OR2 by a distance of 10,640 bp. (2) Methylation in DNA at the two DMRs is detected using probe-based quantitative PCR using the respective forward (F) and reverse (R) PCR primers and region-specific probes, each probe labelled with the same labels (P*). (3) Total DNA is detected at two ORs using probe-based quantitative PCR using the respective forward (F) and reverse (R) PCR primers and region-specific probes, each probe labelled with the same labels for the ORs that is different to the labels used for the two DMRs (P**). Details of primer and probe sequences and probe labels are set out in TABLE 1.

The term "methylation site(s)" will be art-recognised, and has a meaning that encompasses, for example, a CpG motif within a short nucleotide sequence (eg one that is 4, 6, 8, 10 or 12 bp in length) that is, preferably, recognised by a methylation-sensitive restriction enzyme, such as one disclosed elsewhere herein.

Analogously, the other region may be located in particular portions and/or genes of the genome, and may be located in a promoter, enhancer region or an exon of a gene, or alternatively, located in an intron of such a gene, or in a non-coding region of the genome. In particular embodiments of all aspects of the present invention, such genome and/or gene is a human genome or gene. In particular embodiments, an other region used in the present invention is located in a (eg human) housekeeping gene (such as GAPDH, beta-actin, ALB, APOE or RNASEP). Alternatively (and in particular when said species of DNA is foetal cfDNA), said other region may be located in the same portion of the genome and/or gene that feature one or more DMRs (such as those RASSF1A, TBX3, HLCS, ZFY, CDC42EP1, MGC15523, SOX14 or SPN), and preferably does not overlap with a DMR used in the invention. In particular embodiments, said other region comprises a portion of the genome without a methylation site specific for said reagent, and said other region is located in the (eg human) genes RASSF1A or TBX3 (eg SEQ ID NOs: 13 and 14 respectively), and includes more particular embodiments wherein two or more of said other regions are used in detection step (c) and the first other region is located between about positions 14,220 bp and 13,350 bp of such RASSF1A and the second other region is located between about positions 12,400 bp and 13,000 bp of such TBX3. In particular embodiments, an other region is located in RASSF1A between about positions 14,230 bp and 14,340 bp, 14,230 bp and 14,330 bp, 14,230 bp and 14,320 bp, or 14,230 bp and 14,310 bp of such RASSF1A; and/or is located in TBX3 between about positions 12,400 bp and 12,940 bp, 12,700 bp and 12,850 bp or 12,710 bp and 12,790 bp of such TBX3. Alternatively, an other region may be located in an exon such as between about positions 13,790 bp and 13,880 bp, or 14,490 bp and 14,600 bp of such RASSF1A, or between about positions 8,040 bp and 8,180 bp or 6,230 bp and 6,350 bp of such TBX3; or an other region may be located in an intron such as between about positions 10,500 bp and 11,90 bp of such RASSF1A, or between about positions 10,000 bp and 11,000 bp of such TBX3.

There is now strong evidence that the level of foetal cfDNA (and/or total cfDNA) present in the circulatory system (eg in plasma) of a pregnant female is a marker of one or more forms of preeclampsia, such as early-onset preeclampsia, mild and/or severe preeclampsia (see Hahn et al 2011, Placenta 32(Supl):S17). The present invention shows particular utility in the efficient, effective, sensitive and/or low-variability detection/quantification of foetal cfDNA present in plasma of pregnant females, and the present invention has particular utility therein. Accordingly, in particular embodiments of the present invention, the individual is a pregnant female and is susceptible to suffering or developing a pregnancy-associated medical condition; particularly where said pregnancy-associated medical condition is preeclampsia. As used herein, an individual "susceptible to" a medical condition may alternatively be described as "is suspected to" or to "be considered at risk of being susceptible to" suffering or developing a medical condition; and in certain embodiments, the present invention is used to screen and/or diagnose the individual for susceptibility to, risk of suffering or developing, or suffering from or developing, a medical condition.

In alternative embodiments, the individual is a pregnant female and is susceptible to (or considered at risk of being susceptible to) suffering or developing a pregnancy-associated medical condition selected from the group consisting of: preterm labour, intrauterine growth retardation and vanishing twin. In particular, the inventors were surprised that the sensitivity of the present invention was such that discrepancies between cfDNA levels determined by the method of the invention and that determined by counts of Y-chromosome sequences as determined by massively parallel sequencing approaches, was useful in identifying one or more cases of a vanishing twin in (mixed-sex) twin pregnancies that previously were believed to be singleton pregnancies, and/or to follow the relative development and health of one or other of such (mixed-sex) twin pregnancies. The present invention may also be utilised in gender determination of twin pregnancies, by consideration of the relative values for foetal cfDNA compared to counts of Y-chromosome sequences determined from cfDNA (eg by using parallel sequencing approaches). In these regards, it should be noted that approaches that use massively-parallel sequencing of random cfDNA in maternal blood typically always count a very low frequency of "Y-chomomosone" sequences (such as between about 0.003% and 0.004% of all sequences, or between about 0.0015% and 0.01% or 0.002% and 0.005% of all sequences) in all female pregnancies due to homology of certain Y-chromosome short sequences to other chromosomes. A cut off "Y-chromosome" sequence counts of about 0.005%, or between about 0.003%, 0.004%, 0.006% or 0.007%, may therefore be employed for female samples.

As described elsewhere herein, there is also increasing evidence that the presence and amount of methylated DNA at certain DMRs Is indicative or prognostic of certain medical conditions that are not associated with pregnancy. Accordingly, in another particular embodiment of the present invention, said species of DNA originates from a cell type associated with such a medical condition, particularly in those embodiments where said species of DNA is circulating cell-free DNA and said sample is a blood fraction such as plasma or serum. For example, the medical condition may be a cell proliferative disorder, such as a tumour or cancer. In particular embodiments, the medical condition is a tumour or a cancer of an organ selected from the list consisting of: liver, lung, breast, colon, oesophagus, prostate, ovary, cervix, uterus, testis, brain, bone marrow and blood; and/or said species of DNA may originate from cells of a tumour; particularly where such tumour is a carcinoma or cancer of an organ selected from the group consisting of: liver, lung, breast, colon, oesophagus, prostate, ovary, cervix, uterus, testis, brain, bone marrow and blood.

When used in the context of a medical condition being a tumour or cancer, the present invention includes embodiment wherein said DMRs comprises at least one, preferably at least two, methylation site(s) specific for said reagent, and at least one of said DMR is located in a portion of the genome and/or a gene (in particular, when such genome and/or gene is a human genome or gene) selected from the group consisting of: a tumour suppressor gene, p16, SEPT9, RASSF1A, GSTP1, DAPK, ESR1, ARC, HSD1784 and H1C1. In particular, one of said two or more DMRs may be located in RASSF1A (eg SEQ ID NO. 13) such as located between about positions 4,700 bp and 5,600 bp of such RASSF1A; and/or said other region is located between about positions 14,220 bp and 13,350 bp of such RASSF1A. Other particular locations of the DMRs and/or other region(s) within RASSF1A for use in this embodiment are disclosed elsewhere herein. Furthermore, the person of ordinary skill will now recognise that other DMRs and/or other regions located in other portions of the genome of in other genes may be identified from the relevant scientific literature (eg, for review, see Elshimali 2013). In particular when used in the context of a medical condition being a tumour or cancer, the present invention includes embodiments where at least one other region (preferably two or more) are located in a (eg human) housekeeping gene (such as GAPDH, beta-actin, ALB, APOE or RNASEP). Alternatively for such context, said other region(s) may be located in the same portion of the genome and/or gene that feature one or more DMRs (such as those p16, SEPT9, RASSF1A, GSTP1, DAPK, ESR1, APC, HSD17B4 and H1C1).

In yet another particular embodiment of the present invention, said species of DNA originates from a cell type associated with a medical condition selected from the group consisting of: an infection/infectious disease, a wasting disorder, a degenerative disorder; an (auto)immune disorder, kidney disease, liver disease, inflammatory disease, acute toxicity, chronic toxicity, myocardial infarction, and a combination of any of the forgoing (such as sepsis) and/or with a cell proliferative disorder, particularly in those embodiments where said species of DNA is circulating cell-free DNA and said sample is a blood fraction such as plasma or serum. For example, the medical condition may be an infection/infectious disease, such as one caused by s bacterial, viral or protozoan pathogen, including a pathogen selected from the group consisting of: a retrovirus (such as HIV), a herpes virus (such as HSV, EBV, CMV, HHV or VSV), dengue virus, mycobacteria (eg Mycobacterium tuberculosis), and hantavirus. In certain embodiments, the medical condition is sepsis and/or excludes kidney disease.

In all aspects of the present invention, there exist embodiments wherein the sample is a tissue sample or a sample of biological fluid. In particular, the sample is whole blood or a blood fraction (eg, such as plasma or serum). In alliterative embodiments, the sample is biological fluid selected from the group consisting of: urine, saliva, sweat, ejaculate, teats, phlegm, vaginal secretion, vaginal wash and colonic wash. In more particular embodiments, the sample is a plasma or serum sample from the individual, or is urine from the individual in other embodiments, the sample is largely (or essentially) free from cells, and/or is not a whole blood and/or ejaculate sample. In certain embodiments, the sample is not ejaculate if the individual is female and the sample is not a vaginal wash if the individual is male.

In all aspects of the present invention, the reagent that differentially modifies methylated end non-methylated DNA may comprise bisulphite and/or an agent that selectively digests unmethylated over methylated DNA (for example, such agent may digest unmethylated DNA but not methylated DNA). In particular embodiments, the reagent agent comprises: at least one methylation sensitive enzyme; at least one methylation sensitive restriction enzyme; and/or an agent selected from the group consisting of: AatII, AciI, AclI, AfeI, AgeI, AgeI-HF, AscI, AsiSI, AvaI, BceAI, SmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmiI, PvuI, PvuI-HF, RsrII, SacII, SalI, SalI-BF, SfoI, SgrAI, SmaI, SnaBI, TspMI and ZraI. In particular embodiments, said reagent is one selected from the group consisting of; BstUI, HhaI and HpaII.

In related embodiments, the reagent may comprise two or more of any of the reagents disclosed herein. For example, it may comprise two, three, four, five or more (eg up to seven, eight or ten) methylation sensitive restriction enzymes, including a reagent comprising or essentially consisting of two or three of the methylation sensitive restriction enzymes selected from the group consisting of: BstUI, HhaI and HpaII.

The use of bisulphite or methylation-sensitive restriction enzymes to study differential methylation will be well known to the person of ordinary skill, who may apply teachings of standard texts or adaptation of published methods such as Poon et al (2002), Nygren et al (2010) or Yegnasubramanian; et al (2006, Nuc Acid Res 34:e19). By way of illustration, the inventors provide examples herein that employ the use of methylation-sensitive restriction enzymes as the reagent that differentially modifies methylated and non-methylated DNA. For further illustration using bisulphite as reagent, it will be apparent to the person of ordinary skill that bisulphite-modified DNA methylation sites may be detected using eg methylation-specific PCR (such as using primers and/or probes that selectively bind to the bisulphite-modified sequences) and/or by the subsequent use of restriction enzymes the recognition site of which is created upon such bisulphite-modification.

In particular embodiments of all aspects of the invention, a quantitative amount of said species of DNA (and/or or said total DNA) is to be detected and/or determined. Accordingly in such embodiments, one or more (eg each) of said detection steps comprises quantitative detection and said detected amount of said species of DNA is expressed as a relative concentration of said species of DNA to the total DNA present in said sample.

If an absolute amount of total DNA is known, then correspondingly an absolute amount (for example, as represented by a concentration such as ug/ml or genome-equivalents such as Eg/mL) of the species of DNA can be determined from such relative concentration. An absolute amount of total DNA for a sample may be determined, for certain embodiments, by including the further steps of: detecting an amount of total DNA in a standard sample of DNA of known amount using the same other regions(s) as used in step (c); and comparing the signal detected from said standard sample of DNA to the signal detected in step (c). Such a standard sample of DNA (of known amount/concentration) is readily available from commercial sources, and especially if prepared and analysed using a dilution series, can readily and efficiently be used to determine (by Interpolation/estimation from the standard curve) an absolute amount of total DNA present in the sample. Practically, such standard curve may be prepared and analysed essentially as described for the other regions (but in a separate set of standard vessels/reactions), preferably in the same run as the detection of the DMRs/other region(s); and may even use the same reaction master-mix. Accordingly, while the "DMRs" of the DNA control may be detected for such standard DNA, such a signal is not required to generate a standard curve. Accordingly, if the signal from a such a standard DNA sample is used to compare, the in certain embodiments where each of said detection steps comprises quantitative detection, said detected amount of said species of DNA can be expressed as an absolute amount of said species of DNA in said sample.

A determined quantitative amount of said species of DNA has utility in assessing the risk of the individual to certain medial conditions and/or if there is sufficient of such species of DNA in the sample to enable further analysis of such species of DNA to be conducted efficiently, accurately and/or in a cost effective manner.

Accordingly, certain embodiments of the present invention further include the step of: comparing the amount of said species of DNA detected with a threshold amount and/or reference distribution of amounts, wherein an increase in the (or outlying) amount of said species of DNA indicates an increased risk of the individual suffering from or developing a medical condition. Threshold amounts and/or a set of amounts to form a reference distribution may be obtained from published literature and or empirical studies. For example, using published threshold values (Papantoniou et al 2013. Prenat Diag 33:682) if the total cfDNA exceeds an amount of about 7,500 Eg/mL plasma or if the foetal cfDNA fraction exceeds an amount of about 500 Eg/mL plasma, then the woman may be determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts such as those determined from low-risk women or those which did not suffer from or develop preeclampsia, for example if the foetal cfDNA fraction fells within the $90^{th}$ percentile of such a distribution, then the woman may be considered to have an increased risk of suffering mild or severe preeclampsia (Jakobsen et al 2013, Transfusion 53:1956). Other relevant factors may be considered in determining a suitable threshold amount. For example, a pregnant women who is also suffering from breast cancer, may have a higher bias of methylation at RASSF1A present in her plasma due to both factors.

Analogously, certain embodiments of the present invention further include the step of: comparing the amount of said species of DNA detected with a threshold amount and/or reference distribution of amounts, wherein an amount of said species of DNA in excess to said threshold (or is not an outlier compared to said population) indicates that a diagnosis for an abnormality in the said species of DNA present in said sample may be performed on, preferably a separate aliquot of DNA of, said sample. For example, if foetal cfDNA fraction is greater than about 10%, 9%, 8%, 7%, 6%, 5%, 4%, 3%, 2%, 1% or 0.5% of total cfDNA present in maternal plasma, then there would be sufficient fraction or foetal cfDNA to effectively conduct a subsequent test to investigate one or more characteristics of the foetal cfDNA, for example to investigate the chance or existence of a chromosomal anomaly of mutation comprised within such foetal cfDNA (such as using NIPT based on massively parallel sequencing). In the case of twin pregnancies, the inventors determine that a minimum foetal fraction of cfDNA for NIPT of a twin pregnancy could be considered to be 8%, or about 5%, 6%, 7%, 9% or 10%, and for monochorionic twin pregnancies with concordant genotypes (apart from rare exceptions, Chen et al, 2013, Am J Med Genet A, 161A:1817), a foetal cfDNA fraction of 4%, or about 2%, 3% or 5%, would be sufficient.

Therefore, the present invention also includes embodiments where comprising a further step of: performing on, preferably with a separate aliquot of DNA of, said sample an in-vitro diagnosis for an abnormality in said species of DNA present in said sample; preferably wherein, said species of DNA originates from cells of a foetus and/or the placenta of a foetus, said sample is from a pregnant female and said diagnosis is a prenatal diagnosis. Such diagnosis directed at said species of DNA present may comprise a step that uses a detection technology selected from the group consisting of: DNA sequencing, SNP analysis, digital PCR and hybridization, and in particular embodiments said detection technology is massively parallel sequencing of DNA, such as massively parallel sequencing of random and/or (exon) enriched DNA.

Such a diagnosis or test may be directed at the foetal DNA to identify a genetic mutation or chromosomal abnormality of the foetal DNA. Accordingly in certain embodiments, said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder, in particular such embodiments, the genetic mutation is selected from the group consisting of; colour blindness, cystic fibrosis, hemochromatosis, haemophilia, phenylketonuria, polycystic kidney disease, sickle-cell and disease, Tay-Sachs disease; and/or the chromosomal abnormality is selected from the group consisting of: a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis. In other embodiments, the genetic mutation or chromosomal abnormality may be one or more selected from those having a clinical utility gene cards (CUGCs) of the EuroGentest2 initiative (www.eurogentest.org). In particular embodiments, the chromosomal abnormality is a trisomy (such as trisomy 21, trisomy 18, or trisomy 13), a sex-chromosome abnormality or a chromosomal deletion.

Such diagnosis or test may be directed at a species DNA to identify a genetic mutation or chromosomal abnormality of such DNA that is derived from a cell or cell-type associated with a medical condition. Accordingly in one of such embodiments, said species of DNA originates from cells of a tumour and said abnormality is a genetic mutation or a chromosomal abnormality associated with the diagnosis, prognosis or predictive treatment of a carcinoma or cancer. In particular such embodiments, the genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERk, or TRK) and a DNA repair gene (such as HMGA1, HMGA2, MGMT or PMS2); and/or the chromosomal abnormality is a translocation (such as t(9;22)(q34;q11) [ie, Philadelphia chromosome or BCL-ABL], t(8;14)(q24;q32), t(11;14)(q13;q32), t(14;18)(q32; q21), t(10;(various))(q11;(various)), t(2;3)(q13;p25), t(8;21) (q22;q22), t(15;17)(q22;q21), t(12;15)(p13;q25), t(9;12) (p24;p13), t(12;21)(p12;q22), t(11;18)(q21;q21), t(2;5)(p23; q35), t(11;22)(q24;q11;q11.2-12), t(17;22), t(1;12)(q21; p13), t(X;18)(p11.2;q11.2), t(1;19)(q10;p10), t(7,16)(q32-34;p11), t(11,16)(p11;p11), t(8,22)(q24;q11) or t(2;8)(p11; q24)).

A related aspect of the present invention relates to an alternative method for detecting in a sample from an individual an amount of a species of DNA originating from cells of a given type, which sample comprises said species of DNA in admixture with differentially methylated DNA not originating from cells of said type; said method comprising the steps:
(a) treating the DNA present in said sample with a reagent that differentially modifies methylated and non-methylated DNA; and
(b) detecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample,
wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs. Such an alternative method of the present invention is not intended to be practiced on the human or animal body; for example it is intended to be practiced in an in-vitro manner. Further characterisation of any of the features of this alternative method of the present invention (or any combination of such features) can include the characterisationss (and their combinations) as described elsewhere herein in respect of the first aspect of the invention, in particular embodiments of this alternative method of the present invention, the reagent comprises one or more methylation sensitive restriction enzyme, such as one (or a combination thereof) as disclosed herein.

In a second aspect, the invention relates to a method for detecting an increased risk of an individual suffering from or developing a medical condition, said method comprising the steps:
(i) conducting a method of the present invention that determines a quantitative amount said species of DNA (and/or total DNA) in the sample; and
(ii) comparing the amount of said species of DNA detected with a threshold amount and/or a reference distribution of amounts,
wherein an increase in the (or outlying of) amount of said species of DNA (and/or total DNA) indicates an increased risk of the individual suffering from or developing said medical condition.

A third aspect of the invention relates to a composition (eg, one that is useful for, or used in, a method of the present invention), said inventive composition comprising:
two pairs of PCR primers, each pair for amplifying one of said two of more DMRs as set forth anywhere herein;
one pair of PCR primers for amplifying said other region as set forth anywhere herein;
two labelled probes for quantitative probe-based PCR, each of which specific for one of said DMRs, and labelled with the same detectable labels(s) for each of said probe; and
one labelled probe for quantitative probe-based PCR specific for said other region and labelled with different detectable label(s) to the probes used for said DMRs.

Such a composition of the present invention may further comprising:
a further pair of PCR primers for amplifying a second other region as set forth anywhere herein; and
a further labelled probe for quantitative probe-based PCR specific for said other region and labelled with detectable label(s) that is different to those used probes for said DMRs; and optionally that is the same as that used for the probe(s) specific the first other region.

A fourth aspect of the invention relates to a kit (for example a kit of separate components; such as a kit of holders or vessels, each holding a different component of the kit), such kit comprising a set of primers and probes as comprised in a composition of the present invention. A kit of the present invention may comprise additional components. For example, the kit may additionally comprise: (i) a printed manual or computer readable memory comprising instructions to use said primers and probes, including to use them to practice a method of the present invention and/or to produce or use a composition of the present invention; and/or (ii) one or more other item, component or reagent useful for the practice of a method of the present invention; and/or the production or use of the composition of the present invention, including any such item, component or reagent disclosed herein, such as a reagent that differently modifies methylated and non-methylated DNA as set forth anywhere herein.

A further aspect of the invention relates to a computer program product comprising a computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a given type may be performed, in each case from a sample from an individual comprising a species of DNA originating from cells of a given type in admixture with differently methylated DNA not originating from cells of said type, the DNA in present in said sample being treated with a reagent that differentially modifies methylated and non-methylated DNA as set forth herein; said operation comprising the steps of:

receiving: (i) one signal representing the essentially simultaneous quantitative detection of methylation at two or more DMRs as set forth in step (b) as described anywhere herein; and (ii) one signal representing the essentially simultaneous quantitative detection of total DNA using at least one other region as set forth in step (c) as described anywhere herein;

determining a parameter from the signals (i) and (ii), wherein the parameter represents a quantitative amount of said species of DNA (and/or said total DNA);

comparing the parameter to with a threshold amount and/or reference distribution of amounts; and based on such comparison, determining a classification of whether, respectively, (x) an increased risk of an individual suffering from or developing a medical condition exists; and/or (y) a diagnosis for an anomaly in a species of DNA originating from cells of a given type may be performed.

In certain embodiments, a computer program product of the present invention the operation further comprises steps of: receiving a further signal representing the quantitative detection of total DNA in a standard sample of DNA as set forth anywhere else herein; and comparing said signal with the signal representing the essentially simultaneous quantitative detection of total DNA using at least one other region, so as to determine said parameter that represents an absolute quantitative amount of said species of DNA.

In particular embodiments, the computer program product of the present invention is for an operation for determining if a diagnosis for an anomaly in said species of DNA may be performed, and said operation further comprises the step of determining from said parameter a number of random and/or enriched DNA molecules to be sequenced from, preferably from a separate aliquot of DNA of, said sample as part of said diagnosis.

One embodiment of operations performed and/or controlled by the computer program product of the invention is depicted in FIG. 5. Operation (A) receives signals (1) and (2) that represent, respectively, the methylation at the DMRs and the total DNA, and optionally signal (3) then represents an amount of total DNA from a standard sample. Operation (A) determines a parameter (4) from signals (1), (2) and optional (3) that represents a relative or absolute amount, of DNA (eg from foetal vs total DNA). This parameter (4) is compared by operation (B) against a threshold amount (5) and/or a reference population of amounts (5) so as to classify (7) the risk of an individual suffering from a medial condition and/or if a diagnosis for an anomaly in either of the QUA in the sample may be performed.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited: herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

EXAMPLE 1: USE OF THE METHOD OF THE INVENTION IN NIPT IN MULTIPLE PREGNANCIES, INCLUDING IN CASES OF VANISHING TWINS

Sample Collection, Processing and DNA Extraction:

36 blood samples from women pregnant with multiple gestations (mono-, di- and trichorionic twin and triplet pregnancies) were collected between Nov. 6, 2012 and Nov. 16, 2013, for research & development (R&D) purposes and as part of routine non-invasive prenatal testing (NIPT) laboratory procedure. One blood sample came from a woman pregnant with triplets, the remaining 35 samples came from twin pregnancies. From each pregnant woman carrying a multiple pregnancy two samples each with 7-10 ml venous blood were collected using Streck cell-free DNA blood collection tubes (Streck). The blood samples were shipped to the diagnostic laboratory with a maximum delivery time of 4 days. Other blood samples from pregnant females analysed herein were similarly collected.

Plasma preparation was performed by centrifugation (1600 g for 10 min at 4° C.) and plasma separation followed by a second centrifugation step (16000 g for 10 min at 4° C.). Extraction of total cell-free DNA (cfDNA) was performed with QIAamp Circulating Nucleic Acid Kit (Qiagen) according to the manufacturer protocol using 3.0-4.0 ml plasma with a final elution volume of 60 ul AVE-buffer (Qiagen).

DNA Quantification:

Foetal cell-free DNA (foetal cfDNA) was detected and quantified in relation to total cell-free DNA (total cfDNA) in order to determine die foetal cfDNA fraction as both a relative concentration and absolute amount using a method of the present invention. From the eluted cell-free DNA, 11 ul were digested with the CpG-methylation sensitive enzymes HhaI (0.4 U/ul), HpaII (0.3 U/ul) and BstUI (0.3 U/ul) in a 22 ul reaction using CutSmart™ Buffer (New England Biolabs). The reaction was incubated for 60 min at 37° C. and 60 min at 60° C. 10 ul from the digestion reaction was used as template DNA for quantitative probe-based PCR (reactions were conducted in duplicate), described briefly as follows.

A 25 ul PCR reaction using a 2-fold concentrated PCR master mix (QuantiFast Multiplex PCR Kit, Qiagen) was conducted. Primers that span CpG methylation sensitive restriction enzyme sites of the respective region that is differentially methylated between foetal and maternal DNA (as a DMR) were used in combination with FAM-labelled probes for such DMRs, and primers that do not span any restriction enzyme sites, an other region that is not differentially methylated between foetal and maternal DNA (as an OR) are used in combination with VIC-labelled probes for such ORs. The sequences of the primers and labelled probes used in this example are described in TABLE 1, and the thermocycler profiles used for the quantitative probe-based (TaqMan) PCR (LightCycler 480 II Instrument; Roche) are described in TABLE 2. In this example, the probes used to detect the presence of the two DMRs, are each labelled with the same detectable fluorescein amidite (FAM) fluorescent moiety, and each with the same minor binding grove (MGB) non-fluorescent quencher (NFQ) moiety, and the probes used to detect the presence of the two ORs, are each labelled with the same detectable VIC (life Technologies) fluorescent moiety, and each with the same MGBNFQ moiety.

maternal DNA and hypermethylated in foetal DNA (Nygren, et al, 2010; Clin Chem 56, 1627; Chan et al, 2006; Clin Chem 42, 2211; Chiu et al, 2007: Am J Pathol 170, 941), and two other regions (ORs) not differentially methylated between maternal and foetal DNA which are each located between about 20 bp and 20 kb of their DMR. In particular, the methylation insensitive locus located in RASSF1A is located between 8 kb and 9 kb (8.97 kb) downstream of the methylation sensitive locus located in RASSF1A, and the methylation insensitive locus located in TBX3 is located between 10 kb and 11 kp (10.64 kb) downstream of the methylation sensitive locus located in TBX3. FIG. 2 depicts the respective arrangements and detection modalities of the two DMRs and the two other regions used in this example.

Parallel probe-based quantitative PCR reactions were performed (in separate reactions within the same PCR run) using for template a serial dilution of male genomic DNA (Promega) having known concentrations as a standard. The foetal cfDNA fraction was calculated by relative quantification of signals in the FAM channel (DMR; ie detecting foetal cfDNA) versus the VIC channel (ORs; ie detecting total cfDNA), and the absolute total cfDNA amount was calculated by absolute quantification of signals in the VIC channel obtained from the sample compared to the VIC channel obtained from the dilution series of standard DNA

TABLE 1

Quantitative (probe based) PCR components

| Region | Component | Sequence (5'-3')* | SEQ ID No. | Stock Conc | ul for 1x | Final uM Conc |
|---|---|---|---|---|---|---|
|  | Master-mix | N/A |  | 2x | 12.5 | 1x |
| RASSF1A DMR | DMR1-For | ATT GAG CTG CGG GAG CTG GC | 1 | 100 uM | 0.35 | 1.4 |
|  | DMR1-Rev | TGC CGT GTG GGG TTG CAC | 2 | 100 uM | 0.35 | 1.4 |
|  | DMR1-Probe | [FAM]-ACC CGG CTG GAG CGT-[MGBNFQ] | 3 | 100 uM | 0.035 | 0.14 |
| RASSF1A Other region | OR1-For | GGT CAT CCA CCA CCA AGA AC | 4 | 100 uM | 0.35 | 1.4 |
|  | OR1-Rev | TGC CCA AGG ATG CTG TCA AG | 5 | 100 uM | 0.35 | 1.4 |
|  | OR1-Probe | [VIC]-GGG CCT CAA TGA CTT CAC GT-[MGBNFQ] | 6 | 100 uM | 0.035 | 0.14 |
| TBX3 DMR | DMR2-For | GGT GCG AAC TCC TCT TTG TC | 7 | 100 uM | 0.35 | 1.4 |
|  | DMR2-Rev | TTA ATC ACC AGC CGC ATG GC | 8 | 100 uM | 0.35 | 1.4 |
|  | DMR2-Probe | [FAM]-CCC TCC CGG TGG GTG ATA AA-[MGBNFQ] | 9 | 100 uM | 0.035 | 0.14 |
| TBX3 Other region | OR2-For | TGT TCA CTG GAG GAC TCA TC | 10 | 100 uM | 0.35 | 1.4 |
|  | OR2-Rev | CAG TCC ATG AGG GTG TTT G | 11 | 100 uM | 0.35 | 1.4 |
|  | OR2-Probe | [VIC]-GAG GTC CCA TTC TCC TTT-[MGBNFQ] | 12 | 100 uM | 0.035 | 0.14 |
| General reagents | DMSO | N/A |  | 100% | 0.025 | 0.625 |
|  | MgCl2 | N/A |  | 50 mM | 2 | 1 |
|  | DNA sample | N/A |  |  | 10 |  |
|  | Water |  |  |  | — |  |
|  | Total |  |  |  | 25 |  |

*The dyes used for each probe are shown in "[ ]" parentheses

TABLE 2

Thermocycler profiles

| Step | Temperature | Time | Cycles | Analysis mode |
|---|---|---|---|---|
| Pre-incubation | 95° C. | 5 min | 1 | None |
| Denaturation | 95° C. | 10 sec | 45 | Quantification |
| Annealing | 60° C. | 10 sec |  | None |
| Elongation | 72° C. | 8 sec |  | Single |
| Cooling | 40° C. |  |  | None |

The assay design used in this example is based on two marker DMRs which are described to be hypomethylated in of known concentration. Such relative and absolute quantifications were conducted using LightCycler 480 Software release 1.5.0 (Roche).

Maternal Plasma DNA Sequencing and Data Analysis to Identify Foetal Aneuploidy.

DNA sequencing libraries were prepared using NE8Next Ultra™ DNA Library Prep Kit from Illumina. Libraries were prepared according to the manufacturer protocol automated on a Hamilton STARplus robot. Library quality and quantity was measured using a Bioanalyzer instrument (Agilent) and a Qbit Fluorometer (Invitrogen). Based on the library quantification dilutions and equimolar pools of 12 samples per pool were prepared. The pooled samples were sequenced on one lane of an Illumina v3 flow cell on an Illumina HiSeq2000 sequencer. Clonal clusters were generated using TruSeq SR Ouster Kit v3-cBot-HS on a cBot Cluster generation System according to the manufacturer protocol. Bioinformatic analysis to identify foetal chromosomal aneuploidy was carried out as described previously, with z-scores ≥3 indicating the presence of a foetal trisomy 21 (Stumm et al 2014, Europ Prenat Diag 34:185). In cases of a positive test result for foetal aneuploidy from this method, the result was confirmed by invasive diagnostic methods.

Results.

Characteristics, % foetal fraction of cfDNA and aneuploidy test results for the blood samples are given in TABLE 3. There were two positive test results indicating foetal trisomy 21. Both were confirmed by karyotyping after amniocentesis; thus, the false positive rate in this study was 0%. One blood sample represented monochorionic twins with concordant karyotypes [47,XY,+21] and the other one represented dichorionic twins with discordant karyotypes [47,XY,+21 and 46,XX]. In both samples the foetal fraction was as high as 18.0 and 24.8%, respectively. All other NIPT results were negative for trisomies 21, 18 and 13. There is no evidence for false-negative NIPT results so far in the pregnancies included in this study. Nevertheless, a number of pregnancies are still on-going (with the last birth of the patients expected in mid May 2014) and therefore, the final defection rate is still uncertain.

The reliable detection of foetal aneuploidy in twin pregnancies by NIPT is dependent on a sufficiently high amount of foetal cfDNA from each foetus in the maternal blood. Different data and considerations have been published on how the lower limit of foetal cfDNA fraction should be defined to ensure that each twin's contribution is above the detection threshold (Leung et al 2013, Prenat Diag 33:675; Qu et al 2007, Am J Pathol 170:941; Struble et al 2013, Fetal Diagn Ther December 7 Epub ahead of print). This is especially important for dichorionic twin pregnancies with discordant karyotypes. In the study described above, supporting information was used for the definition of the minimum foetal cfDNA fraction for twin pregnancies derived from the Y-chromosomal representation, if only one of the two foetuses is male. Using the method of the present invention, the total foetal cfDNA fraction can be determined, which reflects the summary of foetal cfDNA derived from both foetuses. Using the Y-chromosomal representation from the next generation sequencing, the foetal cfDNA amount can be determined for male foetuses (as described in Stumm et al 2014). Thus, in the case of mixed foetal gender the contributing amount of each foetus can be determined by subtraction of the amount of foetal cfDNA determined by the Y-chromosomal representation from the foetal cfDNA fraction measured by method of the present invention. The foetal cfDNA fractions determined by the method of the present invention were compared with the values obtained from Y-chromosomal reads from next generation sequencing

TABLE 3

Characteristics and NIPT results for the collected blood samples

| Sample | Chr13 z-score | Chr18 z-score | Chr21 z-score | Foetal DNA fraction (%) | Gestational age (p.m.) | No. of foetuses, chorinicity amnionicity | NIPT result |
|---|---|---|---|---|---|---|---|
| LCMPC05 | 1.3 | −1.0 | −0.8 | 16.7 | 11 + 5 | 3, trichorionic, triamniotic | negative |
| LCMPC06 | −0.4 | 1.1 | 8.5 | 18.0 | 13 + 2 | 2, monochorionic, n.a. | T21 positive |
| LCMPC07 | −1.0 | 0.3 | 0.9 | 7.9 | 19 + 0 | 2, dichorionic, diamniotic | negative |
| LCMPC08 | 0.7 | 1.2 | 0.0 | 16.5 | 18 + 1 | 2, dichorionic, diamniotic | negative |
| LCMPC09 | 0.6 | −0.8 | 0.7 | 8.9 | 11 + 5 | 2, monochorionic, diamniotic | negative |
| LCMPC10 | 0.3 | 0.7 | −0.7 | 17.6 | 20 + 4 | 2, dichorionic, diamniotic | negative |
| LCMPC11 | −0.9 | −0.8 | 0.7 | 11.5 | 23 + 0 | 2, dichorionic, diamniotic | negative |
| LCMPC12 | −0.9 | −0.7 | −2.0 | 13.3 | 11 + 1 | 2, monochorionic, diamniotic | negative |
| LCMPC13 | 1.3 | 0.1 | 0.3 | 21.4 | 16 + 0 | 2, dichorionic, diamniotic | negative |
| LCMPC14 | 0.2 | −0.3 | 0.0 | 6.8 | 12 + 5 | 2, n.a., n.a. | negative |
| LCMPC15 | 2.2 | 0.1 | 14.7 | 24.8 | 16 + 0 | 2, dichorionic, diamniotic | T21 positive |
| LCMPC16 | 1.1 | 1.7 | 0.5 | 5.4 | 12 + 5 | 2, n.a., n.a. | negative |
| LCMPC17 | 0.7 | 1.4 | 0.5 | 16.5 | 14 + 2 | 2, n.a., n.a. | negative |
| LCMPC18 | 0.3 | 2.6 | 0.0 | 18.5 | 18 + 3 | 2, n.a., n.a. | negative |
| LCMPC19 | −0.2 | 0.8 | 0.3 | 16.6 | 14 + 0 | 2, dichorionic, diamniotic | negative |
| LCMPC20 | −0.7 | −0.9 | 0.1 | 13.1 | 15 + 4 | 2, dichorionic, diamniotic | negative |
| LCMPC21 | 1.0 | −0.7 | 1.2 | 8.4 | 9 + 3 | 2, dichorionic, diamniotic | negative |
| LCMPC22 | −1.1 | −0.2 | 0.3 | 5.6 | 16 + 2 | 2, monochorionic, n.a. | negative |
| LCMPC23 | −2.2 | 2.2 | −0.8 | 20.6 | 19 + 5 | 2, monochorionic, n.a. | negative |
| LCMPC24 | −1.6 | −0.4 | −0.5 | 14.7 | 22 + 2 | 2, monochorionic, diamniotic | negative |
| LCMPC25 | −0.8 | −0.2 | −1.5 | 12.1 | 11 + 5 | 2, n.a., n.a. | negative |
| LCMPC26 | −0.4 | −0.6 | −1.3 | 7.5 | 13 + 0 | 2, dichorionic, diamniotic | negative |
| LCMPC27 | 0.5 | −0.8 | −0.4 | 16.3 | 12 + 6 | 2, n.a., n.a. | negative |
| LCMPC28 | −1.2 | −0.3 | −0.7 | 19.4 | 10 + 1 | 2, dichorionic, diamniotic | negative |
| LCMPC29 | −0.8 | 0.7 | −0.4 | 14.2 | 13 + 2 | 2, monochorionic, n.a. | negative |
| LCMPC30 | 0.7 | 0.3 | 0.9 | 14.9 | 12 + 2 | 2, monochorionic, monoamniotic | negative |
| LCMPC31 | −0.2 | 0.3 | −0.9 | 19.3 | 19 + 1 | 2, dichorionic, diamniotic | negative |
| LCMPC32 | −1.1 | 2.5 | −2.2 | 11.6 | 20 + 0 | 2, dichorionic, diamniotic | negative |
| LCMPC33 | 0.2 | 2.2 | −1.6 | 8.6 | 11 + 0 | 2, dichorionic, diamniotic | negative |
| LCMPC34 | −1.0 | 1.2 | 0.0 | 15.1 | 15 + 4 | 2, dichorionic, diamniotic | negative |
| LCMPC35 | −0.3 | −0.8 | −0.3 | 19.2 | 12 + 0 | 2, dichorionic, diamniotic | negative |
| LCMPC36 | −1.4 | −0.5 | −0.8 | 13.9 | 12 + 0 | 2, dichorionic, diamniotic | negative |
| LCMPC37 | 1.8 | −0.7 | 0.1 | 13.8 | 17 + 6 | 2, dichorionic, diamniotic | negative |
| LCMPC38 | −0.1 | 1.1 | −0.7 | 13.4 | 13 + 1 | 2, dichorionic, diamniotic | negative |
| LCMPC39 | −1.9 | 0.2 | −2.2 | 15.0 | 17 + 0 | 2, dichorionic, diamniotic | negative |
| LCMPC40 | 0.6 | −0.4 | 0.8 | 16.2 | 18 + 3 | 2, dichorionic, diamniotic | negative | for cases with known gender (see FIG. 3). There is a correlation of the amount of male specific cfDNA (y axis) to the foetal cfDNA fraction measured by method of the present invention (x axis). Thus, for twin pregnancies with male/male gender approximately true is: [y=x], for female/male genders it is: [y=0.5x] and for female/female: [y=1]. The genders of cases with similar values are male/male and in case of differing values with low Y-chromosomal representation the genders are female/female. The intermediate cases, which show about half the percentage of foetal fraction as Y-chromosomal representation, are of mixed gender. The data presented in FIG. 3 show that it is not only possible to determine the foetal genders using NIPT results for twin pregnancies, but also that the measurement of the amount of foetal fraction of cfDNA determined by the method of the present invention is surprisingly accurate as compared to frequency counting of Y chromosome sequences. On the other hand, these data support the hypothesis that each foetus of a twin pregnancy contributes roughly about half of the total foetal cfDNA fraction. This leads to the conclusion that for twin pregnancies, twice the amount of foetal cfDNA would be required, and thus a recommended minimum foetal fraction of cfDNA for NIPT of a twin pregnancy could be considered to be 8%.

For monochorionic twin pregnancies with concordant genotypes (apart from rare exceptions, Chen et al 2013, Am J Med Genet A 161A:1817), a foetal cfDNA fraction of 4% would be enough to detect a foetal aneuploidy, just as for single pregnancies. However, for routine laboratory NIPT service one major issue speaks against the implication of such different quality criteria for mono- and dichorionic pregnancies: the determination of chorionicity is dependent on the gestational age and the practical experience of the physician performing the ultrasound examination. The chorionicity is clearly detectable in the first trimester of a multiple pregnancy, but in later stages detection becomes more difficult (Sperling et al 2001, Acta Obstet Gynecol Scand 80:287). Therefore, it is a safer strategy to generally define a minimum foetal cfDNA fraction for twin pregnancies, which is applicable for monochorionic as well as for dichorionic multiple pregnancies.

Identification of Vanishing Twins.

In two cases of NIPT aneuploidy testing in which the foetal cfDNA fraction was measured using the method of the present invention, identified a trisomy 21 (z-scores 13.5 and 3.4 respectively), but also a striking discrepancy between the total foetal cfDNA fraction measured by the method of the invention and the cf-Foetal-DNA amount measured by Y-chromosome representation were observed.

For case A, two analyses of blood samples (first and back-up samples) estimated the total foetal cfDNA fraction measured the method of the present invention was 20.7% and 24.8%, respectively, whereas the foetal cfDNA according to the Y-chromosomal representation from next generation sequencing was 9.2% and 9.3%, respectively. It was speculated, and reported to the physician, that the pregnancy may be a mixed-sex twin pregnancy, who confirmed that a deceased twin had been observed during ultrasound scan at week 10. A further blood sample taken in the third trimester of the pregnancy (38+2) turned out to be negative for trisomy 21 and the foetal cfDNA amount measured by Y-chromosomal representation correlated with the foetal amount measured by QuantYfeX (21.7% and 21.4), which matched the male gender determined by karyotyping of the living foetus. At birth a foetus papyraceus was found in the placental tissue from which a sufficient amount of cells could be isolated for cell culture and following GTG banding, a trisomy 21 positive, female karyotype was confirmed (47,XX,+21).

For case B, a slightly increased Y-chromosomal representation was monitored indicating male specific cf-Foetal-DNA of 3.0% and 2.7% respectively. As the foetal cfDNA fraction estimates measured by the method of the invention were far above that (13.4% and 10.0%) we hypothesized from this discrepancy in the foetal fraction measured, that two foetuses with discordant gender contribute to the foetal fraction and the male foetus being the one affected by trisomy 21. This suggestion was derived from the correlation of Y-chromosome specific foetal cfDNA amount of roughly 3% with the elevated z-score around the cut-off value of 3.0. Since the examination was clearly requested for a singleton pregnancy, the male specific foetal cfDNA was suspected to stem from a vanishing twin—maybe the carrier of a trisomy 21—that was either not recognized or not indicated on the consent form for NIPT. Thus, the result was reported to be indecisive for chromosome 21 and the conflicting data was reported to the responsible physician, including a notice regarding the potential vanishing twin, for further clarification via ultrasound. The responsible physician subsequently confirmed that the pregnancy had started as twin and later continued as a singleton pregnancy. The gender of the living and apparently healthy foetus was confirmed to be female and thus, the foetal cfDNA that caused the increased z-score for trisomy 21 can clearly be assigned to a deceased male foetus. The pregnancy is still on-going and further analysis of placental tissue and blood of the living foetus is not yet possible.

EXAMPLE 2: IMPROVED DETECTION SENSITIVITY USING TWO DIFFERENTIALLY METHYLATED REGIONS USING THE SAME DETECTABLE MOIETY/MOIETIES FOR EACH DIFFERENTIALLY METHYLATED REGION

The inventors were surprised to observe that a complex and multiplex reaction detecting two DMRs using the same detectable moiety/moieties for each of said DMR (as well as two other regions (OR) not differentially methylated) was more sensitive to detect foetal cfDNA fraction than previous detection reactions that each detected—in separate PCR reactions—a single DMR (as well as a single OR) (FIG. 4).

In a method of the present invention, two DMRs (those found in RASSF1A and TBX3, as described in Example 1) were detected (over 4 dilutions) with the same aliquot of DNA and reaction—effectively simultaneously (using quantitative probe-based (TaqMan) PCR) with two ORs (those found in RASSF1A and TBX3, as described in Example 1), using: (x) the same detectable moiety/moieties for each of said DMR; and (y) a detectable moiety/moieties for said at least one OR that is/are different to the detectable moiety/moieties used for said DMRs. In comparison, detection of foetal cfDNA fraction was less sensitive, as shown by detection at higher cycle numbers (Cp), if each DMR (and corresponding OR) was detected independently in separate reactions. The regions/markers, primers/probes and detection methodology was substantially as described in Example 1, except that for the single locus reactions, only the DMR and OR from a given gene (RASSF1A or TBX3) were detected simultaneously in a single reaction.

In contrast, defection of foetal of DNA fraction using a multiplex reaction of the two DMRs using different detectable moieties (eg RAM for the RASSF1A locus and VIC for the TBX3 locus) is determined to be even less sensitive, and further is difficult to detect simultaneously with any OR; without being bound by theory, believed due to the higher complexity of colour compensation, the limited number of separately detectable fluorescent markers and/or the "bleaching" effects from so many fluorescent markers being present in the same reaction.

Given the exponential nature of quantitative PCR detection, a higher sensitivity of detection (ie lower cycle numbers) would also equate to higher accuracy of quantification, as the correction to standard curves, and interpolation between data points, would be subject to less error than that, arising with the amounts of DNA correlating to detection at higher cycle numbers.

EXAMPLE 3: DETECTION OF AN INCREASED RISK OF A PREGNANT WOMAN SUFFERING FROM OR DEVELOPING PREECLAMPSIA (PROPHETIC EXAMPLE)

Using a method of the present example, pregnant women are assessed for their risk of suffering from or developing preeclampsia as follows. Firstly, a blood sample is collected from the woman for whom such risk to be assessed and total cfDNA extracted from the plasma of such sample substantially in accordance with the procedures described in Example 1. Secondly, using s method substantially as described in Example 1, a relative and/or absolute amount of foetal cfDNA and total cfDNA present in the plasma is determined, where the absolute amount of foetal and/or total cfDNA can be expressed as the amount of genome equivalents ("Eq"). Thirdly, such determined amount of cfDNA and/or total cfDNA is compared to a threshold amount or a reference distribution of amounts, and the woman is determined to be at increased risk of suffering from or developing preeclampsia if the amount of foetal cfDNA or total cfDNA exceeds such threshold value and/or is an outlier in such distribution.

For example, using published threshold values (Papantoniou et al 2013, Prenat Diag 33:682) if the total cfDNA exceeds an amount of about 7,500 Eg/mL plasma or if the foetal cfDNA fraction exceeds an amount of about 500 Eg/mL plasma, then the woman is determined to have such an increased risk. Such a risk may instead or additional be assessed by considering: (i) the fold-increase (eg 1.5, 3, 3.5 or 4-fold increase) of foetal cfDNA (determined for such woman compared to a threshold amount), factoring into the determination that for later-term pregnancies a higher fold-increase in foetal cfDNA may be utilised (Zeybek et al 2013, J Obstet Gynaecol Res 39:632); and/or (ii) into which percentile the amount of cfDNA determined from the woman falls, from consideration of a reference distribution of amounts determined from low-risk women or women who did not suffer from or develop preeclampsia, for example if the foetal cfDNA fraction fails within the 90$^{th}$ percentile of such a distribution, then the woman is considered to have an increased risk of suffering mild or severe preeclampsia (Jakobsen et al 2013, Transfusion 53:1956).

In this example, t detection of a risk is conducted using a computer program product that performs the operations represented by FIG. 5. Operation (A) receives signals (1) and (2) representing, respectively, foetal and total cfDNA are used by the computer program product to determine a parameter (4) that represents the relative and/or absolute amount of foetal (or total) cfDNA present in the plasma of the woman. This operation may optional receive a signal (3) representing an absolute amount of standard DNA. A second operation (3) compares such determined parameter (4) against a threshold amount (5) and/or a reference population of amounts (6) so as to determine and report (7) whether or not—and based on such comparison—the woman is determined to be at increase risk of suffering or developing preeclampsia.

EXAMPLE 4: DETECTION OF TUMOUR-ASSOCIATED DNA IN SAMPLES FROM CANCER PATIENTS (PROPHETIC EXAMPLE)

Methylation of RASSF1A and at least one other DMR such as ER-beta (oestrogen receptor beta), RAR-beta2 (retinoic acid receptor beta 2) and/or Cyclin D2 is used to detect cfDNA derived from a tumour and to assess the risk of women suffering from breast cancer. Specific methylation at such DMRs is a characteristic of tumour-derived cfDNA, and a method of the present invention is used to detect and to quantify the amount tumour derived cfDNA in the plasma of women, and those determined to have elevated (or outlying) amounts of tumour-derived cfDNA are determined to be at increased risk from suffering from or developing breast cancer. Essentially, the process described in Example 3 is followed except that DMR2 and OR2 are located in one of ER-beta, RAR-beta2 or Cyclin D2, rather than TBX3. Primers and probes to detect such DMR2 and OR2 for use in this embodiment of the present invention are designable by the person of ordinary skill.

In this example, a similar computer program product as described in Example 3 can be used to assess the risk for a given woman is based on the amount of tumour-derived cfDNA present in her blood, but in this example this parameter is compared against a threshold amount or distribution of amounts that is derived from a study of the amount of tumour-derived cfDNA present in control and breast-cancer patients; and those women having an elevated (or outlying) amount of tumour-derived cfDNA are considered to have an increased risk of suffering from or developing breast cancer.

In view of the above, it will be appreciated that the present invention also relates to the following items:

1. A method for detecting in a sample from an individual an amount of a species of DNA originating from cells of a given type, which sample comprises said species of DNA in admixture with differently methylated DNA not originating from cells of said type; said method comprising the steps;
    (a) treating the DNA present in said sample with a reagent that differentially modifies methylated and non-methylated DNA;
    (b) detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample; and
    (c) detecting an amount of total DNA present in said sample using at least one other region that is not differently methylated between said species of DNA and the DNA not originating from cells of said type, the modification of which region(s) by said reagent is insensitive to methylation of DNA, wherein, said detection in step (b) and said detection in step (c) are made using the same aliquot of DNA of said sample, and in the same vessel, and effectively simultaneously for such DMRs and other region(s), and using: (x) the same detectable labels(s) for each of said DMRs; and (y) a different detectable label(s) for said other region(s).

2. The method of item 1, wherein prior to or as part of said detection in step (b) and/or step (c), each DNA region comprising said DMRs and/or said other region(s), respectively, is(are) amplified.

3. The method of item 1 or 2, wherein each detectable label used in step (b) and/or step (c) is independently selected from the group consisting of: fluorescent, protein, small molecule or radioactive label.

4. The method of any one of items 1 to 3, wherein said detection in step (b) comprises multiplex real-time probe-based quantitative probe-based PCR using at least two labelled probes each of which specific for one of said DMRs.

5. The method of any one of items 1 to 4, wherein said detection in step (c) composes real-time quantitative PCR using at least one labelled probe specific for one of said other region(s).

6. The method of any one of items 1 to 5, wherein said other region is located between about 20 bp and about 20 kb upstream or downstream of, and/or within the same gene as, at least one of said DMRs.

7. The method of any one of items 1 to 6, wherein said detection in step (c) comprises using at least two of said other regions; preferably wherein, the number of said other regions is the same as the number of DMRs used in step (b); more preferably wherein, one of said other regions is located between about 20 bp and about 20 kb upstream or downstream of a DMR used in step (b) and each other of the said other regions is located between about 20 bp and about 20 kb upstream or downstream of another of said DMRs.

8. The method of item 7, wherein said detection in step (c) is made using the same detectable label(s) for each of said other regions.

9. The method of item 7 or 8, wherein said detection in step (c) comprises multiplex real-time quantitative probe-based PCR using at least two labelled probes each of which is specific for one of said other regions.

10. The method of any one of items 1 to 9, wherein said detection in step (c) and said detection in step (b) are made using the same aliquot of DNA of said sample, and in the same reaction/detection vessel, and effectively simultaneously with each other, and by multiplex real-time quantitative probe-based PCR using at least one labelled probe specific for each of the said DMRs and other region(s).

11. The method any one of items 1 to 10, wherein said species of DNA originates from cells of a foetus and/or the placenta of a foetus and said sample is from a pregnant female; preferably wherein, said species of DNA is circulating cell-free DNA and said sample is a blood fraction such as plasma or serum.

12. The method of item 11, wherein said DMRs comprises at least one, preferably at least two, methylation site(s) specific for said reagent, and at least one of said DMRs is located in a portion of the genome and/or gene selected from the group consisting of: RASSF1A, TBX3, HLCS, ZFY, CDC42EP1, MGC15523, SOX14 and SPN; preferably wherein, each of said DMRs is located in a portion of the genome and/or gene selected from the group consisting of: RASSF1A, TBX3, HLCS, ZFY, CDC42EP1, MGC15523, SOX14 and SPN; and/or at least one of said DMRs is located between about positions 4,700 bp and 5,600 bp of RASSF1A ox about positions 1,660 bp and 2,400 bp of TBX3; more preferably wherein, said two or more DMRs comprise those located between about positions 4,700 bp and 5,600 bp of RASSF1A and about positions 1,660 bp and 2,400 bp of TBX3.

13. The method of item 11 or 12, wherein said other region is located in a portion of the genome and/or gene selected from the group consisting of: GAPDH, beta-actin, ALB, APOE, RNASEP. RASSF1A, TBX3, HLCS, ZFY, CDC42EP1, MGC15523, SOX14 and SPN; preferably wherein, said other region comprises a region without a methylation site specific for said reagent and said locus is located in the genes RASSF1A or TBX3, more preferably wherein;

two or more of said other regions are used in detection step (c) and comprise those located between about positions 14,220 bp and 13,350 bp of RASSF1A and about positions 12,400 bp and 13,000 bp of TBX3.

14. The method any one of items 11 to 13, wherein said pregnant female is susceptible to a pregnancy-associated medical condition; preferably wherein, said pregnancy-associated medical condition is selected from the group consisting of: preeclampsia, preterm labour, intrauterine growth retardation and vanishing twin.

15. The method of any one of items 1 to 10, wherein said species of DNA originates from a cell type associated with a medical condition; preferably wherein, said medical condition is one selected from the group consisting of: a cell proliferative disorder, an infection/infectious disease, a wasting disorder, a degenerative disorder, an (auto)immune disorder, kidney disease, liver disease, inflammatory disease acute toxicity, chronic toxicity, myocardial infarction, and a combination of any of the forgoing; more preferably wherein, said species of DNA is circulating cell-free DNA and said sample is a blood fraction such as plasma or serum.

16. The method of item 15, wherein said species of DNA originates from cells of a tumour; preferably wherein, said tumour is a carcinoma or cancer of an organ selected from the group consisting of: liver, lung, breast, colon, oesophagus, prostate, ovary, cervix, uterus, testis, brain, bone marrow and blood.

17. The method of item 16, wherein said DMRs comprises at least one, preferably at least two, methylation site(s) specific for said reagent, and at least one of said DMR is located in a portion of the genome and/or a gene selected from the group consisting of: a tumour suppressor gene, p16, SEPT9, RASSF1A, GSTP1. DAPK, ESR1, ARC, HSD17B4 and H1C1; preferably wherein, one of said two or more DMRs is located in RASSF1A; more preferably wherein, one of said two or more DMRs is located between about positions 4,700 bp and 5,600 bp of RASSF1A; and/or more preferably wherein, said other region is located between about positions 14,220 bp and 13,350 bp of RASSF1A.

18. The method of any one of items 1 to 17, wherein said sample is a tissue sample or a sample of biological fluid;

preferably wherein, said sample is a sample of biological fluid selected from the group consisting of: whole blood, a blood fraction, urine, saliva, sweat, ejaculate, tears, phlegm, vaginal secretion, vaginal wash and colonic wash; more preferably wherein, said sample is a plasma or serum sample.

19. The method of any one of items 1 to 18, wherein said reagent that differentially modifies methylated and non-methylated DNA comprises bisulphite.

20. The method of any one of items 1 to 18, wherein said reagent that differentially modifies methylated and non-methylated DNA comprises an agent that selectively digests unmethylated ever methylated DNA, preferably wherein, said agent comprises:
    at least one methylation sensitive enzyme;
    at least one methylation sensitive restriction enzyme; and/or
    an agent selected from the group consisting of: AatII, AcII, AclI, AfeI, AgeI, AgeI-HF, AscI, AsiSI, AvaI, BceAI, BmgBI, BsaAI, BsaAI, BsahI, BsiEI, BsiWI, BsmBI, BspDI, BsrFI, BassHII, BstBI, BstUI, ClaI, EagI, FauI, FseI, FspI, HaeII, HgaI, HhaI, HinP1II, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, PmiI, PvuI, PvuI-HF, RsrII, SacII, SalI, SalI-HF, SfoI, SgrAI, SmaI, SnaBI, TspMI and ZraI.

21. The method of any one of items 1 to 20, wherein each of said detection steps comprises quantitative detection and said detected amount of said species of DNA is expressed as a relative concentration of said species of DNA to the total DNA in said sample.

22. The method of any one of items 1 to 20, further comprising the steps:
    detecting an amount of total DNA in a standard sample of DNA of known amount using the same other regions(s) as used in step (c); and
    comparing the signal detected from said standard sample of DNA to the signal detected in step (c).

23. The method of item 22, wherein each of said detection steps comprises quantitative detection and said defected amount of said species of DNA is expressed as an absolute amount of said species of DNA in said sample.

24. The method of item 21 or 23, further comprising the step:
    comparing the amount of said species of DNA detected with a threshold amount and/or reference distribution of amounts, wherein: (x) an increase in, or outlying of, the amount of said species of DNA indicates an increased risk of the individual suffering from or developing a medical condition; and/or (y) an amount of said species of DNA in excess to said threshold, or outlying from said distribution, indicates that a diagnosis for an abnormality in the said species of DNA present in said sample may be performed on, preferably a separate aliquot of DNA of, said sample, 25. The method of any one of items 21 to 24, further comprising the step:
    performing on, preferably with a separate aliquot of DNA of, said sample, a diagnosis for an abnormality in said species of DNA present in said sample; preferably wherein, said species of DNA originates from cells of a foetus and/or the placenta of a foetus, said sample is from a pregnant female and said diagnosis is a prenatal diagnosis.

26. The method of item 25, wherein said diagnosis comprises a step that uses a detection technology selected from the group consisting of: DNA sequencing, SNP analysis, digital PCR and hybridisation; preferably wherein, said detection technology is massively parallel sequencing of DNA; more preferably wherein said detection technology is massively parallel sequencing of random and/or enriched DNA.

27. The method of item 25 or 26, wherein;
    (x) said species of DNA originates from cells of a foetus and/or the placenta of a foetus, said sample is from a pregnant female and said abnormality is a genetic mutation or a chromosomal abnormality, such as a chromosomal trisomy, associated with a foetal abnormality and/or a congenital disorder; preferably wherein:
        said genetic mutation is selected from the group consisting of: colour blindness, cystic fibrosis, hemochromatosis, haemophilia, phenylketonuria, polycystic kidney disease, sickle-cell and disease, Tay-Sachs disease; and/or
        said chromosomal abnormality is selected from the group consisting of; a trisomy (such as trisomy 21, trisomy 18, or trisomy 13), a sex-chromosome abnormality (such as Turners syndrome, Klinefelter syndrome, Noonan syndrome, Triple X syndrome, XXY syndrome, or Fragile X syndrome), a chromosomal deletion (such as Prader-Willi syndrome, Cris-du-chat syndrome, Wolf-Hirschhorn syndrome, or 22q11 deletion syndrome, Duchene muscular dystrophy), Beckwith-Wiedemann syndrome, Canvan syndrome, and neurofibromatosis; or
    (y) said species of DNA originates from cells of a tumour and said abnormality is a genetic mutation or a chromosomal abnormality associated with the diagnosis, prognosis or predictive treatment of a carcinoma or cancer; preferably wherein;
        said genetic mutation is selected from the group consisting of: a mutation in a tumour suppressor gene (such as TP53 (p53), BRCA1, BRCA2, APC or RB1), a mutation in a proto-oncogene (such as RAS, WNT, MYC, ERK, or TRK) and a DNA repair gene (such as HMGA1, HMGA2, MGMT or PMS2); and/or
        said chromosomal abnormality is a translocation (such as t(9;22)(q34;q11) [ie, Philadelphia chromosome or BCL-ABL], t(8;14)(q24;q32), t(11;14)(q13;q32), t(14;18)(q32;q21), t(10;various))(q11;(various)), t(2; 3)(q13;p25), t(8;21)(q22;q22), t(15;17)(q22;q21), t(12;15)(p13;q25), t(9;12)(p24;p13), t(12;21)(p12; q22), t(11;18)(q21;q21), t(2;5)(p23;q35), t(11;22) (q24;q11.2-12), t(17;22), t(1;12)(q21;p13), t(X;18) (p11.2;q11.2), t(1;19)(q10;p10), t(7,16)(q32-34; p11), t(11,16)(p11p11), t(8,22)(q24;q11) or t(2;8) (p11; q24)), 28. A method for detecting an increased risk of an individual suffering from or developing a medical condition; said method comprising the steps:
    (i) conducting the method of item 21 or 23; and
    (ii) comparing the amount of said species of DNA detected with a threshold amount and/or a reference distribution of amounts,
    wherein an increase in, or outlying of, the amount of said species of DNA indicates an increased risk of the individual suffering from or developing said medical condition.

29. A composition comprising:
    two pairs of PCR primers, each pair for amplifying one of said two of more DMRs as set forth in any of items 1 to 28;

one pair of PCR primers for amplifying said other region as set forth in any of items 1 to 28;
two labelled probes as set forth in item 4; and
one labelled probe as set forth in item 5.

30. The composition of item 29, further comprising:
a further pair of PCR primers for amplifying a second other region as set forth in any of items 9 to 28; and,
a further labelled probe as set forth in item 9.

31. A kit comprising:
the primers and probes as set forth in item 29 or 30; and
optionally, further comprising: (i) a printed manual or computer readable memory comprising instructions to use said primers and probes to practice a method of any one of items 1 to 28 and/or to produce or use the composition of item 29 or 30; and/or (ii) one or more other item, component or reagent useful for the practice of a method of any one of items 1 to 28 and/or the production or use of the composition of item 29 or 30, including any such item, component or reagent disclosed herein, such as the reagent that differently modifies methylated and non-methylated DNA as set forth in any one of items 1 to 28.

32. A computer program product comprising a computer readable medium encoded with a plurality of instructions for controlling a computing system to perform and/or manage an operation for determining; (x) an increased risk of an individual suffering from or developing a medical condition and/or (y) if a diagnosis for an anomaly in a species of DNA originating from cells of a given type may be performed, in each case front a sample from an individual comprising a species of DNA originating from cells of a given type in admixture with differently methylated DNA not originating from cells of said type, the DNA in present in said sample being treated with a reagent that differently modifies methylated and non-methylated DNA as set forth in any one of items 1 to 28; said operation comprising the steps of:
receiving: (i) one signal representing the essentially simultaneous quantitative defection of methylation at two or more DMRs as set forth in step (b) of any one of items 1 to 28; and (ii) one signal representing the essentially simultaneous quantitative detection of total DNA using at least one other region as set forth in step (c) any of items 1 to 28;
determining a parameter from the signals (i) and (ii), wherein the parameter represents a quantitative amount of said species of DNA;
comparing the parameter to with a threshold amount and/or reference distribution of amounts; and
based on such comparison, determining a classification of whether, respectively, (x) an increased risk of an individual suffering from or developing a medical condition exists; and/or (y) a diagnosis for an anomaly in a species of DNA originating from cells of a given type may be performed.

33. The computer program product of item 32, wherein said operation further comprises the steps:
receiving a further signal representing the quantitative detection of total DNA in a standard sample of DNA as set forth in item 22; and
comparing said signal with the signal set forth in (ii) of item 32, so as to determine said parameter that represents an absolute quantitative amount of said species of DNA.

34. The computer program product of item 32 or 33, wherein said operation is for determining if a diagnosis for an anomaly in said species of DNA may be performed, and further comprises the step of determining from said parameter a number of random and/or enriched DNA molecules to be sequenced from, preferably from a separate aliquot of DNA of, said sample as part of said diagnosis.

35. A method for detecting in a sample from an individual an amount of a species of DNA originating from cells of a given type, which sample comprises said species of DNA in admixture with differentially methylated DNA not originating from cells of said type; said method comprising the steps;
(a) treating the DNA present in said sample with a reagent that differentially modifies methylated and non-methylated DNA; and
(b) defecting in said sample the presence of methylation in said species of DNA at two or more DMRs that are differently methylated between said species of DNA and the DNA not originating from cells of said type the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample,
wherein, said detection in step (b) is made using the same aliquot of DNA of said sample, and in the same reaction/detection vessel, and effectively simultaneously for such DMRs, and using (x) multiplex real-time quantitative PCR; and (y) at least two labelled probes each of which specific for one of said DMRs and that are labelled with the same detectable label(s) for each of said DMRs; preferably wherein, said reagent comprises agent as set forth in item 20.

The invention claimed is:

1. A method for quantitatively detecting in a sample from an individual an amount of a species of DNA originating from cells of a given type, which sample comprises said species of DNA in admixture with differently methylated DNA not originating from cells of said type, wherein said species of DNA originates from cells of a fetus and/or the placenta of a fetus and said sample is from a pregnant female; said method comprising the steps:
(a) treating the DNA present in said sample with a reagent that differentially modifies methylated and non-methylated DNA, wherein said reagent comprises at least one methylation sensitive restriction enzyme;
(b) quantitatively detecting in said sample the presence of methylation in said species of DNA at two or more differentially methylated regions (DMRs) that are differently methylated between said species of DNA and the DNA not originating from cells of said type, the modification of DNA of such DMRs by said reagent is sensitive to methylation of DNA, wherein the presence of methylated DNA at one or more of said DMRs indicates the presence of said amount of species of DNA in said sample and the absence of methylated DNA at said DMRs indicates the absence of said species of DNA in said sample, wherein said DMRs are hyper-methylated in fetal DNA and hypo-methylated in maternal DNA; and
(c) quantitatively detecting an amount of total DNA present in said sample using at least one other region that does not comprise a site of methylation recognized by said at least one methylation sensitive restriction enzyme,
wherein, said detection in step (b) and said detection in step (c) are made using the same aliquot of DNA of said sample, and in the same reaction/detection vessel, and effectively simultaneously for such DMRs and other region(s), and using: (x) the same detectable label(s) for each of said DMRs; and (y) a different detectable label(s) for said other region(s); and wherein:
(A) as part of said detection in steps (b) and (c) each DNA region comprising said DMRs and said other region(s) are amplified; and
(B) each detectable label used in step (b) and step (c) is a fluorescent label; and
(C) said detection in step (b) comprises multiplex real-time probe-based quantitative PCR using at least two labelled probes each of which is specific for one of said DMRs; and
(D) said detection in step (c) comprises real-time quantitative probe-based PCR using at least one labelled probe specific for one of said other region(s).

2. The method of claim 1, wherein said other region(s) is/are located between about 20 bp and about 20 kb upstream or downstream of at least one of said DMRs.

3. The method of claim 1, wherein said detection in step (c) comprises using at least two of said other regions, wherein the number of said other regions is the same as the number of DMRs used in step (b), and wherein one of said other regions is located between about 20 bp and about 20 kb upstream or downstream of a DMR used in step (b) and each other of the said other regions is located between about 20 bp and about 20 kb upstream or downstream of another of said DMRs.

4. The method of claim 3, wherein:
(A) said detection in step (c) is made using the same detectable label(s) for each of said other regions; and
(B) said detection in step (c) comprises multiplex real-time quantitative probe-based PCR using at least two labelled probes each of which is specific for one of said other regions.

5. The method of claim 1, wherein said detection in step (c) comprises using at least two of said other regions and wherein said detection in step (c) comprises multiplex real-time quantitative probe-based PCR using at least one labelled probe specific for each of the other region(s).

6. The method of claim 1, wherein said species of DNA is circulating cell-free DNA and said sample is a blood fraction.

7. The method of claim 1, wherein:
(A) each of said DMRs comprises at least one methylation site(s) specific for said at least one methylation sensitive restriction enzyme, and at least one of said DMRs is located in a portion of the genome and/or gene selected from the group consisting of: RASSF1A, TBX3, HLCS, ZFY, CDC42EP1, MGC15523, SOX14 and SPN; and/or
(B) said other region(s) is/are located in a portion of the genome and/or gene selected from the group consisting of: GAPDH, beta-actin, ALB, APOE, RNASEP, RASSF1A, TBX3, HLCS, ZFY, CDC42EP1, MGC15523, SOX14 and SPN.

8. The method of claim 7, wherein at least one of said DMRs is located between about positions 4,700 bp and 5,600 bp of RASSF1A or about positions 1,660 bp and 2,400 bp of TBX3.

9. The method of claim 1, wherein said sample is a tissue sample or a sample of biological fluid, wherein the sample of biological fluid is selected from the group consisting of: whole blood, a blood fraction, urine, saliva, sweat, ejaculate, tears, phlegm, vaginal secretion, vaginal wash and colonic wash.

10. The method of claim 9, wherein said sample is a plasma or serum sample.

11. The method of claim 1, wherein:
said at least one methylation sensitive restriction enzyme is selected from the group consisting of: AatII, AciI, AclI, AfeI, AgeI, AgeI-HF, AscI, AsiSI, AvaI, BceAI, BmgBI, BsaAI, BsaHI, BsiEI, BsiWI, BsmBI, BspDI, BsrFI, BssHII, BstBI, BstUI, ClaI, EagI, FauI, FseI, FspI, HaeII, HgaI, HhaI, HinP1I, HpaII, Hpy99I, HpyCH4IV, KasI, MluI, NaeI, NarI, NgoMIV, NotI, NotI-HF, NruI, Nt.BsmAI, Nt.CviPII, PaeR7I, PluTI, Pm1I, PvuI, PvuI-HF, RsrII, SacII, SalI, SalI-HF, SfoI, SgrAI, SmaI, SnaBI, TspMI and ZraI.

12. The method of claim 1:
(A) wherein each of said detection steps comprises quantitative detection and said detected amount of said species of DNA is expressed as a relative concentration of said species of DNA to the total DNA in said sample; or
(B) wherein said method further comprises the steps:
detecting an amount of total DNA in a standard sample of DNA of known amount using the same other regions(s) as used in step (c); and
comparing the signal detected from said standard sample of DNA to the signal detected in step (c); and
optionally, wherein each of said detection steps comprises quantitative detection and said detected amount of said species of DNA is expressed as an absolute amount of said species of DNA in said sample.

13. The method of claim 12, further comprising the step:
comparing the amount of said species of DNA detected with a threshold amount and/or reference distribution of amounts,
wherein: (x) an increase in, or outlying of, the amount of said species of DNA indicates an increased risk of the individual suffering from or developing a pregnancy-associated medical condition; and/or (y) an amount of said species of DNA in excess to said threshold, or outlying from said distribution, indicates that a prenatal diagnosis for a genetic mutation or a chromosomal abnormality in the species of DNA present in said sample may be performed on a separate aliquot of DNA of said sample.

14. The method of claim 1, wherein two of said DMRs are located on separate chromosomes.

15. The method of claim 1, wherein the other region is located upstream or downstream of one of said DMRs within a distance selected from the group consisting of: between about 15 kb to 10 kb, 12 kb to 8 kb, 10 kb to 8 kb, 11 kb to 7 kb, 11 kb to 10 kb, 9 kb to 8 kb, 8 kb to 6 kb, 6 kb to 4 kb, 4 kb to 2 kb, and 2 kb to 500 bp.

16. The method of claim 15, wherein:
(A) at least one of said DMRs is located in TBX3; and
(B) said other region is located in TBX3.

17. The method of claim 1, wherein at least one of said DMRs is located on chromosome 12.

18. The method of claim 17, wherein:
(A) at least one of said DMRs is located between about positions 1,660 bp and 2,400 bp of TBX3; and/or
(B) said other region is located between about positions 12,400 bp and 13,000 bp of TBX3.

19. The method of claim 1, wherein said pregnant female is susceptible to a pregnancy-associated medical condition.

20. A composition comprising:
two pairs of PCR primers, one pair for amplifying one first region located between about positions 4,700 bp and 5,600 bp of human RASSF1A and the other pair for amplifying another first region located between about positions 1,660 bp and 2,400 bp of human TBX3;
one pair of PCR primers for amplifying one other region in the human genome;
two fluorescently labelled real-time quantitative PCR probes each of which is specific for one of said first regions but using the same detectable label(s) for each of said probes; and
one fluorescently labelled real-time quantitative PCR probe specific for said other region that has a different detectable label than that of the fluorescently labelled probes which are specific for each of said first regions.

21. The composition of claim 20, wherein said composition is contained in a single reaction/detection vessel.

22. The composition of claim 20, wherein said composition further comprises amplified DNA regions comprising said first regions and said other region.

23. A kit comprising:
two pairs of PCR primers, one pair for amplifying one first region located between about positions 4,700 bp and 5,600 bp of human RASSF1A and the other pair for amplifying another first region located between about positions 1,660 bp and 2,400 bp of human TBX3;
one pair of PCR primers for amplifying one other region in the human genome;
two fluorescently labelled real-time quantitative PCR probes each of which is specific for one of said first regions but using the same detectable label(s) for each of said probes; and
one fluorescently labelled real-time quantitative PCR probe specific for said other region that has a different detectable label than that of the fluorescently labelled probes which are specific for each of said first regions,
wherein at least one of the pairs of PCR primers or at least one of the probes are provided in a separate holder; and
wherein said kit optionally, further comprises: (i) a printed manual or computer readable memory comprising instructions to use said primers and probes;

and/or (ii) a reagent that differently modifies methylated and non-methylated DNA, wherein said reagent comprises at least one methylation sensitive restriction enzyme.

24. A computer program product comprising a non-transitory computer readable medium encoded with a plurality of instructions for controlling a computing system to perform and/or manage an operation for determining: (x) an increased risk of an individual suffering from or developing a medical condition and/or (y) if a diagnosis for an anomaly in a species of DNA originating from cells of a fetus and/or the placenta of a fetus may be performed; said operation comprising the steps of:

receiving: (i) a first signal from multiplex real-time quantitative probe-based PCR representing the essentially simultaneous quantitative detection of methylation at two or more differentially methylated regions (DMRs) in a species of DNA originating from cells of a fetus and/or the placenta of a fetus in a sample from a pregnant female, wherein said DMRs are hyper-methylated in fetal DNA and hypo-methylated in maternal DNA, wherein the DNA present in said sample is treated with at least one methylation sensitive restriction enzyme, wherein said multiplex real-time quantitative probe-based PCR comprises the use of at least two labelled probes each of which is specific for one of said DMRs and wherein detection of the DMRs is made using the same fluorescent label and in the same reaction/vessel; and (ii) a second signal from real-time quantitative probe-based PCR representing the essentially simultaneous quantitative detection of total DNA in the sample using at least one other region(s), wherein said other regions(s) do(es) not comprise a site of methylation recognized by the at least one methylation sensitive restriction enzyme, wherein said real-time quantitative probe-based PCR comprises use of at least one labelled probe specific for the at least one other region(s) in the sample, wherein detection of said other region(s) is made using a fluorescent label, wherein said fluorescent label for the other region(s) is different from the fluorescent label used to detect the DMRs, and wherein said detections of (i) and (ii) are made using the same aliquot of DNA of said sample and in the same reaction/detection vessel and effectively simultaneously for the DMRs and other region(s);

comparing the first signal with the second signal to thereby obtain a parameter, wherein the parameter represents an enhanced quantitative amount of said species of fetal DNA in the sample, wherein said enhanced quantitative amount is more accurate than a quantitative amount of said species of fetal DNA in the sample obtained by detecting each DMR with a different detectable label and/or each DMR in a separate reaction vessel;

comparing the parameter to a threshold amount and/or reference distribution of amounts; and based on such comparison, determining a classification of whether, respectively, (x) an increased risk of an individual suffering from or developing a medical condition exists; and/or (y) a diagnosis for an anomaly in the species of DNA originating from the cells of the fetus and/or the placenta of the fetus may be performed.

* * * * *